US009867866B2

(12) United States Patent
Burkin et al.

(10) Patent No.: US 9,867,866 B2
(45) **Date of Patent: *Jan. 16, 2018**

(54) METHODS FOR DIAGNOSING, PROGNOSING AND TREATING MUSCULAR DYSTROPHY

(71) Applicant: Board of Regents of the Nevada System of Higher Education on behalf of the University of Nevada, Reno, Reno, NV (US)

(72) Inventors: Dean Burkin, Sparks, NV (US); Ryan Wuebbles, Sparks, NV (US); Pam Van Ry, Reno, NV (US)

(73) Assignee: BOARD OF REGENTS OF THE NEVADA SYSTEM OF HIGHER EDUCATION ON BEHALF OF THE UNIVERSITY OF NEVADA, RENO, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,063

(22) PCT Filed: Aug. 9, 2013

(86) PCT No.: PCT/US2013/054384

§ 371 (c)(1),
(2) Date: Feb. 2, 2015

(87) PCT Pub. No.: WO2014/026140

PCT Pub. Date: Feb. 13, 2014

(65) Prior Publication Data

US 2015/0196618 A1 Jul. 16, 2015

Related U.S. Application Data

(63) Continuation of application No. 13/572,508, filed on Aug. 10, 2012, now Pat. No. 9,694,049.

(60) Provisional application No. 61/522,507, filed on Aug. 11, 2011.

(51) Int. Cl.

| | |
|---|---|
| ***A61K 38/17*** | (2006.01) |
| ***A61P 21/00*** | (2006.01) |
| ***C12Q 1/68*** | (2006.01) |
| ***G01N 33/68*** | (2006.01) |

(52) U.S. Cl.

CPC ...... *A61K 38/1709* (2013.01); *A61K 38/1732* (2013.01); *C12Q 1/6883* (2013.01); *G01N 33/6896* (2013.01); *C12Q 2600/118* (2013.01); *C12Q 2600/136* (2013.01); *C12Q 2600/158* (2013.01); *G01N 2333/42* (2013.01); *G01N 2333/4724* (2013.01); *G01N 2500/00* (2013.01); *G01N 2800/2878* (2013.01); *G01N 2800/2885* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 6,168,920 | B1 | 1/2001 | Hillman |
| 6,283,761 | B1 | 9/2001 | Joao |
| 2006/0014287 | A1 | 1/2006 | Sherwood et al. |
| 2007/0025972 | A1 | 2/2007 | Rodriguez et al. |
| 2010/0004163 | A1 | 1/2010 | Panjwani |

FOREIGN PATENT DOCUMENTS

| | | |
|---|---|---|
| RU | 2372941 | 11/2009 |

OTHER PUBLICATIONS

Camby et al., Glycobiology, 2006, vol. 16(11):137R-157R.*

Berard et al., Neuromuscul. Disord., 2005, vol. 15:463-470.*

Cerri, et al, "Degeneration of dystrophic or injured skeletal muscles induces high expression of Galectin-1;" Glycobiology, US, (Aug. 22, 2008), vol. 18, No. 11, doi:10.1093/glycob/cwn079, ISSN 0959-6658, p. 842-850, XP055250489 [Y] 1-15 abstract; 2008.

European Patent Application No. 13827774.4; Search Report/Opinion dated Mar. 29, 2016.

Kami, et al, "Galectin-1 is a novel factor that regulates myotube growth in regenerating skeletal muscles;" Current Drug Targets, Bentham Science Publisher, US, vol. 6, No. 4, ISSN 1389-4501, p. 395-405, XP009110394, 1-15 Abstract; Fig. 5; p. 403, left col.; 2005.

Pace, Karen E et al, "Preparation of recombinant human galectin-1 and use in T-cell death assays;" Methods in Enzymology, Academic Press, US, (Jan. 1, 2003), vol. 363, ISSN 0076-6879, p. 499-518, XP009188593; 2003.

Perone, M.J., et al.; Suppression of autoimmune diabetes by soluble galectin-1; Journal of Immunology, vol. 182 p. 2641-2653; 2009.

(Continued)

*Primary Examiner* — Xiaozhen Xie

(74) *Attorney, Agent, or Firm* — Schwabe, Williamson & Wyatt

(57) ABSTRACT

Disclosed herein are methods for diagnosing, prognosing and treating muscular dystrophy. Also disclosed are methods of determining the effectiveness of an agent for the treatment of muscular dystrophy. Provided are methods of enhancing muscle regeneration, repair, or maintenance in a subject by administering galectin, such as Galectin-1 and/or Galectin-3 to a subject in need thereof. Also disclosed are methods of increasing or maintaining muscle strength and/or bone density in a subject by administering an effective amount of a Galectin-1 composition, Galectin-3 composition or a combination thereof to the subject in need thereof. Methods of preventing, inhibiting and/or reducing muscle loss and/or bone loss in a subject by administering an effective amount of a Galectin-1 composition, Galectin-3 composition or a combination thereof to the subject in need thereof are disclosed.

15 Claims, 26 Drawing Sheets

(56) References Cited

OTHER PUBLICATIONS

Watt, Diana J et al, "The involvement of galectin-1 in skeletal muscle determination, differentiation and egeneration;" Glycoconjugate Journal, Kluwer Academic Publishers, BO, (Jan. 1, 2002), vol. 19, No. 7-9, doi:10.1023/B:GLYC.0000014093.23509.92, ISSN 1573-4986, p. 615-619, XP019206952 [A] 1-15 Abstract; p. 615, right col.;p. 616, right and left col.;p. 617, left col.; 2002.

Andersen, et al., "A Proteome Study of Secreted Prostatic Factors Affecting Osteoblastic Activity: Galectin-1 Is Involved in Differentiation of Human Bone Marrow Stromal Cells." *Journal of Bone and Mineral Research*, 18.2 (2003): pp. 195-203.

Camby, et al., "Galectin-1: a small protein with major functions." *Glycobiology*, 16.11 (2006): pp. 137R-157R.

Chan et al., "Galectin-1 Induces Skeletal Muscle Differentiation in Human Fetal Mesenchymal Stem Cells and Increases Muscle Regeneration," *Stem Cells*, 24:1879-1891, 2006.

Doe et al., "Transgenic overexpression of the α7 integrin reduces muscle pathology and improves viability in the $dy^W$ mouse model of merosin-deficient congenital muscular dystrophy type 1A," *J. Cell Science*, 124:2287-2297, Jun. 7, 2011.

Georgiadis et al., "Lack of Galectin-1 Results in Defects in Myblast Fusion and Muscle Regeneration," *Developmental Dynamics*, 236:1014-1024, 2007.

Goldring, et al., "The effect of galectin-1 on the differentiation of fibroblasts and myoblasts in vitro." *Journal of Cell Science*, 115.2 (2002): pp. 355-366.

International Search Report and Written Opinion, dated Nov. 28, 2013, by the International Search Authority, Russia, for PCT Patent Application No. PCT/US2013/054384, 5 pp.

Jing, et al., "Differential expression of galectin-1 and its interactions with cells and laminins in the intervertebral disc." *Journal of Orthopaedic Research*, 30.12 (2012): pp. 1923-1931.

Murphy et al., "An improved method for the in vitro evolution of aptamers and applications in protein detection and purification," *Nucl. Acids Res.* 31:e110 (2003).

Ortega, et al., "Galectin-3 is a downstream regulator of matrix metalloproteinase-9 function during endochondral bone formation." *Molecular Biology of the Cell*, 16.6 (2005): pp. 3028-3039.

Van Den Brûle, Frédéric A., et al., "Differential expression of Galectin-1 and Galectin-3 during first trimester human embryogenesis." Developmental Dynamics, 209.4 (1997): pp. 399-405.

Vinik, Yaron, "The lectin that will break your bones: Galectin-8 modulates bone remodeling and cancer metastasis," available at: http://www.weizmann.ac.il/pages/event/4372?popup, last accessed Jul. 15, 2013, 1 page.

Wlotzka et al., In vivo properties of an anti-GnRH Spiegelmer: An example of an oligonucleotide-based therapeutic substance class, *Proc. Natl Acad.* Sci, 99(13):8898-8902 (2002).

Horie, H., et al.; "Galectin-1 regulates initial axonal growth in peripheral nerves after axotomy;" Journal of Neuroscience, The Society, Washington, DC, US, vol. 19, No. 22, pp. 9964-9974, jXP002983702, ISSN: 1529-2401; Jan. 1, 1999.

Horie, H., et al; "Galectin-1 plays essential roles in adult mammalian nervous tissues. Roles of oxidized galectin-1;"Glycoconjugate Journal, Kluwer Academic Publishers, Bo; vol. 19, No. 7-9, pp. 479-489, XP019206936; issn: 1573-4986, DOI: 10.1023/B:GLYC.0000014077.84016.52; Jan. 1, 2002.

* cited by examiner

FIG. 2B
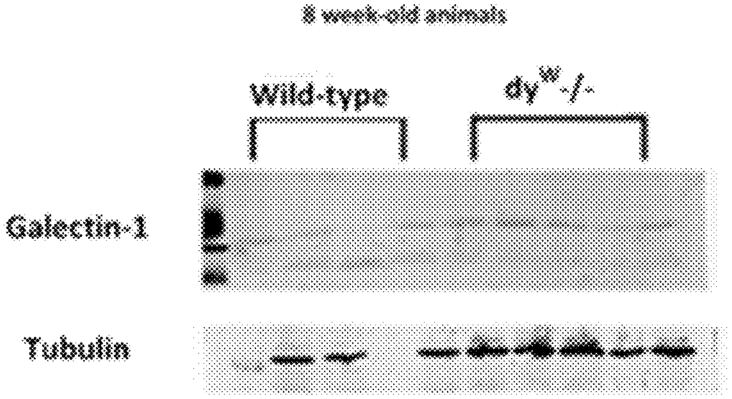
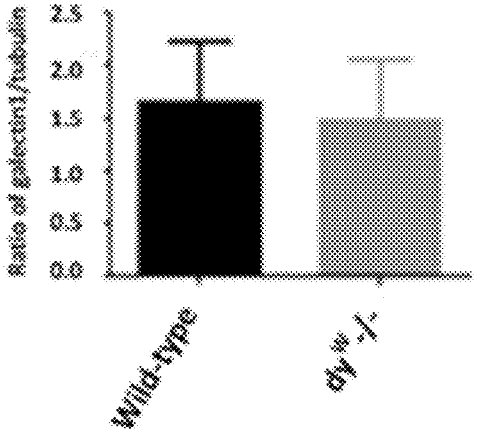
FIG. 2C
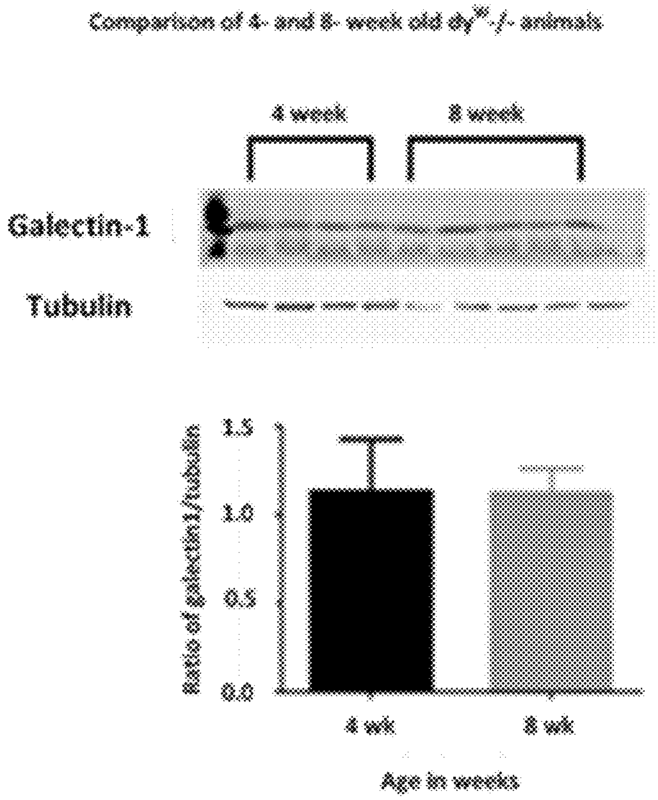

| Well # | 2 | 3 | 4 | 5 | 6 | 7 | 8 | 9 | 10 | 11 | 12 | 13 | 14 |
|---|---|---|---|---|---|---|---|---|---|---|---|---|---|
| Fraction | 1 | 2 | 3 | 4 | 5 | 6 | 7 | 8 | 9 | 10 | 11 | 12 | 13 |
| [μM] | 74 | 53 | 111 | 474 | 372 | 640 | 294 | 71 | 32 | 24 | 21 | 20 | 19 |

| %CLN | Treated | non treated |
|---|---|---|
| mdx ♂ n=3 | 32 | 47 |
| mdx ♀ n=2 | 16 | 37 |

FIG. 14
| [Gal-1]nM | 72 hours | 96 hours | 96 hours |
|---|---|---|---|
| 0 | 3.3 | 1.8 | 3.0 |
| 50 | 2.5 | 5.5 | 4.0 |
| 100 | 4.0 | 7.2 | 5.0 |
| 150 | 5.3 | 2.7 | 3.4 |
| 250 | 6.1 | 4.7 | 2.4 |
| 500 | 3.6 | 3.4 | 4.2 |
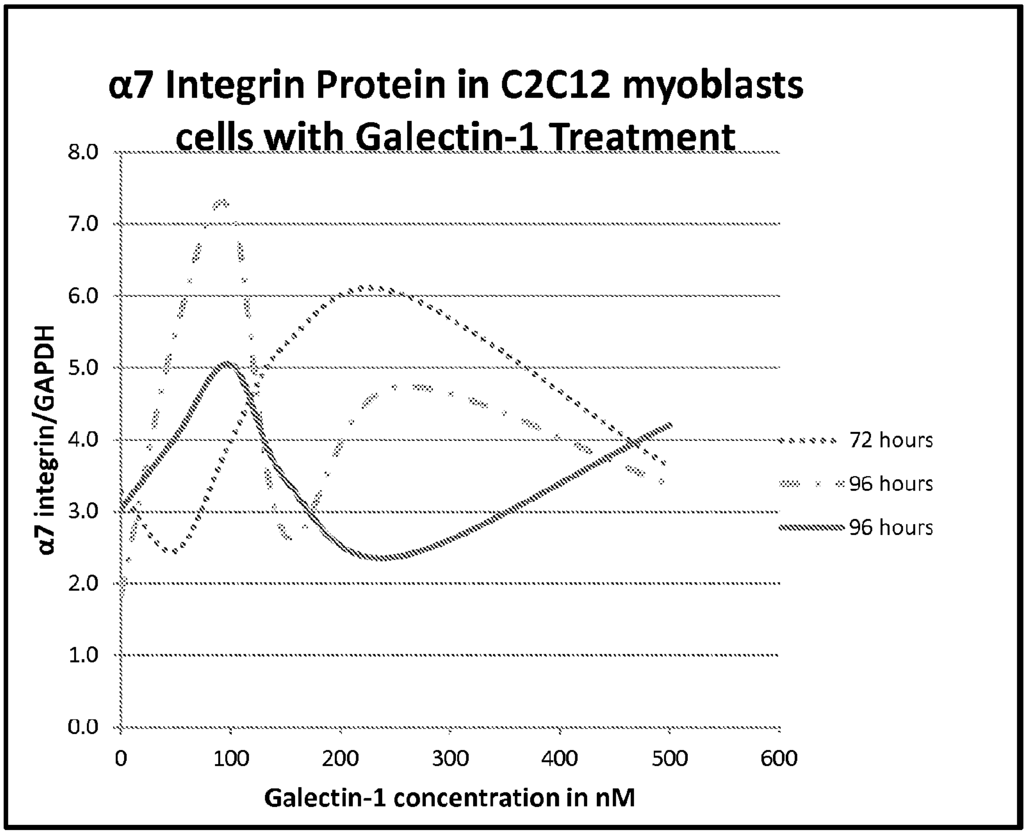
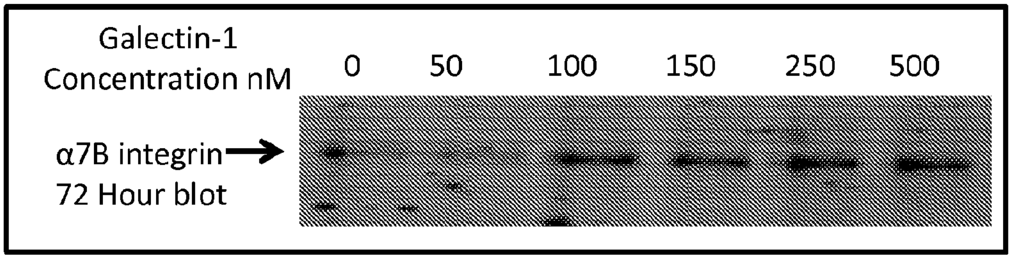

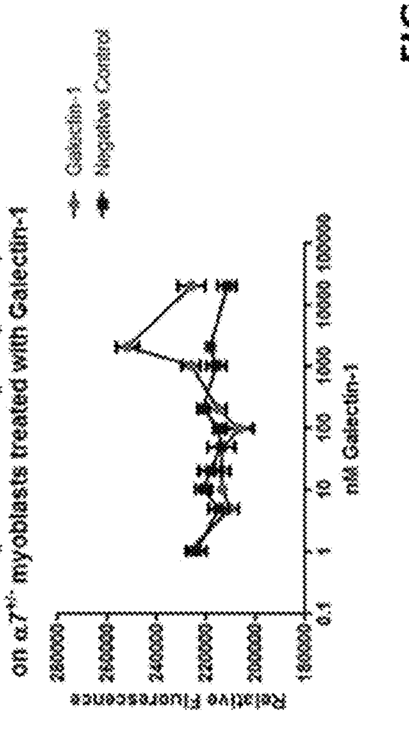

FIG. 15A

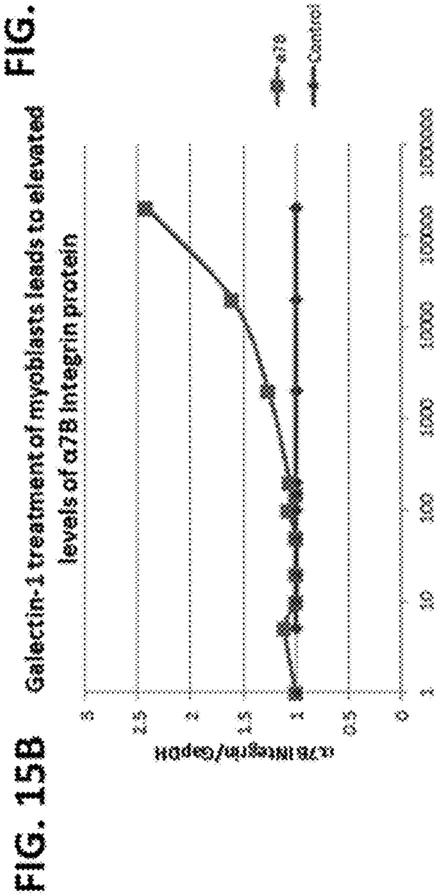

FIG. 15B

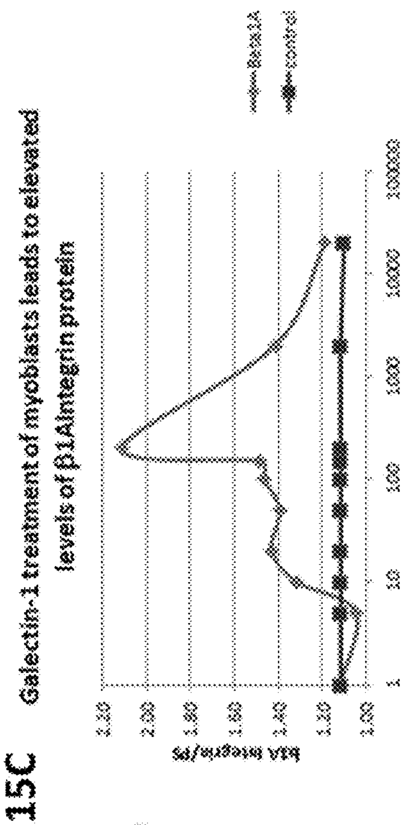

FIG. 15C

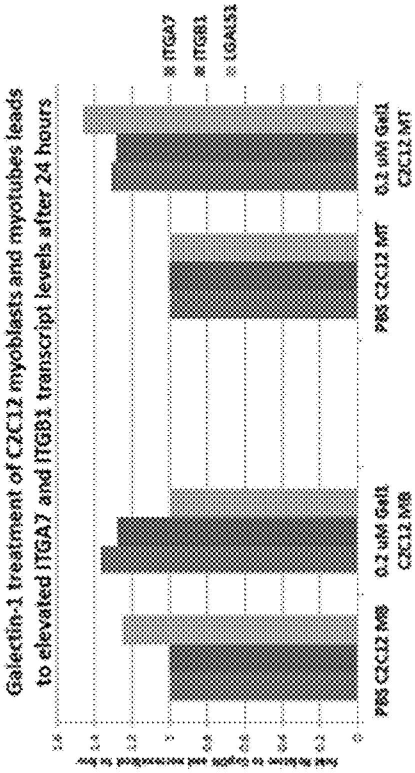

FIG. 15D

FIG. 15A  α7 integrin enhancing drug assay on α7+/+ myoblasts treated with Galectin-1

FIG. 15B  Galectin-1 treatment of myoblasts leads to elevated levels of α7B integrin protein FIG. 15C  Galectin-1 treatment of myoblasts leads to elevated levels of β1A integrin protein FIG. 15D  Galectin-1 treatment of C2C12 myoblasts and myotubes leads to elevated ITGA7 and ITGB1 transcript levels after 24 hours FIG. 16A
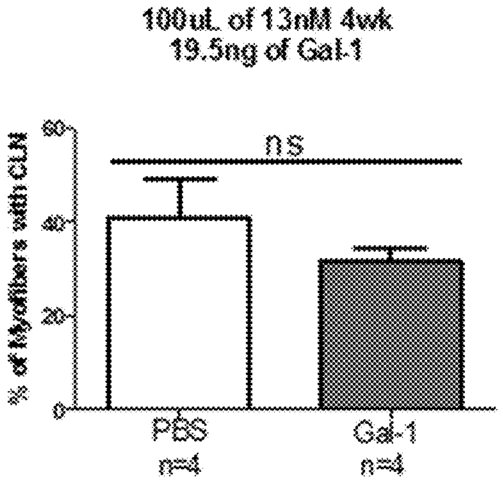
FIG. 16B
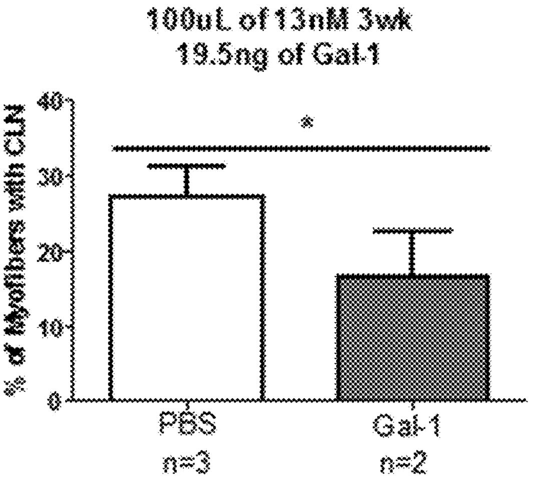
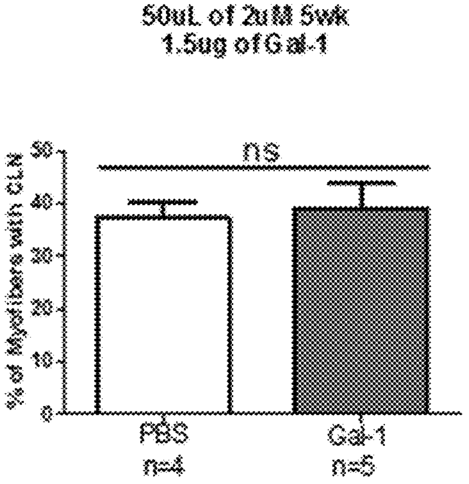
FIG. 16C
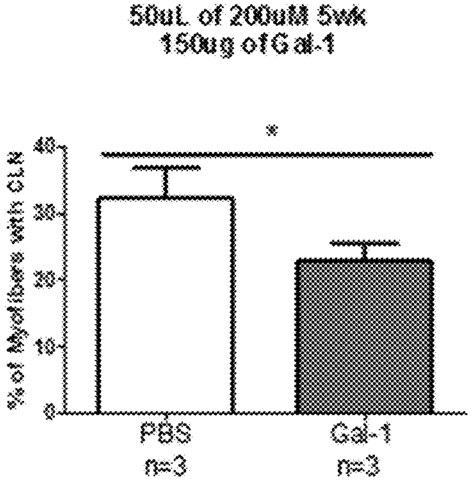
FIG. 16D FIG. 19A
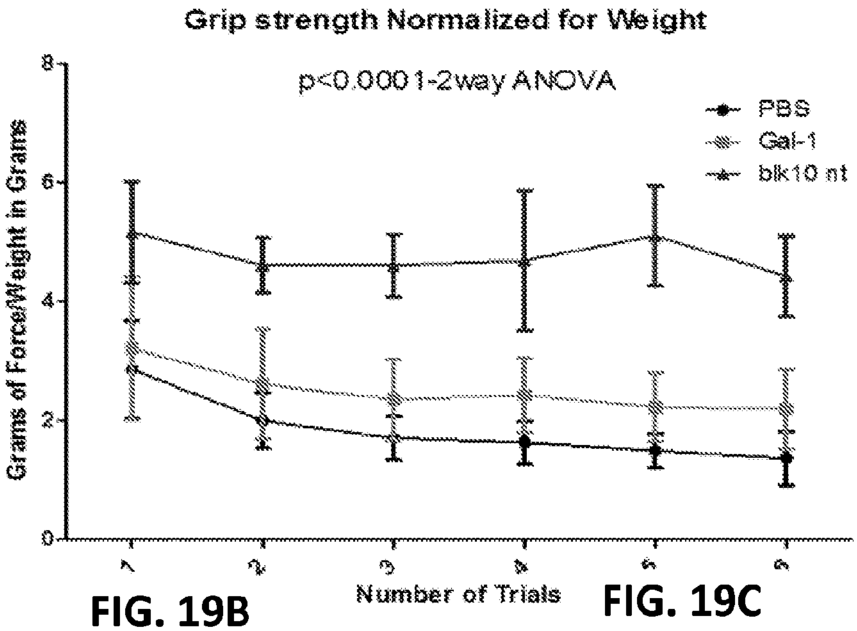
FIG. 19B
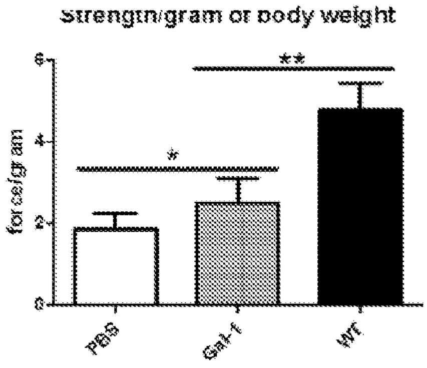
FIG. 19C
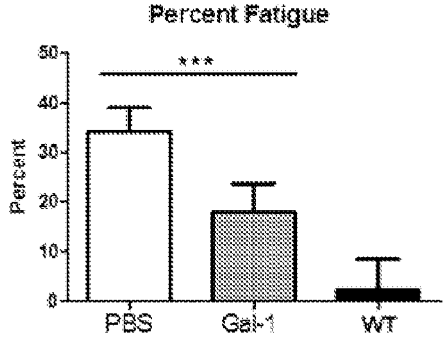
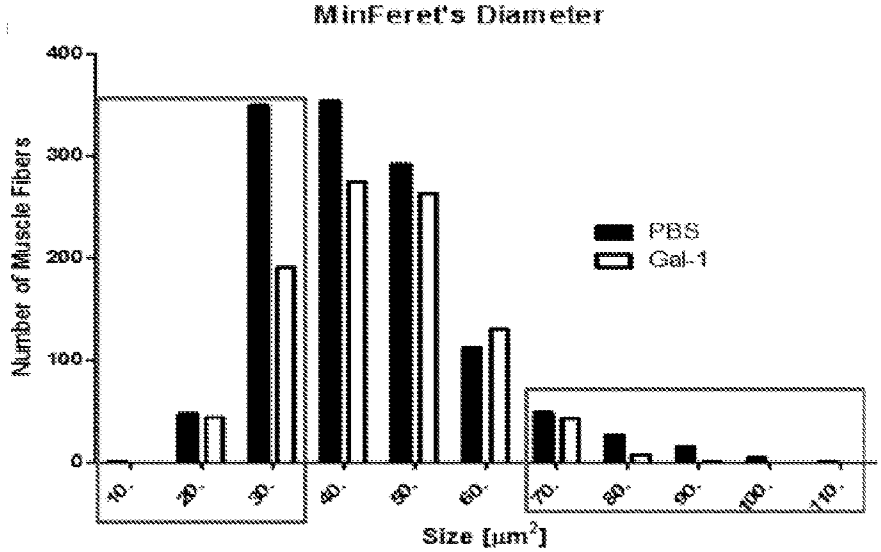
FIG. 19D

METHODS FOR DIAGNOSING, PROGNOSING AND TREATING MUSCULAR DYSTROPHY

CROSS REFERENCE TO RELATED APPLICATIONS

This is the U.S. National Stage of International Application No. PCT/US2013/054384, filed Aug. 9, 2013, which was published in English under PCT Article 21(2), which in turn claims the benefit of U.S. application Ser. No. 13/572,508, filed Aug. 10, 2012. U.S. application Ser. No. 13/572,508, filed Aug. 10, 2012, claims benefit to U.S. Provisional Application No. 61/522,507, filed Aug. 11, 2011, each of these applications are incorporated herein in their entirety.

ACKNOWLEDGMENT OF GOVERNMENT SUPPORT

This invention was made with government support under R01 AR053697 and R21 NS58429 awarded by the National Institutes of Health. The government has certain rights in the invention.

FIELD

This disclosure relates to the field of muscular dystrophy and in particular, to methods for diagnosing, prognosing and treating patients with muscular dystrophy, such as merosin deficient congenital muscular dystrophy Type 1A, limb-girdle muscular dystrophy, facioscapulohumeral muscular dystrophy, Beckers muscular dystrophy and Duchenne muscular dystrophy.

BACKGROUND

The muscular dystrophies are a group of diverse, heritable neuromuscular disorders which represent a group of devastating neuromuscular diseases characterized by primary or secondary skeletal muscle involvement. Duchenne muscular dystrophy (DMD) is an X-chromosome-linked disease and the most common form of muscular dystrophy. DMD affects 1 in 3500 live male births with patients suffering from chronic muscle degeneration and weakness. Clinical symptoms are first detected between the ages of 2 and 5 years and, by the time the patient is in their teens, the ability for independent ambulation is lost. Death typically occurs in the patient before they are 30 years old due to cardiopulmonary failure.

Congenital muscular dystrophy (CMD) refers to a group of heritable neuromuscular disorders characterized by muscle weakness at birth or in infancy. Affected infants will present with poor muscle tone and few movements. The quality of life and life span of the child is affected through progressive muscle wasting, respiratory compromise, and spinal rigidity. Merosin deficient congenital muscular dystrophy (MDC1A) is the most common and severe form of congenital muscular dystrophy, accounting for 30-40% of all CMD diagnosed cases. MDC1A is characterized by congenital hypotonia, distinct joint contractures, and a lack of independent ambulation. Feeding tube placement and positive pressure ventilation is often required for the respiratory problems that occur. MDC1A has no cure and patients often die before they reach the age of ten years. Currently there is no cure for either DMD or MDC1A.

SUMMARY

Muscular dystrophies including MDC1A, DMD, Limb-Girdle muscular dystrophy (LGMD), facioscapulohumeral muscular dystrophy (FHMD), Beckers muscular dystrophy are devastating neuromuscular diseases. In addition to there being no cure for such diseases, there are no non-invasive methods of diagnosing, prognosing or evaluating the efficacy of treatments for such conditions. Currently, serum creatine kinase levels and fine needle biopsies are used as tests for DMD, LGMD, FMD, Beckers muscular dystrophy and MDC1A. However, muscle biopsies are painful, invasive and impractical to perform consistently, and serum creatine kinase levels can vary from day to day in the same patient making, them unreliable indicators of change. A biomarker which can be monitored easily, such as in serum or urine, and that can reliably indicate disease progression is needed.

Disclosed herein are muscular dystrophy-associated molecules that can be used as biomarkers to diagnose and/or prognose muscular dystrophy, including DMD, LGMD, FHMD, Beckers muscular dystrophy and/or MDC1A. In some embodiments, the muscular dystrophy-associated molecules can include, consist essentially of, or consist of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin $\alpha3$ (Iga3), integrin $\alpha6$ (Iga6), integrin $\alpha7$ (Iga7), laminin-$\alpha4$ (Lama4), laminin-$\alpha5$ (Lama5), nidogen 1 (Nid1), tenascin C (Tnc), tissue inhibitor of metalloproteinase 1 (Timp1), tissue inhibitor of metalloproteinase 2 (Timp2) or any combination thereof. In some examples, muscular dystrophy-associated molecules include Galectin-1, Galectin-3, Col6A1, Itga3, Iga6, Itga7, Tnc and Timp 1. In some examples, muscular dystrophy-associated molecules include Galectin-1 and Galectin-3. In some examples, muscular dystrophy-associated molecules include Galectin-3 and Tnc. In some examples, the muscular dystrophy-associated molecules include at least Galectin-3 for detecting DMD, LGMD, FHMD, Beckers muscular dystrophy or MDC1A. In some examples, the muscular dystrophy-associated molecules include at least Galectin-3 for detecting DMD.

Also disclosed herein are methods of diagnosing or prognosing a subject with muscular dystrophy. In some examples, the method includes detecting at least one of the disclosed muscular dystrophy-associated molecules in a sample obtained from the subject at risk of having or having one or more signs or symptoms associated with muscular dystrophy, thereby diagnosing or prognosing the subject with muscular dystrophy. In some examples, the method further includes comparing expression of Galectin-1 or Galectin-3 in the sample obtained from the subject at risk of having or having one or more signs or symptoms associated with muscular dystrophy to a control, wherein increased expression of Galectin-1 or Galectin-3 molecules relative to a control indicates that the subject has muscular dystrophy.

Further, methods of determining the effectiveness of an agent for the treatment of muscular dystrophy in a subject with muscular dystrophy are disclosed. In some examples, the methods include detecting expression of a muscular dystrophy-associated molecule, such as Galectin-3, in a sample from the subject following treatment with the agent; and comparing expression of the muscular dystrophy-associated molecule, such as Galectin-3, following treatment to a reference value, wherein an alteration in the expression of the muscular dystrophy-associated molecule, such as Galectin-3, following treatment indicates that the agent may be effective for the treatment of muscular dystrophy in the subject.

Also disclosed are methods of treating muscular dystrophy. In some examples, the method includes administering to the subject with muscular dystrophy an effective amount of an agent that alters the expression or biological activity of a muscular dystrophy-associated molecule thereby treating the muscular dystrophy and increasing the subject's chance of survival or delaying the onset of one or more signs or symptoms associated with the muscular dystrophy. Depending upon the agent, the alteration may be a decrease or an increase.

Methods of treating a subject with galectin or a composition that includes galectin are also disclosed. For example, some embodiments provide methods of improving muscular health, such as enhancing muscle regeneration, maintenance, or repair in a subject by administering to the subject an effective amount of galectin or a composition comprising galectin, including fragments, derivatives, or analogs thereof.

In some embodiments, methods of increasing/maintaining muscle strength and/or bone density are provided. In some embodiments, methods of preventing, inhibiting and/or reducing muscle and/or bone loss are provided. In some examples, a galectin composition, such as galectin-1 composition, is administered to increase muscle strength and/or bone density and/or prevent, inhibit or slow muscle and bone loss. In some examples, a galectin composition, such as galectin-1 composition, is administered to a subject at risk of muscle/bone injury or muscle/bone loss, such as to an athlete, an astronaut, or any other individual that partakes in activities that may cause muscle/bone injury and/or loss. In some examples, a disclosed regimen, such as a disclosed Galectin-1 regimen, is provided to prevent muscle/bone injury and/or loss. In some examples, a disclosed regimen, such as a disclosed Galectin-1 regimen, is provided to maintain bone density and/or muscle strength. In some examples, a disclosed regimen, such as a disclosed Galectin-1 regimen, is provided to treat a subject experiencing a loss in bone density and/or muscle strength whereby the regimen is administered in a manner to lead to an increase in bone density and/or muscle strength or to maintain the existing muscle strength and bone density (e.g., prevent further loss of muscle strength and/or bone density).

In some examples, a galectin composition, such as a Galectin-1 composition, is administered to a subject at risk of acquiring or suffering from a condition or disease associated with muscle loss, bone loss, muscle density loss, and/or muscle strength loss, such as, but not limited to a subject at risk of acquiring or suffering from kyphosis, muscular dystrophies, broken bones, muscle strains, muscle tears, tendon injury, osteoporosis, rheumatoid arthritis, lupus, scoliosis and/or multiple sclerosis. In some examples, a galectin composition, such as a Galectin-1 composition, is administered for preventing, treating or slowing the progression of a sign or symptom associated with aging. It is contemplated that a galectin composition can be administered for short or prolong periods of time, ranging from days to years. It is contemplated that a galectin composition can be administered as a nutritional supplemental.

In some examples, a galectin composition, such as Galectin-1, is administered post-surgery, such as to a subject that has undergone surgery and may be at risk of experiencing or has muscle loss, bone loss, muscle strength loss or muscle density loss. In some examples, a galectin composition, such as Galectin-1, is administered to a female subject post-pregnancy. In some examples, a galectin composition, such as Galectin-1, is administered to a short or long-term coma subject.

In a specific example, the galectin is a complete galectin protein, such as Galectin-1 or Galectin-3. In further examples, the galectin is selected from Galectin-1, Galectin-3, and combinations thereof. In further examples, the galectin or galectin composition includes a substance at least substantially homologous to Galectin-1 or Galectin-3. In yet further implementations, the galectin or galectin composition comprises a polypeptide at least substantially homologous to the Galectin-1 or Galectin-3.

In additional examples, the galectin or galectin composition consists of Galectin-1, Galectin-3, and combinations thereof. In further examples, the galectin or galectin composition consists of a substance at least substantially homologous to Galectin-1 or Galectin-3. In a specific example, the galectin or galectin composition does not include a galectin fragment, such as including only a complete galectin protein.

In yet another example, the galectin or galectin composition consists essentially of Galectin-1, Galectin-3, and combinations thereof. In further examples, the galectin or galectin composition consists essentially of a substance at least substantially homologous to Galectin-1 or Galectin-3. In yet further implementations, the galectin or galectin composition consists essentially of a polypeptide at least substantially homologous to the galectin $\alpha1$ chain. In a specific example, the galectin or galectin composition does not include a galectin fragment, such as including essentially only a complete galectin protein.

Further implementations of the disclosed method include diagnosing the subject as having a condition treatable by administering galectin or a composition comprising galectin, such as by administering Galectin-1, Galectin-3 or a combination thereof or a composition containing Galectin-1, Galectin-3 or a combination. In one example, the subject is diagnosed as suffering from muscular dystrophy, such as LGMD, FHMD, Beckers muscular dystrophy and/or MDC1A. In further instances the condition is characterized by the failure of a subject, or the reduced ability of the subject, to express one or more proteins associated with the formation or maintenance of the extracellular matrix, such as impaired or non-production of a galectin, an integrin, dystrophin, utrophin, or dystroglycan.

In a specific embodiment, the present disclosure also provides a method for increasing muscle regeneration in a subject by administering an effective amount of a galectin composition, such as an effect amount of a Galectin-1 and/or Galectin-3 composition. For example, geriatric subjects, subjects suffering from muscle disorders, and subjects suffering from muscle injury, including activity induced muscle injury, such as injury caused by exercise, may benefit from this embodiment.

In yet further embodiments of the disclosed method, the galectin or galectin composition, such as Galectin-1, Galectin-3 or a combination thereof containing composition, is administered in a preventative manner, such as to prevent or reduce muscular or bone damage or injury (such as activity or exercise induced injury). For example, geriatric subjects, post-surgery subjects, post-pregnancy, subjects prone to muscle damage, or subjects at risk for muscular injury, such as athletes, may be treated in order to prevent, eliminate or ameliorate bone or muscular damage, injury, or disease.

Implementations of the present disclosure may also be used to promote wound healing. In some examples, a galectin or a composition comprising galectin is administered into or proximate to a wound. In further examples, the substance is administered systemically. Although the substance is typically applied after the wound occurs, the substance is applied prospectively in some examples.

In further embodiments, the method of the present disclosure includes administering the galectin or galectin composition, such as Galectin-1, Galectin-3 or a combination thereof containing composition, with one or more additional pharmacological substances, such as a therapeutic agent. In some aspects, the additional therapeutic agent enhances the therapeutic effect of the galectin or galectin composition. In further aspects, the therapeutic agent provides independent therapeutic benefit for the condition being treated. In various examples, the additional therapeutic agent is a component of the extracellular matrix, such as an integrin, dystrophin, dystroglycan, utrophin, or a growth factor. In further examples, the therapeutic agent reduces or enhances expression of a substance that enhances the formation or maintenance of the extracellular matrix.

In some examples, the galectin or galectin composition is applied to a particular area of the subject to be treated. For example, the galectin or galectin composition may be injected into a particular area to be treated, such as a muscle. In further examples, the galectin or galectin composition is administered such that it is distributed to multiple areas of the subject, such as systemic administration or regional administration.

Galectin, or a composition comprising galectin, such as Galectin-1, Galectin-3, or a combination thereof, can be administered by any suitable method, such as topically, parenterally (such as intravenously or intraperitoneally), or orally. In a specific example, the galectin or galectin composition is administered systemically, such as through parenteral administration, such as stomach injection or peritoneal injection.

Although the disclosed methods generally have been described with respect to muscle regeneration, the disclosed methods also may be used to enhance repair or maintenance, or prevent damage to, other tissues and organs. For example, the methods of the present disclosure can be used to treat symptoms of muscular dystrophy stemming from effects to cells or tissue other than skeletal muscle, such as impaired or altered brain function, smooth muscles, or cardiac muscles.

Methods of identifying agents for use in treating muscular dystrophy are also provided. In some examples, the method includes contacting a sample with one or more test agents under conditions sufficient for the one or more test agents to alter the activity of a muscular dystrophy-associated associated molecule, such as Galectin-1 or Galectin-3; detecting activity of the muscular dystrophy-associated molecule, such as Galectin-1 or Galectin-3, in the presence of the one or more test agents; and comparing activity of muscular dystrophy-associated molecule, such as Galectin-1 or Galectin-3, in the presence of the one or more test agents to a reference value to determine if there is an alteration in expression of the muscular dystrophy-associated molecule, such as Galectin-1 or Galectin-3, wherein altered expression of the muscular dystrophy-associated molecule, such as Galectin-1 or Galectin-3, indicates that the one or more test agents may be of use to treat the muscular dystrophy. In some examples, an increase in Galectin-1 indicates that the test agent can be used to treat muscular dystrophy.

The foregoing and other features of the disclosure will become more apparent from the following detailed description, which proceeds with reference to the accompanying figures.

BRIEF DESCRIPTION OF THE DRAWINGS

FIG. 1A shows the transcript for Lgals1 (Galectin-1) was significantly increased over wild-type in both 4- and 8-week old animals. FIG. 1B illustrated that the transcript for Lgals3 (Galectin-3) was also significantly increased over wild-type in both 4- and 8-week old animals. $^{}P<0.01$, $^{**}P<0.00001$.

FIGS. 2A-2C are digital images and bar graphs illustrating Western blotting studies for Galectin-1 in the $dy^W$–/– and wild-type mice at 4- and 8-weeks of age. FIG. 2A shows the difference in Galectin-1 protein in the muscles of 4-week old $dy^W$–/– mice was significantly different from wild-type animals. FIG. 2B indicates that the level of Galectin-1 protein in the grostocnemius muscle of 8-week old $dy^W$–/– animals was not significantly different from that measured in wild-type. FIG. 2C shows that there was no difference in Galectin-1 protein in $dy^W$–/– mice at 4- and 8-weeks of age.

FIG. 4A shows that there was no significant difference in Galectin-3 protein in the serum of 4-week old $dy^W$–/– mice when compared to wild-type animals. FIG. 4B shows that there was no difference in Galectin-3 protein in $dy^W$–/– mice serum at 4- and 8-weeks of age.

FIG. 6A shows the transcript for Lgals1 (Galectin-1) is significantly increased over wild-type in both the 5- and 10-week old animals. FIG. 6B illustrates the transcript for Lgals3 (Galectin-3) was significantly increased over wild-type in both 5- and 10-week old animals.

FIG. 7A indicates no significant difference was observed in Galectin-1 protein in the muscles of 5-week old mdx mice when compared to wild-type animals. FIG. 7B illustrates that the level of Galectin-1 protein in the gastrocnemius muscle of 5-week old mdx animals compared to wild-type were not significantly different. FIG. 7C. shows there was no difference between Galectin-1 protein in the mdx mice at 2- and 5-weeks of age. There was a significant difference between the 2- and 10-week old mice and the 5- and 10-week old mice.

FIG. 8A shows a significant difference in Galectin-3 protein in the muscles of 5-week old mdx mice when compared to wild-type animals. FIG. 8B indicates that the level of Galectin-3 protein in the gastrocnemius muscle of 5- and 10-weeks of age mdx and wild-type mice and demonstrates that Galectin-3 protein in 10-week old mdx animals was significantly greater than Galectin-3 levels in 5-week old mdx animals.

FIG. 9A shows there was no significant difference in Galectin-3 protein in the serum of 5-week old mdx mice when compared to wild-type animals. FIG. 9B indicates there was no significant difference in Galectin-3 protein between 10-week old mdx mice serum and age-matched wild-type serum.

FIG. 14 is a graph, table and digital image illustrating Galectin-1 treatment increases α7 integrin.

FIGS. 15A-15D demonstrate Galectin-1 treatment of myoblasts and myotubes leads to elevated levels of a7 and b1 Integrins at both the transcript and protein levels. FIG. 15A is a bar graph illustrating the effect of treating $a7^{+/bGal}$ myoblasts with increasing levels of recombinant Galectin-1 and then examining for an increase in β-Galactosidase activity (a reporter for ITGA7 expression levels) using an FDG activity assay. FIG. 15B is a bar graph illustrating the effect of treating C2C12 myoblasts with Galectin-1 or PBS and then examining for levels of α7 Integrin protein relative to GAPDH levels, quantitated and graphed. FIG. 15C is a bar graph illustrating the effect of treating C2C12 myoblasts with Galectin-1 or PBS and then examining for levels of β1 Integrin protein levels relative to Ponceau S stain, quantitated and graphed. FIG. 15D is a bar graph illustrating the quantitative real-time PCR results for ITGA7, ITGB1, and LGALS1 levels from C2C12 myoblasts and myotubes treated with PBS or 0.2 mM recombinant Galectin-1.

FIGS. 16A-16D are bar graphs illustrating intermuscular (IM) injections of mdx mouse tibialus anterior (TA) muscles with recombinant Galectin-1 reduces muscle damage and the need for regeneration as determined by the histological appearance of centrally located nuclei (CLN). Mdx mouse TA muscles were IM injected with 20 ng (FIGS. 16A and 16B), 1.5 mg (FIG. 16C), or 150 mg (FIG. 16D) of recombinant Galectin-1 protein at 4, 3, 5, and 5 weeks old, respectively. Tissues were dissected 48 hours post-injection, cryosectioned, stained using standard hemotoxylin and eosin procedures and analyzed for CLN. Significance was calculated by student t-test (ns=no significance, *p<0.05).

FIGS. 19A-19D are graphs illustrating galectin-1 treatment of mdx mice increases relative strength, decreases fatigue, and normalizes muscle histological fiber size. (FIG. 19A) Grip strength studies on mdx mice treated weekly by intraperitoneal injections of PBS or 5 mg/kg recombinant Galectin-1 or untreated black-10 mice were performed using standard procedures. Average strength per gram body weight (FIG. 19B) and percent fatigue (FIG. 19C) were then calculated and graphed. (FIG. 19D) The TA was cryosectioned into 10 mM sections and fiber sizes were determined using the minimum Feret's diameter measurement on H&E stained sections, Feret's diameter for at least 1000 fibers per group were measured. Significance was calculated by student t-test (*p<0.05, p<0.01, *p<0.001).

DETAILED DESCRIPTION OF SEVERAL EMBODIMENTS

I. Overview of Several Embodiments

Figure 1A:
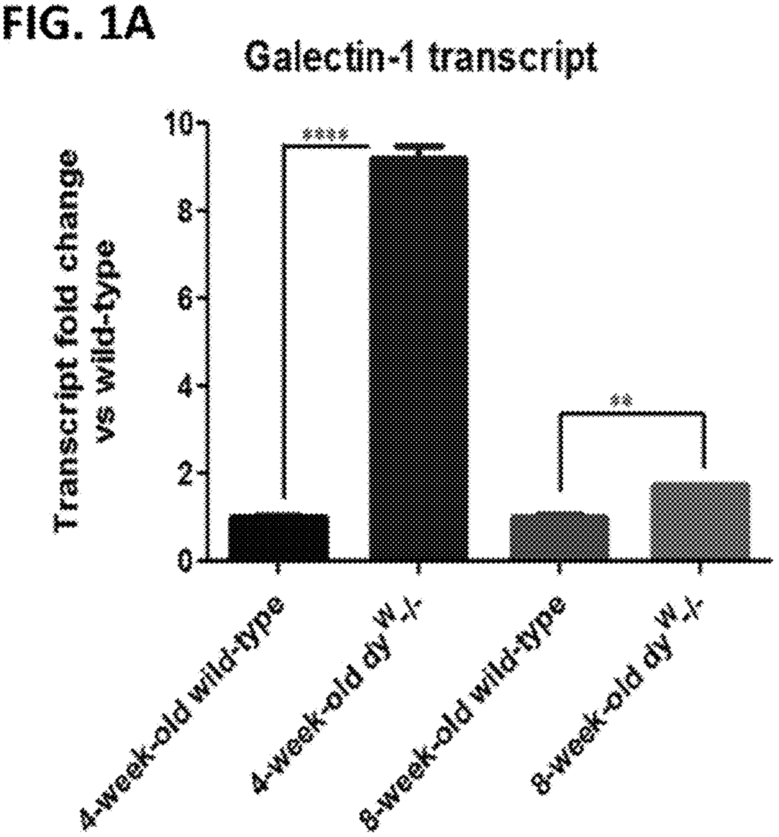
FIGS. 1A and 1B are bar graphs illustrating transcription of Lgals1 and Lgals3 are altered in the $dy^W$–/– mouse.

Disclosed herein are muscular dystrophy-associated molecules that can be used as biomarkers to diagnose and/or prognose muscular dystrophy, including DMD, LGMD, FHMD, Beckers muscular dystrophy and/or MDC1A. In some embodiments, the muscular dystrophy-associated molecules can include, consist essentially of, or consist of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) or any combination thereof. In some examples, muscular dystrophy-associated molecules include Galectin-1, Galectin-3, Col6A1, Itga3, Iga6, Itga7, Tnc and Timp 1. In some examples, muscular dystrophy-associated molecules include Galectin-1 and Galectin-3. In some examples, muscular dystrophy-associated molecules include Galectin-3 and Tnc. In some examples, the muscular dystrophy-associated molecules include at least Galectin-3 for detecting DMD, LGMD, FHMD, Beckers muscular dystrophy or MDC1A. In some examples, the muscular dystrophy-associated molecules include at least Galectin-3 for detecting DMD.

Disclosed herein are methods of diagnosing or prognosing a subject with muscular dystrophy. In some embodiments, a method of diagnosing or prognosing a subject with muscular dystrophy, comprises detecting expression of one or more of the disclosed muscular dystrophy-associated molecules, such as Galectin-1 or Galectin-3, in a sample obtained from the subject at risk of having or having one or more signs or symptoms associated with muscular dystrophy, thereby diagnosing or prognosing the subject with muscular dystrophy.

In some embodiments, a method of diagnosing or prognosing a subject with muscular dystrophy, comprises detecting expression of Galectin-1 or Galectin-3 in a sample obtained from the subject at risk of having or having one or more signs or symptoms associated with muscular dystrophy, thereby diagnosing or prognosing the subject with muscular dystrophy. In some embodiments, the method further comprises comparing expression of Galectin-1 or Galectin-3 in the sample obtained from the subject at risk of having or having one or more signs or symptoms associated with muscular dystrophy to a control, wherein increased expression of Galectin-1 or Galectin-3 molecules relative to a control indicates that the subject has muscular dystrophy.

In some embodiments, the muscular dystrophy is MDC1A, LGMD, FHMD, Beckers muscular dystrophy or DMD.

In some embodiments, detecting expression comprises detecting Galectin-3 and/or Galectin-1.

In some embodiments, increased expression of Galectin-3 molecules relative to a control indicates that the subject has a poor prognosis and a decreased chance of survival.

In some embodiments, the muscular dystrophy is DMD.

In some embodiments, the sample is a blood or urine sample.

In some embodiments, expression is measured by real time quantitative polymerase chain reaction, microarray analysis or Western blot analysis.

In some embodiments, methods of treating muscular dystrophy in a subject are disclosed. In some embodiments, the method comprises administering to the subject with muscular dystrophy an effective amount of an agent that alters expression or biological activity of Galectin-3, thereby treating one or more signs or symptoms associated with muscular dystrophy increasing the subject's chance of survival. In some embodiments, the agent reduces the biological activity of Galectin-3. In some embodiments, the agent increases the biological activity of Galectin-3.

In some embodiments, methods of treating muscular dystrophy in a subject are disclosed. In some embodiments, the method comprises administering to the subject with muscular dystrophy an effective amount of an agent that increases expression or biological activity of Galectin-1, thereby treating one or more signs or symptoms associated with muscular dystrophy increasing the subject's chance of survival. In some embodiments, the agent increases the biological activity of Galectin-1.

In some embodiments, methods of treating a subject with galectin or a composition that includes galectin are also disclosed. For example, some embodiments provide methods of improving muscular health, such as enhancing muscle regeneration, maintenance, or repair in a subject by administering to the subject an effective amount of galectin or a composition comprising galectin, including fragments, derivatives, or analogs thereof. In a specific example, the galectin is a complete galectin protein. In further examples, the galectin is selected from Galectin-1, Galectin-3, and combinations thereof. In further examples, the galectin or galectin composition includes a substance at least substantially homologous to Galectin-1 or Galectin-3. In yet further implementations, the galectin or galectin composition comprises a polypeptide at least substantially homologous to the Galectin-1 or Galectin-3.

In some embodiments, methods of increasing/maintaining muscle strength and/or bone density are provided. Also disclosed herein are methods of preventing, inhibiting and/or reducing muscle and/or bone loss. In some examples, a galectin composition, such as galectin-1 composition, is administered to increase muscle strength and/or bone density and/or prevent, inhibit or slow muscle and bone loss. In some examples, a galectin composition, such as galectin-1 composition, is administered to a subject at risk of muscle/bone injury or muscle/bone loss, such as to an athlete, an astronaut, or any other individual that partakes in activities that may cause muscle/bone injury and/or loss. In some examples, a disclosed regimen, such as a disclosed Galectin-1 regimen, is provided to prevent muscle/bone injury and/or loss. In some examples, a disclosed regimen, such as a disclosed Galectin-1 regimen, is provided to maintain bone density and/or muscle strength. In some examples, a disclosed regimen, such as a disclosed Galectin-1 regimen, is provided to treat a subject experiencing a loss in bone density and/or muscle strength whereby the regimen is administered in a manner to lead to an increase in bone density and/or muscle strength or to maintain the existing muscle strength and bone density (e.g., prevent further loss of muscle strength and/or bone density).

In some examples, a galectin composition, such as a Galectin-1 composition, is administered to a subject at risk of acquiring or suffering from a condition or disease associated with muscle loss, bone loss, muscle density loss, and/or muscle strength loss, such as, but not limited to a subject at risk of acquiring or suffering from kyphosis, muscular dystrophies, broken bones, muscle strains, muscle tears, tendon injury, osteoporosis, rheumatoid arthritis, lupus, scoliosis, and/or multiple sclerosis. In some examples, a galectin composition, such as a Galectin-1 composition, is administered for preventing, treating or slowing the progression of a sign or symptom associated with aging. It is contemplated that a galectin composition can be administered for short or prolong periods of time, ranging from days to years. In some examples, a galectin composition, such as Galectin-1, is administered post-surgery, such as to a subject that has undergone surgery and may be at risk of experiencing or has muscle loss, bone loss, muscle strength loss or muscle density loss. In some examples, a galectin composition, such as Galectin-1, is administered to a female subject post-pregnancy. In some examples, a galectin composition, such as Galectin-1, is administered to a short or long-term coma subject.

II. Terms

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administration: To provide or give a subject an agent by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes. For example, Galectin, or compositions thereof, also may be administered to a subject using a combination of these techniques.

Suitable solid or liquid pharmaceutical preparation forms are, for example, aerosols, (micro)capsules, creams, drops, drops or injectable solution in ampoule form, emulsions, granules, powders, suppositories, suspensions, syrups, tablets, coated tablets, and also preparations with protracted release of active compounds, in whose preparation excipients and additives and/or auxiliaries such as binders, coating agents, disintegrants, flavorings, lubricants, solubilizers, sweeteners, or swelling agents are customarily used as described above. The pharmaceutical compositions are suitable for use in a variety of drug delivery systems. For a brief review of various methods for drug delivery, see Langer, "New Methods of Drug Delivery," *Science* 249:1527-1533 (1990), incorporated by reference herein to the extent not inconsistent with the present disclosure.

Galectin, such as Galectin-1, Galectin-3 or the disclosed compositions or other therapeutic or nutraceutical agents of the present disclosure can be formulated into active pharmaceutical or nutraceutical compositions that can be administered to a subject parenterally or orally. Parenteral administration routes include, but are not limited to epidermal, intraarterial, intramuscular (IM, and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

Galectin, such as Galectin-1, Galectin-3 or the disclosed compositions or other therapeutic or nutraceutical agent can be mixed or combined with suitable pharmaceutically acceptable excipients to prepare pharmaceutical compositions. Pharmaceutically acceptable excipients/carriers include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example. Liposomal suspensions may also be suitable as pharmaceutically acceptable carriers.

Upon mixing or addition of a disclosed composition, or other therapeutic agent, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier.

Pharmaceutical carriers suitable for administration of galectin, such as Galectin-1, Galectin-3 or the disclosed compositions or other therapeutic agent include any such carriers known to be suitable for the particular mode of administration. In addition, galectin, such as Galectin-1, Galectin-3 or the disclosed composition or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, Del.).

Galectin, such as Galectin-1, Galectin-3 or the disclosed compositions or other therapeutic agent can be prepared with carriers that protect them against rapid elimination from the body, such as coatings or time-release formulations. Such carriers include controlled release formulations, such as, but not limited to, microencapsulated delivery systems. The galectin, such as Galectin-1, Galectin-3 or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, mouse models of muscular dystrophy may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates; chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

For topical application, galectin, such as Galectin-1, Galectin-3 or the disclosed compositions or other therapeutic agent may be made up into a cream, lotion, ointment, solution, or suspension in a suitable aqueous or non-aqueous carrier. Topical application can also be accomplished by transdermal patches or bandages which include the therapeutic substance. Additives can also be included, e.g., buffers such as sodium metabisulphite or disodium edetate; preservatives such as bactericidal and fungicidal agents, including phenyl mercuric acetate or nitrate, benzalkonium chloride, or chlorhexidine; and thickening agents, such as hypromellose.

If galectin, such as Galectin-1, Galectin-3 or a disclosed composition or other therapeutic agent is administered orally as a suspension, the pharmaceutical compositions can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/flavoring agents. Oral liquid preparations can contain conventional additives such as suspending agents, e.g., gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these compositions can contain dicalcium phosphate, lactose, magnesium stearate, microcrystalline cellulose, and starch and/or other binders, diluents, disintegrants, excipients, extenders, and lubricants.

If oral administration is desired, the galectin, such as Galectin-1, Galectin-3 or a disclosed composition, or other therapeutic substance can be provided in a composition that protects it from the acidic environment of the stomach. For example, Galectin-1, Galectin-3 or a disclosed composition, or other therapeutic agent can be formulated with an enteric coating that maintains its integrity in the stomach and releases the active compound in the intestine. The Galectin-1, Galectin-3 or a disclosed composition, or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, the galectin, such as Galectin-1, Galectin-3, or disclosed composition, or other therapeutic substance can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. The galectin, such as Galectin-1, Galectin-3 or disclosed composition, or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need to be administered less frequently.

Agent: Any protein, nucleic acid molecule (including chemically modified nucleic acids), compound, antibody, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including treating a subject with a muscular dystrophy).

In some examples, an agent can act directly or indirectly to alter the activity of Galectin-1 and/or Galectin-3. An example of a therapeutic agent is one that can alter the activity of a gene or gene product associated with muscular dystrophy, for example as measured by a clinical response (such as an increase survival time or a decrease in one or more signs or symptoms associated with the muscular dystrophy). Therapeutically agents also include organic or other chemical compounds that mimic the effects of the therapeutically effective peptide, antibody, or nucleic acid molecule.

A "pharmaceutical agent" is a chemical compound or composition capable of inducing a desired therapeutic or prophylactic effect when administered to a subject, alone or in combination with another therapeutic agent(s) or pharmaceutically acceptable carriers. In a particular example, a pharmaceutical agent significantly reduces the expression and/or activity of a muscular dystrophy associated molecule thereby increasing a subject's survival time.

Antibody: A polypeptide including at least a light chain or heavy chain immunoglobulin variable region which specifically recognizes and binds an epitope of an antigen, such as a muscular dystrophy-associated molecule or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for a muscular dystrophy-associated molecule, such as Galectin-1 or Galectin-3.

The term antibody includes intact immunoglobulins, as well the variants and portions thereof, such as Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds a muscular dystrophy-associated molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are ly identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Alteration or modulation in expression: An alteration in expression of a gene, gene product or modulator thereof, such as one or more muscular dystrophy associated molecules disclosed herein, refers to a change or difference, such as an increase or decrease, in the level of the gene, gene product, or modulators thereof that is detectable in a biological sample (such as a sample from a subject at risk or having muscular dystrophy) relative to a control (such as a sample from a subject without a muscular dystrophy) or a reference value known to be indicative of the level of the gene, gene product or modulator thereof in the absence of the disease. An "alteration" in expression includes an increase in expression (up-regulation) or a decrease in expression (downregulation).

Analog: A compound which is sufficiently homologous to a compound such that it has a similar functional activity for a desired purpose as the original compound. Analogs include polypeptides having one or more amino acid substitutions compared with a particular substance.

At least substantially homologous: A phrase used in the present disclosure, refers to a degree of homology sufficient to produce at least a portion of the activity of a reference material in muscle regeneration, maintenance or repair, or wound healing. In some examples, materials are at least substantially homologous when they are at least about 95%, at least about 98%, or at least about 99% homologous to a reference material.

Biological activity: The beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, the agent significantly reduces the biological activity of the one or more muscular dystrophy associated molecules disclosed herein which reduces one or more signs or symptoms associated with the muscular dystrophy.

Biomarkers: Natural substances produced by the body that are used as indicators of specific biological states. Biomarkers allow conditions, including diseases to be diagnosed, progression of such monitored, as well as to test the efficacy of disease treatments. The muscular dystrophies are one group of diseases with a lack of biomarkers. Serum creatine kinase (a byproduct of muscle breakdown) levels have previously been used as a biomarker for muscular dystrophy but do not accurately follow the progression of the disease. Disclosed herein are biomarkers for muscular dystrophy. In particular examples, the biomarker indicates a particular type of muscular dystrophy to be present or the severity of the condition (e.g., an increase in the level of Galectin-3 indicates a poor prognosis).

Bone density: A term referring to the amount of mineral matter per square centimeter of bones. Bone density is used in clinical medicine as an indirect indicator for various conditions and diseases, including, but not limited to, osteoporosis and fracture risk. Many techniques are available to determine bone density, but ultrasound has been described as a more cost-effective approach. The test works by measuring a specific bone or bones, usually the spine, hip, and wrist. The density of these bones is then compared with an average index based on age, sex, and size. The resulting comparison is used to determine risk for fractures and the stage of osteoporosis in an individual. Average bone mineral density=BMC/W [g/cm2]; BMC=bone mineral content=g/cm; and W=width at the scanned line. Results are generally scored by two measures, the T-score and the Z-score. Scores indicate the amount one's bone mineral density varies from the mean. Negative scores indicate lower bone density, and positive scores indicate higher.

The T-score is the relevant measure when screening for osteoporosis. It is the bone mineral density at the site when compared to the young normal reference mean. It is a comparison of a patient's BMD to that of a healthy thirty-year-old. The US standard is to use data for a thirty-year-old of the same sex and ethnicity, but the WHO recommends using data for a thirty-year-old white female for everyone. Values for thirty-year-olds are used in post-menopausal women and men over age 50 because they better predict risk of future fracture. The criteria of the World Health Organization are: Normal is a T-score of −1.0 or higher; Osteopenia is defined as between −1.0 and −2.5; and Osteoporosis is defined as −2.5 or lower, meaning a bone density that is two and a half standard deviations below the mean of a thirty-year-old man/woman.

The Z-score is the comparison to the age-matched normal and is usually used in cases of severe osteoporosis. This is the number of standard deviations a subject's BMD differs from the average BMD of their age, sex, and ethnicity. This value is used in premenopausal women, men under the age of 50, and in children. It is most useful when the score is less than 2 standard deviations below this normal. In this setting, it is helpful to scrutinize for coexisting illnesses that may contribute to osteoporosis such as glucocorticoid therapy, hyperparathyroidism, or alcoholism.

Contacting: Placement in direct physical association, including both a solid and liquid form. Contacting an agent with a cell can occur in vitro by adding the agent to isolated cells or in vivo by administering the agent to a subject.

Control: A sample or standard used for comparison with a test sample, such as a biological sample obtained from a patient (or plurality of patients) without a particular disease or condition, such as a muscular dystrophy. In some embodiments, the control is a sample obtained from a healthy patient (or plurality of patients) (also referred to herein as a "normal" control), such as a normal biological sample. In some embodiments, the control is a historical control or standard value (e.g., a previously tested control sample or group of samples that represent baseline or normal values (e.g., expression values), such as baseline or normal values of a particular gene, gene product in a subject without a muscular dystrophy). In some examples, the control is a standard value representing the average value (or average range of values) obtained from a plurality of patient samples (such as an average value or range of values of the gene or gene products in the subjects without a muscular dystrophy).

Decrease: To reduce the quality, amount, or strength of something. In one example, a therapy decreases one or more symptoms associated with the muscular dystrophy, for example as compared to the response in the absence of the therapy. In a particular example, a therapy decreases (also known as down-regulates) the expression of a muscular dystrophy-associated molecule, such as a decrease of at least 10%, at least 20%, at least 50%, or even at least 90%, thereby increasing a subject's chance of survival. In some examples, a decrease in expression refers to any process which results in a decrease in production of one or more molecules associated with muscular dystrophy. A gene product can be RNA (such as mRNA, rRNA, tRNA, and structural RNA) or protein, Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression or protein expression in a biological sample taken from a subject who does not have muscular dystrophy, such as DMD or MDC1A. Such decreases can be measured using the methods disclosed herein. For example, "detecting or measuring expression of a gene product" includes quantifying the amount of the gene, gene product or modulator thereof present in a sample. Quantification can be either numerical or relative. Detecting expression of the gene, gene product or modulators thereof can be achieved using any method known in the art or described herein, such as by measuring nucleic acids by PCR (such as RT-PCR) and proteins by ELISA. In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have muscular dystrophy, such as DMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

The level of expression in either a qualitative or quantitative manner can detect nucleic acid or protein. Exemplary methods include microarray analysis, RT-PCR, Northern blot, Western blot, and mass spectrometry.

Derivative: A form of a substance, such as a galectin or portion thereof, which has at least one functional group altered, added, or removed, compared with the parent compound.

Diagnosis: The process of identifying a disease, such as muscular dystrophy, by its signs, symptoms and results of various tests. The conclusion reached through that process is also called "a diagnosis." Forms of testing commonly performed include blood tests, medical imaging, urinalysis, and biopsy.

Effective amount: An amount of agent that is sufficient to generate a desired response, such as reducing or inhibiting one or more signs or symptoms associated with a condition or disease. When administered to a subject, a dosage will generally be used that will achieve target tissue/cell concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example anti-pathogenic agents), induces the desired response such as treatment of a muscular dystrophy, such as DMD, LGMD, FHMD, Beckers muscular dystrophy or MDC1A.

In particular examples, it is an amount of an agent capable of modulating one or more of the disclosed genes, gene products or modulators thereof associated with a muscular dystrophy by least 20%, at least 50%, at least 60%, at least 70%, at least 80%, at least 90%, at least 95%, at least 98%, or even at least 100% (elimination of the disease to a point beyond detection) by the agent.

In some examples, an effective amount is an amount of a pharmaceutical preparation that alone, or together with a pharmaceutically acceptable carrier or one or more additional therapeutic agents, induces the desired response.

In one example, a desired response is to increase the subject's survival time by slowing the progression of the disease. The disease does not need to be completely inhibited for the pharmaceutical preparation to be effective. For example, a pharmaceutical preparation can decrease the progression of the disease by a desired amount, for example by at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the muscular dystrophy within the subject. Treatment can involve only slowing the progression of the disease temporarily, but can also include halting or reversing the progression of the disease permanently.

Effective amounts of the agents described herein can be determined in many different ways, such as assaying for a reduction in of one or more signs or symptoms associated with the muscular dystrophy in the subject or measuring the expression level of one or more molecules known to be associated with the muscular dystrophy. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied (for example a nucleic acid molecule isolated from a cellular extract versus a chemically synthesized and purified nucleic acid), the subject being treated, the severity and type of the condition being treated, and the manner of administration.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to diagnosis and/or prognosis a subject with muscular dystrophy, such as predict a subject's survival time with DMD, LGMD or MDC1A.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have muscular dystrophy, such as DMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Extracellular matrix: The extracellular structure of a tissue or a layer thereof, including the arrangement, composition, and forms of one or more matrix components, such as proteins, including structural proteins such as collagen and elastin, proteins such as fibronectin and laminins, and proteoglycans. The matrix may comprise fibrillic collagen, having a network of fibers. In some examples, the extracellular matrix is connected to cells through the costameric protein network.

Fragment: A portion of a substance, such as galectin. A fragment may be, in some examples, a particular domain or chain of a protein. For example, particular embodiments of the present disclosure involve administering a fragment of galectin, such as a fragment of Galectin-1 or Galectin-3. Fragments may be synthetic or may be derived from larger parent substances.

Functional group: A radical, other than a hydrocarbon radical, that adds a physical or chemical property to a substance.

Galectins: β-galactoside-binding animal lectins that modulate extracellular matrix interactions, cell attachment and differentiation, as well as cancer invasion and metastasis, Fifteen mammalian galectins have been identified thus far, with Galectin-1 and Galectin-3 being two of the most well characterized. Galectin-1 is encoded by the Lgals1 gene, located on chromosome 22q12. Galectin-1, approximately 15 kDa in size, binds to a number of extracellular matrix components, such as laminin, as well as with several integrins, including the α7β1 integrin. It is present both intracellularly and extracellularly and has been shown to play a role in immunosupression, cell-growth regulation, cell apoptosis and pre-mRNA slicing. Galectin-1 is found in skeletal muscle and has been implicated in the conversion of dermal fibroblasts to muscle due to its competition with laminin for α7β1 integrin binding.

Galectin-3, about 30 kDa in size, is encoded by the Lgals3 gene, located on chromosome 14q22. This protein has a carboxyl-terminal domain that binds carbohydrates and an amino terminal domain that cross-links carbohydrate and noncarbohydrate ligands. Similar to Galectin-1, Galectin-3 is also found both intracellularly and extracellularly. Intracellularly, Galectin-3 has been shown to regulate the cell cycle and apoptosis. Extracellularly, Galectin-3 works to mediate cell-cell interactions as well as cell-extracellular matrix interactions. Galectin-3 is also expressed and secreted by macrophages and monocytes. Galectin-3 is specifically upregulated during monocyte differentiation, and downregulated during differentiation into dendritic cells.

In some examples, expression of Galectin-1 is increased in a subject with muscular dystrophy, such as with DMD, MDC1A, FHMD, Beckers muscular dystrophy or LGMD. The term Galectin-1 includes any Galectin-1 gene, cDNA, mRNA, or protein from any organism and that is Galectin-1 and is expressed in a sample from a subject with muscular dystrophy such as DMD, LGMD, FHMD, Beckers muscular dystrophy or MDC1A.

In some examples, expression of Galectin-3 is increased in a subject with muscular dystrophy, such as with DMD, MDC1A, FHMD, Beckers muscular dystrophy or LGMD. The term Galectin-3 includes any Galectin-3 gene, cDNA, mRNA, or protein from any organism and that is Galectin-3 and is expressed in a sample from a subject with muscular dystrophy such as DMD, LGMD, FHMD, Beckers muscular dystrophy or MDC1A.

Nucleic acid and protein sequences for Galectin-1 and Galectin-3 are publicly available. For example, GENBANK® Accession Nos: NM_002306; NM_003225; NM_00177388 disclose Galectin-1 nucleic acid sequences, and GENBANK® Accession No.: NP_002296 discloses a Galectin-1 protein sequence, all of which are incorporated by reference as provided by GENBANK® on Aug. 11, 2011; GENBANK® Accession No. NP_032521.1 also provides a Galectin-1 protein sequence which is incorporated by reference in its entirety as provided by GENBANK® on Aug. 10, 2012.

GENBANK® Accession Nos: NM_001177388; NM_002306; NP_003225 disclose Galectin-3 nucleic acid sequences, and GENBANK® Accession Nos.:_BA22164 discloses a Galectin-3 protein sequence, all of which are incorporated by reference as provided by GENBANK® on Aug. 11, 2011; GENBANK® Accession No. NP_034835.1 also provides a Galectin-3 protein sequence which is incorporated by reference in its entirety as provided by GENBANK® on Aug. 10, 2012.

In one example, Galectin-1 includes a full-length wild-type (or native) sequence, as well as Galectin-1 allelic variants, fragments, homologs or fusion sequences, such as Galectin-1 allelic variants, fragments, homologs or fusion sequences that retain the ability to increase α7 integrin expression or biological activity. In certain examples, Galectin-1 has at least 80% sequence identity, for example at least 85%, 90%, 95%, or 98% sequence identity to Galectin-1.

In one example, Galectin-3 includes a full-length wild-type (or native) sequence, as well as Galectin-3 allelic variants, fragments, homologs or fusion sequences, such as Galectin-3 allelic variants, fragments, homologs or fusion sequences that retain the ability to increase α7 integrin expression or biological activity. In certain examples, Galectin-3 has at least 80% sequence identity, for example at least 85%, 90%, 95%, or 98% sequence identity to Galectin-3.

Improving muscular health: An improvement in muscular health compared with a preexisting state or compared with a state which would occur in the absence of treatment. For example, improving muscular health may include enhancing muscle regeneration, maintenance, or repair. Improving muscular health may also include prospectively treating a subject to prevent or reduce muscular damage or injury.

Inhibiting a disease or condition: A phrase referring to inhibiting the development of a disease or condition, such as reducing, decreasing or delaying a sign or symptom associated with the disease or condition, for example, in a subject who is at risk of acquiring the disease/condition or has the particular disease/condition. Particular methods of the present disclosure provide methods for inhibiting muscular dystrophy.

Kyphosis: A condition of over-curvature of the thoracic vertebrae (upper back). It can be either the result of degenerative diseases (such as arthritis), developmental problems (the most common example being Scheuermann's disease), osteoporosis with compression fractures of the vertebrae, or trauma. In the sense of a deformity, it is the pathological curving of the spine, where parts of the spinal column lose some or all of their lordotic profile. This causes a bowing of the back, seen as a slouching posture. The Cobb angle is the preferred method of measuring kyphosis.

Label: An agent capable of detection, for example by ELISA, spectrophotometry, flow cytometry, or microscopy. For example, a label can be attached to a nucleic acid molecule or protein (such as Galectin-1 or Galectin-3), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998). In a particular example, a label is conjugated to an agent that binds to one or more of the muscular dystrophy associated molecules, such as Galectin-1 or Galectin-3, to allow for the detection and prognosis of the disease in a subject.

Lupus erythematosus: A term referring to a collection of autoimmune diseases, in which the human immune system becomes hyperactive and attacks normal, healthy tissues. Symptoms of these diseases can affect many different body systems, including joints, skin, kidneys, blood cells, heart, and lungs. Maintenance of cells or tissue: A phrase refers to maintaining cells or tissue, such as muscle cells or muscle tissue, in at least substantially the same physiological condition, such as maintaining such condition even in the presence of stimulus which would normally cause damage, injury, or disease.

Multiple sclerosis: An autoimmune disease classically described as a central nervous system white matter disorder disseminated in time and space that presents as relapsing-remitting illness in 80-85% of patients, Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesions, hypointensive "black holes" (representing gliosis and axonal pathology), and brain atrophy on T1-weighted studies. Serial MRI studies can be used to indicate disease progression. Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form.

Muscle: Any myoblast, myocyte, myofiber, myotube or other structure composed of muscle cells. Muscles or myocytes can be skeletal, smooth, or cardiac. Muscle may also refer to, in particular implementations of the present disclosure, cells or other materials capable of forming myocytes, such as stem cells and satellite cells.

Muscle density: A term referring to the rigidity ("hardness") of a muscle during a resting state. Muscular density is also referred to as muscle tone (e.g., the continuous and passive partial contraction of the muscles, or the muscle's resistance to passive stretch during resting state).

Muscle strength: The amount of force a muscle can produce with a single maximal effort.

Muscular dystrophy: A term used to refer to a group of genetic disorders that lead to progressive muscle weakness. Muscular dystrophy can result in skeletal muscle weakness and defects in skeletal muscle proteins, leading to a variety of impaired physiological functions. No satisfactory treatment of muscular dystrophy exists. Existing treatments typically focus on ameliorating the effects of the disease and improving the patient's quality of life, such as through physical therapy or through the provision of orthopedic devices.

Mutated genes associated with muscular dystrophy are responsible for encoding a number of proteins associated with the costameric protein network. Such proteins include laminin-2, collagen, dystroglycan, integrins, caveolin-3, ankyrin, dystrophin, α-dystrobrevin, vinculin, plectin, BPAG1b, muscle LIM protein, desmin, actinin-associated LIM protein, α-actin, titin, telethonin, cypher, myotilin, and the sarcoglycan/sarcospan complex.

The most common form of muscular dystrophy is Duchenne muscular dystrophy (DMD), affecting 1 in 3,500 live male births. DMD is an X-linked recessive disorder characterized by a mutation in the gene that codes for dystrophin. Dystrophin is a cytoskeletal protein about 430 kDa in size. This protein works to connect the cell's cytoskeleton and extracellular matrix. The loss of dystrophin in DMD patients leads to a loss of muscle fiber attachment at the extracellular matrix during contraction, which ultimately leads to progressive fiber damage, membrane leakage and a loss of muscle function. Most patients die before they reach the age of 30 due to respiratory or cardiac failure.

Beckers muscular dystrophy (also known as Benign pseudohypertrophic muscular dystrophy) is related to Duchenne muscular dystrophy in that both result from a mutation in the dystrophin gene, but in Duchenne muscular dystrophy no functional dystrophin is produced making DMD much more severe than BMD. BMD is an X-linked recessive inherited disorder characterized by slowly progressive muscle weakness of the legs and pelvis. BMD is a type of dystrophinopathy, which includes a spectrum of muscle diseases in which there is insufficient dystrophin produced in the muscle cells, results in instability in the structure of muscle cell membrane. This is caused by mutations in the dystrophin gene, which encodes the protein dystrophin. The pattern of symptom development of BMD is similar to DMD, but with a later, and much slower rate of progression.

Congenital muscular dystrophies are caused by gene mutations affecting the production of other costameric proteins. MDC1A is a congential muscular dystrophy due to a genetic mutation in the LAMA2 gene which results in lack of or complete loss of laminin-$\alpha 2$ protein. This loss of laminin-$\alpha 2$ leads to an absence of laminins-211/221. Laminins-211/221 are major components of the extracellular matrix and play a key role in muscle cell development. During muscle cell differentiation laminin binds to the $\alpha 7\beta 1$ integrin. Without laminin-$\alpha 2$, muscle fibers are unable to adhere to the basement membrane and myotubes undergo apotosis. Muscle regeneration also fails, leading to a loss of muscle repair and an increase in muscle fibrosis and inflammation. This chronic tissue injury is a major cause of morbidity and mortality in MDC1A.

Congenital Muscular Dystrophies (CMD) and Limb-Girdle muscular dystrophy (LGMD) are common forms of highly heterogeneous muscular dystrophies which can be distinguished by their age at onset. In CMD, onset of symptoms is at birth or within the first 6 months of life; in LGMD onset of symptoms is in late childhood, adolescence or even adult life. Inheritance in LGMD can be autosomal dominant (LGMD type 1) or autosomal recessive (LGMD type 2), CMD is recessively inherited. CMD and LGMD can overlap both clinically and genetically MDC1A is a progressive muscle wasting disease that results in children being confined to a wheelchair, requiring ventilator assistance to breathe and premature death. Symptoms are detected at birth with poor muscle tone and "floppy" baby syndrome. DMD, BMD and LGMD are progressive muscle degenerative diseases usually diagnosed at 3-5 years of age when children show developmental delay including ability to walk and climb stairs. The disease is progressive and children are usually confined to a wheelchair in their teens and require ventilator assistance.

Facioscapulohumeral muscular dystrophy (FHMD) is a form of muscular dystrophy associated with progressive muscle weakness and loss of muscle tissue. Unlike DMD and BMD which mainly affect the lower body, FHMD affects the upper body mainly the face, shoulder and upper arm muscles. However, it can affect muscles around the pelvis, hips, and lower leg. Symptoms for FHMD often do not appear until age 10-26, but it is not uncommon for symptoms to appear much later. In some cases, symptoms never develop. Symptoms are usually mild and very slowly become worse. Facial muscle weakness is common, and may include eyelid drooping, inability to whistle, decreased facial expression, depressed or angry facial expression, difficulty pronouncing words, shoulder muscle weakness (leading to deformities such as pronounced shoulder blades (scapular winging) and sloping shoulders), weakness of the lower, hearing loss and possible heart conditions.

Muscular dystrophy-associated molecule: A molecule whose expression or biological activity is altered in subject with muscular dystrophy. Such molecules include, for instance, nucleic acid sequences (such as DNA, cDNA, or mRNAs) and proteins. Specific genes include those disclosed herein, including the Examples, as well as fragments of the full-length genes, cDNAs, or mRNAs (and proteins encoded thereby) whose expression is altered (such as upregulated or downregulated) in response to muscular dystrophy, including DMD, LGMD, FHMD, Beckers muscular dystrophy and/or MDC1A. Thus, the presence or absence of the respective muscular dystrophy-associated molecules can be used to diagnose and/or determine the prognosis of a muscular dystrophy, and in particular DMD, LGMD, FHMD, Beckers muscular dystrophy or MDC1A in a subject as well as to treat a subject with a muscular dystrophy, such as DMD, LGMD, FHMD, Beckers muscular dystrophy or MDC1A. In some examples, it is a molecule associated with one or more signs or symptoms of a muscular dystrophy-associated condition or disease. In some examples, a muscular dystrophy-associated molecule is one or more molecules associated with DMD, LGMD, FHMD, Beckers muscular dystrophy and/or MDC1A, such as Galectin-1 or Galectin-3.

Osteoporosis: A progressive bone disease that's characterized by a decrease in bone mass and density and that leads to an increased risk of fracture. In osteoporosis, the bone mineral density (BMD) is reduced, bone microarchitecture deteriorates, and the amount and variety of proteins in bone are altered. Osteoporosis is defined by the World Health Organization (WHO) as a bone mineral density of 2.5 standard deviations or more below the mean peak bone mass (average of young, healthy adults) as measured by dual-energy X-ray absorptiometry; the term "established osteoporosis" includes the presence of a fragility fracture. The disease may be classified as primary type 1, primary type 2, or secondary.

The form of osteoporosis most common in women after menopause is referred to as primary type 1 or postmenopausal osteoporosis. Primary type 2 osteoporosis or senile osteoporosis occurs after age 75 and is seen in both females and males at a ratio of 2:1. Secondary osteoporosis may arise at any age and affect men and women equally. This form results from chronic predisposing medical problems or disease, or prolonged use of medications such as glucocorticoids, when the disease is called steroid- or glucocorticoid-induced osteoporosis.

Pharmaceutically acceptable carriers: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more therapeutic agents, such as one or more compositions that include a binding agent that specifically binds to at least one of the disclosed muscular dystrophy-associated molecules.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Polymerase Chain Reaction (PCR): An in vitro amplification technique that increases the number of copies of a nucleic acid molecule (for example, a nucleic acid molecule in a sample or specimen). In an example, a biological sample collected from a subject is contacted with a pair of oligonucleotide primers, under conditions that allow for the hybridization of the primers to nucleic acid template in the sample (such as those listed in Example 1 or 2). The primers are extended under suitable conditions, dissociated from the template, and then re-annealed, extended, and dissociated to amplify the number of copies of the nucleic acid. The product of a PCR can be characterized by electrophoresis, restriction endonuclease cleavage patterns, oligonucleotide hybridization or ligation, and/or nucleic acid sequencing, using standard techniques or other standard techniques known in the art.

Prognosis: A prediction of the course of a disease, such as muscular dystrophy. The prediction can include determining the likelihood of a subject to develop aggressive, recurrent disease, to survive a particular amount of time (e.g. determine the likelihood that a subject will survive 1, 2, 3 or 5 years), to respond to a particular therapy or combinations thereof.

Regeneration: The repair of cells or tissue, such as muscle cells or tissue (or organs) which includes muscle cells, following injury or damage to at least partially restore the muscle or tissue to a condition similar to which the cells or tissue existed before the injury or damage occurred. Regeneration also refers to facilitating repair of cells or tissue in a subject having a disease affecting such cells or tissue to eliminate or ameliorate the effects of the disease. In more specific examples, regeneration places the cells or tissue in the same condition or an improved physiological condition as before the injury or damage occurred or the condition which would exist in the absence of disease.

Repair of cells or tissue: A phrase which refers to the physiological process of healing damage to the cells or tissue such as muscle cells or tissue (or organs) following damage or other trauma.

Rheumatoid arthritis (RA): An autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated. The process involves an inflammatory response of the capsule around the joints (synovium) secondary to swelling (turgescence) of synovial cells, excess synovial fluid, and the development of fibrous tissue (pannus) in the synovium. The pathology of the disease process often leads to the destruction of articular cartilage and ankylosis (fusion) of the joints. RA can also produce diffuse inflammation in the lungs, the membrane around the heart (pericardium), the membranes of the lung (pleura), and white of the eye (sclera), and also nodular lesions, most common in subcutaneous tissue. RA is a clinical diagnosis made on the basis of symptoms, physical exam, radiographs (X-rays) and laboratory tests.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, surgical specimen, and autopsy material. In one example, a sample includes muscle biopsy, such as from a subject with DMD, LGMD, FHMD, Beckers muscular dystrophy or MDC1A.

Scoliosis: A condition in which a person's spine is curved from side to side. Although it is a complex three-dimensional deformity, on an X-ray, viewed from the rear, the spine of an individual with scoliosis can resemble an "S" or a "C", rather than a straight line. Scoliosis is typically classified as either congenital (caused by vertebral anomalies present at birth), idiopathic (cause unknown, subclassified as infantile, juvenile, adolescent, or adult, according to when onset occurred), or secondary to a primary condition. Scoliosis is defined as a spinal curvature of more than 10 degrees to the right or left as the examiner faces the subject (in the coronal plane). Deformity may also exist to the front or back (in the sagittal plane). The standard method for assessing the curvature quantitatively is measurement of the Cobb angle, which is the angle between two lines, drawn perpendicular to the upper endplate of the uppermost vertebra involved and the lower endplate of the lowest vertebra involved.

Signs or symptoms: Any subjective evidence of disease or of a subject's condition, e.g., such evidence as perceived by the subject; a noticeable change in a subject's condition indicative of some bodily or mental state, A "sign" is any abnormality indicative of disease, discoverable on examination or assessment of a subject. A sign is generally an objective indication of disease. Signs include, but are not limited to any measurable parameters such as tests for detecting muscular dystrophy, including measuring creatine kinase levels, electromyography (to determine if weakness is caused by destruction of muscle tissue rather than by damage to nerves) or immunohistochemistry/immunoblotting/immunoassay (e.g., ELISA) to measure muscular dystrophy-associated molecules. In one example, reducing or inhibiting one or more symptoms or signs associated with muscular dystrophy, includes reducing or inhibiting the activity or expression of one or more disclosed muscular dystrophy-associated molecules by a desired amount, for example by at least 20%, at least 50%, at least 60%, at least 70%, at least 80%, at least 90%, at least 95%, at least 98%, or even at least 100%, as compared to the activity and/or expression in the absence of the treatment. Symptoms of muscular dystrophy include, but are not limited to, muscle weakness and loss, difficulty running, difficulty hopping, difficulty jumping, difficulty walking, difficulty breathing, fatigue, skeletal deformities, muscle deformities (contractions of heels; pseudohypertrophy of calf muscles), heart disease (such as dilated cardiomyopathy), elevated creatine phosphokinase (CK) levels in blood or combinations thereof.

Subject: Living multi-cellular vertebrate organisms, a category that includes human and non-human mammals.

Therapeutically-effective amount: An amount effective for lessening, ameliorating, eliminating, preventing, or inhibiting at least one symptom of a disease, disorder, or condition treated and may be empirically determined. In various embodiments of the present disclosure, a "therapeutically-effective amount" is a "muscle regeneration promoting-amount," an amount sufficient to achieve a statistically significant promotion of tissue or cell regeneration, such as muscle cell regeneration, compared to a control. In particular, indicators of muscular health, such as muscle cell regeneration, maintenance, or repair, can be assessed through various means, including monitoring markers of muscle regeneration, such as transcription factors such as Pax7, Pax3, MyoD, MRF4, and myogenin. For example, increased expression of such markers can indicate that muscle regeneration is occurring or has recently occurred. Markers of muscle regeneration, such as expression of embryonic myosin heavy chain (eMyHC), can also be used to gauge the extent of muscle regeneration, maintenance, or repair. For example, the presence of eMyHC can indicate that muscle regeneration has recently occurred in a subject.

Muscle cell regeneration, maintenance, or repair can also be monitored by determining the girth, or mean cross sectional area, of muscle cells or density of muscle fibers. Additional indicators of muscle condition include muscle weight and muscle protein content. Mitotic index (such as by measuring BrdU incorporation) and myogenesis can also be used to evaluate the extent of muscle regeneration.

In particular examples, the improvement in muscle condition, such as regeneration, compared with a control is at least about 10%, such as at least about 30%, or at least about 50% or more.

Tissue: An aggregate of cells, usually of a particular kind, together with their intercellular substance that form one of the structural materials of an animal and that in animals include connective tissue, epithelium, muscle tissue, and nerve tissue.

Treating a disease: A therapeutic intervention that ameliorates a sign or symptom of a disease or pathological condition related to a muscular dystrophy, such as a sign or symptom of muscular dystrophy. Treatment can induce remission or cure of a condition or slow progression, for example, in some instances can include inhibiting the full development of a disease, for example preventing development of a muscular dystrophy. Prevention of a disease does not require a total absence of disease. For example, a decrease of at least 20%, such as at least 30%, at least 40%, at least 50%, decrease in a sign or symptom associated with the condition or disease, such as MD, can be sufficient. As used herein, the term "ameliorating," with reference to a disease or condition, refers to any observable beneficial effect of the treatment. The beneficial effect can be evidenced, for example, by a delayed onset of clinical symptoms of the disease or condition in a susceptible subject, a reduction in severity of some or all clinical symptoms of the disease or condition, a slower progression of the disease or condition, a reduction in the number of relapses of the disease or condition, an improvement in the overall health or well-being of the subject, by other parameters well known in the art that are specific to the particular disease or condition, and combinations of such factors.

III. Methods of Diagnosing and Prognosing Muscular Dystrophy

Methods are disclosed for diagnosing and prognosing muscular dystrophy, such as DMD, LGMD, FHMD, Beckers muscular dystrophy (BMD) or MDC1A, in a subject. In one example, the methods include detecting expression of at least one (such as at least 2, at least 3, at least 4, at least 5, at least 6, at least 7, at least 8, at least 30, at least 50, at least 80, at least 100, at least 190 or more) muscular dystrophy-associated molecules in a sample obtained from a subject either at risk of having or having one or more signs or symptoms associated with muscular dystrophy. In some examples, the muscular dystrophy-associated molecules can include, consist essentially of, or consist of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) or any combination thereof. In some examples, muscular dystrophy-associated molecules include Galectin-1, Galectin-3, Col6A1, Itga3, Iga6, Itga7, Tnc and Timp 1. In some examples, muscular dystrophy-associated molecules include Galectin-1 and Galectin-3. In some examples, muscular dystrophy-associated molecules include Galectin-3 and Tnc. In some examples, the muscular dystrophy-associated molecules include at least Galectin-3 for detecting DMD, LGMD, FHMD, BMD or MDC1A. In some examples, the muscular dystrophy-associated molecules include at least Galectin-3 for detecting DMD. "Consists essentially of" in this context indicates that the expression of additional molecules can be evaluated (such as a control), but that these molecules do not include more than the listed muscular dystrophy-associated molecules. Thus, in one example, the expression of a control, such as a housekeeping protein or rRNA can be assessed (such as 18S RNA, beta-microglobulin, GAPDH, and/or 18S rRNA). In some examples, "consist essentially of" indicates that no more than 5 other molecules are evaluated, such as no more than 4, 3, 2, or 1 other molecules. In this context "consist of" indicates that only the expression of the stated molecules are evaluated; the expression of additional molecules is not evaluated.

The methods also can include comparing expression of the at least one muscular dystrophy-associated molecule in the sample obtained from the subject at risk of having or having one or more signs or symptoms associated with muscular dystrophy to a control, wherein an increase in the expression of the at least one muscular dystrophy-associated molecule relative to the control indicates that the subject has a decreased chance of survival. For example, an increase in the expression of Galectin-3 relative to a normal control sample or reference value (or range of values) indicates a poor prognosis, such as a decreased chance of survival. In an example, a decreased chance of survival includes a survival time of equal to or less than 50 months, such as 40 months, 30 months, 20 months, 12 months, 6 months or 3 months from time of diagnosis. Conversely, a decrease in expression of a muscular dystrophy-associated molecule or expression levels similar to those in control levels indicates a better prognosis, such as an increased chance of survival (e.g., survival time of at least 50 months from time of diagnosis, such as 60 months, 80 months, 100 months, 120 months or 150 months from time of diagnosis). For example, the level of the muscular dystrophy-associated molecule detected can be compared to a control or reference value, such as a value that represents a level of a muscular dystrophy-associated molecule expected if a subject does not have muscular dystrophy. In one example, the muscular dystrophy-associated molecule detected in the sample obtained from the subject being evaluated is compared to the level of such molecules detected in a sample obtained from a subject that does not have muscular dystrophy. In certain examples, detection of at least a 2-fold, such as at least 3-fold, at least 4-fold, at least 6-fold or at least 10-fold increase in the relative amount of the muscular dystrophy-associated molecule in the test sample, as compared to the relative amount of such molecules in a control, indicates that the subject has muscular dystrophy, such as DMD, LGMD, or MDC1A, has a poor prognosis (e.g., survival time of less than 50 months from time of diagnosis, such as 40 months, 30 months, 20 months, 12 months, 6 months or 3 months from time of diagnosis or increased muscle deterioration), or combinations thereof. In some examples, detection of statistically similar relative amounts (or decreased amounts) of muscular dystrophy-associated molecules observed in a test sample, as compared to the relative amount of such molecules in a control sample, indicates that that subject does not have muscular dystrophy, such as DMD, LGMD, FHMD, BMD or MDC1A, has a good prognosis (survival time of at least 50 months from time of diagnosis, such as 60 months, 80 months, 100 months, 120 months or 150 months from time of diagnosis), or combinations thereof.

Alterations in the expression can be measured at the nucleic acid level (such as by real time quantitative polymerase chain reaction or microarray analysis) or at the protein level (such as by Western blot analysis or ELISA).

In some examples, such methods can be used to identify those subjects that will benefit from the disclosed treatment methods. For example, such diagnostic or prognostic methods can be performed prior to the subject undergoing the treatment. In other examples, these methods are utilized to predict subject survival or the efficacy of a given treatment, or combinations thereof. Thus, the methods of the present disclosure are valuable tools for practicing physicians to make quick treatment decisions regarding how to treat muscular dystrophy, such as DMD, LGMD, FHMD, BMD or MDC1A. These treatment decisions can include the administration of an agent for treating one or more signs or symptoms associated with muscular dystrophy and decisions to monitor a subject for onset and/or advancement of a muscular dystrophy associated condition. The method disclosed herein can also be used to monitor the effectiveness of a therapy.

Following the measurement of the expression levels of one or more of the molecules identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the muscular dystrophy-associated molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having muscular dystrophy, such as DMD, LGMD, FHMD, BMD or MDC1A, results in the physician treating the subject, such as prescribing one or more agents for inhibiting or delaying one or more signs and symptoms associated with muscular dystrophy. In additional embodiments, the dose or dosing regimen is modified based on the information obtained using the methods disclosed herein.

Detection of Muscular Dystrophy-Associated Nucleic Acids

In one example, one or more muscular dystrophy-associated molecules can be detected by polymerase chain reaction (PCR). The biological sample can be incubated with primers that permit the amplification of one or more of the disclosed muscular dystrophy, such as DMD, LGMD, or MDC1A-associated mRNAs, under conditions sufficient to permit amplification of such products.

In another example, the biological sample is incubated with probes that can bind to one or more of the disclosed muscular dystrophy-associated nucleic acid sequences (such as cDNA, genomic DNA, or RNA (such as mRNA)) under high stringency conditions. The resulting hybridization can then be detected using methods known in the art, such as by Northern blot analysis.

In an example, the isolated nucleic acid molecules or amplification products are incubated with an array including oligonucleotides complementary to at least one muscular dystrophy-associated molecule, such as disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lamas), nidogen 1 (Nid1), tenascin C (Tnc), tissue inhibitor of metalloproteinase 1 (Timp1), tissue inhibitor of metalloproteinase 2 (Timp2) or any combination thereof for a time sufficient to allow hybridization between the isolated nucleic acid molecules and oligonucleotide probes, thereby forming isolated nucleic acid molecule: oligonucleotide complexes. The isolated nucleic acid molecule:oligonucleotide complexes are then analyzed to determine if expression of the isolated nucleic acid molecules is altered.

In some examples, oligonucleotides complementary to Galectin-1, Galectin-3, Col6A1, Itga3, Iga6, Itga7, Tnc and Timp 1 are included within the array. In some examples, an array includes oligonucleotides complementary to at least Galectin-1 and Galectin-3. In some examples, an array includes oligonucleotides complementary to at least Galectin-3 and Tnc. In some examples, an array includes oligonucleotides complementary to at least Galectin-3 for detecting DMD, LGMD, FHMD, BMD or MDC1A. In some examples, an array includes oligonucleotides complementary to at least Galectin-1 for detecting DMD. In some examples, an array includes oligonucleotides complementary to at least Galectin-1 for detecting DMD, LGMD, FHMD, BMD or MDC1A. In some examples, an array includes oligonucleotides complementary to at least Galectin-1 for detecting DMD.

Detecting Muscular Dystrophy-Associated Proteins

As an alternative to analyzing the sample for the presence of nucleic acids, alterations in protein expression can be measured by methods known in the art, such as by Western blot analysis, immunoassay (e.g., ELISA), mass spectrometry or a protein microarray. For example, the presence of one or more muscular dystrophy-associated molecules can be determined by using a protein array that includes one or more capture agents, such as antibodies that are specific for the one or more disclosed muscular dystrophy-associated molecules.

In one example, the antibody that specifically binds a muscular dystrophy-associated molecule (such as Galectin-1 or Galectin-3) is directly labeled with a detectable label. In another example, each antibody that specifically binds a muscular dystrophy-associated molecule (the first antibody) is unlabeled and a second antibody or other molecule that can bind the human antibody that specifically binds the respective muscular dystrophy-associated molecule is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, Cy3, Cy5, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}I$, $^{131}I$, $^{35}S$ or $^{3}H$.

In some examples, the presence of one or more muscular dystrophy-associated molecules can be determined by using an ELISA. ELISA is a heterogeneous immunoassay, which has been widely used in laboratory practice since the early 1970s, and can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a urine sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

In an alternative example, muscular dystrophy-associated molecules can be assayed in a biological sample by a competition immunoassay utilizing muscular dystrophy-associated molecule standards labeled with a detectable substance and unlabeled antibody that specifically bind to the desired muscular dystrophy-associated molecule. In this assay, the biological sample (such as serum, tissue biopsy, or cells isolated from a tissue biopsy), the labeled muscular dystrophy-associated molecule standards and the antibody that specifically binds to the muscular dystrophy-associated molecule are combined and the amount of labeled muscular dystrophy-associated molecule standard bound to the unlabeled antibody is determined. The amount of muscular dystrophy-associated molecule in the biological sample is inversely proportional to the amount of labeled muscular dystrophy-associated molecule standard bound to the antibody that specifically binds the muscular dystrophy-associated molecule.

In some examples, ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogenous immunoassay, such as an ELISA, can be used to detect any molecules associated with muscular dystrophy.

The methods as disclosed herein, such as with a method diagnosing a subject with MD or determining the effectiveness of a particular treatment, can be performed manually or automatically, for example on an automated sample processing instrument with capability of detecting nucleic acid and protein sequences and comparing expression levels of such sequences. Automated systems typically are at least partially, if not substantially entirely, under computer control. Because automated systems typically are at least partially computer controlled, certain embodiments of the present disclosure also concern one or more tangible computer-readable media that stores computer-executable instructions for causing a computer to perform disclosed embodiments of the method. Thus, disclosed are computers or tangible computer readable medium with instructions for the disclose methods. Tangible computer readable medium means any physical object or computer element that can store and/or execute computer instructions. Examples of tangible computer readable medium include, but not limited to, a compact disc (CD), digital versatile disc (DVD), blu-ray disc (BD), usb floppy drive, floppy disk, random access memory (RAM), read-only memory (ROM), erasable programmable read-only memory (EPROM), optical fiber, and the like. It should be noted that the tangible computer readable medium may even be paper or other suitable medium in which the instructions can be electronically captured, such as optical scanning. Where optical scanning occurs, the instructions may be compiled, interpreted, or otherwise processed in a suitable manner, if necessary, and then stored in computer memory.

Alternatively, it may be a plugin or part of a software code that can be included in, or downloaded and installed into a computer application. As a plugin, it may be embeddable in any kind of computer document, such as a webpage, word document, pdf file, mp3 file, etc.

An exemplary computer system for implementing a disclosed method, such as with a method diagnosing a subject with MD or determining the effectiveness of a particular treatment, includes a computer (such as a personal computer, laptop, palmtop, set-top, server, mainframe, hand held device, and other varieties of computer), including a processing unit, a system memory, and a system bus that couples various system components including the system memory to the processing unit. The processing unit can be any of various commercially available processors, including INTEL® x86, PENTIUM® and compatible microprocessors from INTEL® and others, including Cyrix, AMD and Nexgen; Alpha from Digital; MIPS from MIPS Technology, NEC, IDT®, Siemens, and others; and the PowerPC from IBM® and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. A basic input/output system (BIOS), containing the basic routines that help to transfer information between elements within the computer, such as during start-up, is stored in ROM. The system memory includes read only memory and random access memory (RAM).

The computer may further include a hard disk drive, a magnetic disk drive, for example to read from or write to a removable disk, and an optical disk drive, for example to read a CD-ROM disk or to read from or write to other optical media. The hard disk drive, magnetic disk drive, and optical disk drive are connected to the system bus by a hard disk drive interface, a magnetic disk drive interface, and an optical drive interface, respectively. The drives and their associated computer readable media provide nonvolatile storage of data, data structures (databases), computer executable instructions, etc. for the computer. Although the description of computer readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A user can enter commands and information into the computer using various input devices, such as a keyboard and pointing device, such as a mouse. Other input devices can include a microphone, satellite dish, scanner, or the like. These and other input devices are often connected to the processing unit through a serial port interface that is coupled to the system bus, but can be connected by other interfaces, such as a parallel port, game port or a universal serial bus (USB). A monitor or other type of display device is also connected to the system bus via an interface, such as a video adapter. In addition to the monitor, computers typically include other peripheral output devices, such as printers.

The computer can operate in a networked environment using logical connections to one or more other computer systems, such as computer. The other computer systems can be servers, routers, peer devices or other common network nodes, and typically include many or all of the elements described relative to the computer. Logical connections can include a local area network (LAN) and a wide area network (WAN). Such networking environments are common in offices, enterprise-wide computer networks, intranets and the Internet.

When used in a LAN networking environment, the computer is connected to the local network through a network interface or adapter. When used in a WAN networking environment, the computer 120 typically includes a modem or other means for establishing communications (for example via the LAN and a gateway or proxy server) over the wide area network, such as the Internet. The modem, which can be internal or external, is connected to the system bus via the serial port interface. In a networked environment, program modules depicted relative to the computer, or portions thereof, can be stored in the remote memory storage device. It will be appreciated that the network connections shown are exemplary and other means of establishing a communications link between the computer systems (including an Ethernet card, ISDN terminal adapter, ADSL modem, 10 BaseT adapter, 100 BaseT adapter, ATM adapter, or the like) can be used.

The methods, including the acts and operations they comprise, described above can be performed by the computer. Such acts and operations are sometimes referred to as being computer executed. It will be appreciated that the acts and symbolically represented operations include the manipulation by the processing unit of electrical signals representing data bits which causes a resulting transformation or reduction of the electrical signal representation, and the maintenance of data bits at memory locations in the memory system (including the system memory, hard drive, floppy disks, and CD-ROM) to thereby reconfigure or otherwise alter the computer system's operation, as well as other processing of signals. The memory locations where data bits are maintained are physical locations that have particular electrical, magnetic, or optical properties corresponding to the data bits.

It is contemplated that a distributed computing environment can be used to implement the methods and systems of the present disclosure may reside. The distributed computing environment includes two computer systems connected by a connection medium, although the disclosed method is equally applicable to an arbitrary, larger number of computer systems connected by the connection medium. The computer systems can be any of several types of computer system configurations, including personal computers, multiprocessor systems, handheld devices, and the like. In terms of logical relation with other computer systems, a computer system can be a client, a server, a router, a peer device, or other common network node. Additional computer systems may be connected by an arbitrary number of connection mediums. The connection medium can comprise any local area network (LAN), wide area network (WAN), or other computer network, including but not limited to Ethernets, enterprise-wide computer networks, intranets and the Internet.

Portions of the software for automated gene detection and quantification as well as databases storing correlation data can be implemented in a single computer system, with the application later distributed to other computer systems in the distributed computing environment. Portions of the software for determining gene expression and quantification may also be practiced in a distributed computing environment where tasks are performed by a single computer system acting as a remote processing device that is accessed through a communications network, with the distributed application later distributed to other computer systems in the distributed computing environment. In a networked environment, program modules comprising the software for determining gene expression and quantification as well as databases storing the correlation data can be located on more than one computer system. Communication between the computer systems in the distributed computing network may advantageously include encryption of the communicated data.

In certain embodiments, the communication containing results of a diagnostic test and/or conclusions drawn from and/or treatment recommendations based on the test, may be generated and delivered automatically to the subject, facility, physician and the like using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

IV. Methods of Use

It is shown herein that muscular dystrophy is associated with differential expression of muscular dystrophy-associated molecules, such as disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2). Based on these observations, methods of treatment to reduce or eliminate one or more signs or symptoms associated with muscular dystrophy, such as DMD, LGMD, FHMD, BMD or MDC1A are disclosed by decreasing the expression of at least one of the disclosed muscular dystrophy-associated molecules. In a particular example, the subject is a human.

Methods are disclosed herein for treating muscular dystrophy, such as DMD, LGMD, FHMD, BMD or MDC1A. In one example, the method includes administering an effective amount of an agent to a subject with muscular dystrophy in which the agent alters the biological activity or expression of one or more of the disclosed muscular dystrophy-associated molecules, such as one or more of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2). Such agents can alter the expression of nucleic acid sequences (such as DNA, cDNA, or mRNAs) and proteins. In some examples, an agent decreases alters the biological activity or expression of one or more of the disclosed muscular dystrophy-associated molecules. A decrease in the expression does not need to be 100% for the composition to be effective. For example, an agent can decrease the expression or biological activity by a desired amount, for example by at least 20%, at least 50%, at least 60%, at least 70%, at least 80%, at least 90%, at least 95%, at least 98%, or even at least 100% as compared to activity or expression in a control. In some examples, an agent increases the biological activity or expression of one or more of the disclosed muscular dystrophy-associated molecules In particular examples, the agent is a specific binding agent that binds to and decreases the expression of one or more of the disclosed muscular dystrophy-associated molecules. Specific molecules include disintegrin and metalloproteinase with thrombospondin motifs 5 (Adamts5), agrin (Agrn), collagen 6A1 (Col6a1), galectin, such as Galectin-3, matrix metalloproteinase 2 (Mmp2), integrin α3 (Iga3), integrin α6 (Iga6), integrin α7 (Iga7), laminin-α4 (Lama4), laminin-α5 (Lamas), nidogen 1 (Nid1), tenascin C (Tnc), tissue inhibitor of metalloproteinase 1 (Timp1), tissue inhibitor of metalloproteinase 2 (Timp2) as well as fragments of the full-length molecules, cDNAs, or mRNAs (and proteins encoded thereby) whose expression is increased in response to muscular dystrophy, such as DMD, LGMD, FHMD, BMD or MDC1A. The agents can alter the activity or expression of the one or more disclosed muscular dystrophy-associated molecules well as other molecules involved in muscular dystrophy progression.

In particular examples, the agent is an inhibitor such as a siRNA or an antibody to one of the disclosed muscular dystrophy-associated molecules that is upregulated in muscular dystrophy patients. For example, the agent can be an siRNA that interferes with mRNA expression of one of the disclosed muscular dystrophy-associated molecules. For example, the agent is an siRNA that inhibitor reduces expression of one or more of the disclosed muscular dystrophy-associated molecules. In additional examples, a composition includes at least two agents such as two specific siRNAs that each bind to their respective muscular dystrophy-associated nucleotide sequences and inhibit one or more signs or symptoms associated with muscular dystrophy in the subject. In some examples, the agent is an activator or agonist that is used to stimulate or increase the biological activity or expression of one of the disclosed muscular dystrophy-associated molecules.

Also disclosed are methods of increasing/maintaining muscle strength and/or bone density. In some examples, an effective amount of galectin or galectin composition, such as galectin-1 composition, is administered to increase muscle strength and/or bone density and/or prevent, inhibit or slow muscle and bone loss. In some examples, galectin or a galectin composition, such as galectin-1 composition, is administered to a subject at risk of muscle/bone injury or muscle/bone loss, such as to an athlete, an astronaut, or any other individual that partakes in activities that may cause muscle/bone injury and/or loss. In some examples, a disclosed regimen, such as a disclosed galectin-1 regimen, is provided to prevent muscle/bone injury and/or loss. In some examples, a disclosed regimen, such as a disclosed galectin-1 regimen, is provided to maintain bone density and/or muscle strength. In some examples, a disclosed regimen, such as a disclosed galectin-1 regimen, is provided to treat a subject experiencing a loss in bone density and/or muscle strength whereby the regimen is administered in a manner to lead to an increase in bone density and/or muscle strength or to maintain the existing muscle strength and bone density (e.g., prevent further loss of muscle strength and/or bone density).

In some examples, galectin or a galectin composition, such as a Galectin-1 composition, is administered to a subject at risk of acquiring or suffering from a condition or disease associated with muscle loss, bone loss, muscle density loss, and/or muscle strength loss, such as, but not limited to a subject at risk of acquiring or suffering from kyphosis, muscular dystrophies, scoliosis, broken bones, muscle strains, muscle tears, tendon injury, osteoporosis, rheumatoid arthritis, lupus, scoliosis and/or multiple sclerosis. In some examples, galectin or a galectin composition, such as a Galectin-1 composition, is administered for preventing, treating or slowing the progression of a sign or symptom associated with aging. It is contemplated that galectin or a galectin composition can be administered for short or prolong periods of time, ranging from days to years. In some examples, galectin or a galectin composition, such as Galectin-1 or a Galectin-1 composition, is administered post-surgery, such as to a subject that has undergone surgery and may be at risk of experiencing or has muscle loss, bone loss, muscle strength loss or muscle density loss. In some examples, a galectin composition, such as Galectin-1, is administered to a female subject post-pregnancy. In some examples, a galectin composition, such as Galectin-1, is administered to a short or long-term coma subject.

Agents

Desirable agents are those that when administered in effective amounts induce the desired response (e.g., prevent, inhibit, or treat one or more signs of a particular condition or disease, including but not limited to kyphosis, muscular dystrophies, scoliosis, broken bones, muscle strains, muscle tears, tendon injury, osteoporosis, rheumatoid arthritis, lupus, scoliosis and/or multiple sclerosis). In one example, agents are specific binding agents that bind with higher affinity to a molecule of interest, than to other molecules. For example, a specific binding agent can be one that binds with high affinity to one of the genes or gene products of a disclosed muscular dystrophy-associated molecules, but does not substantially bind to another gene or gene product. In some examples, a specific binding agent binds to one thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) that are upregulated in muscular dystrophy subjects, thereby reducing or inhibiting expression of the gene, but does not bind to the other genes (or gene product).

In some examples, the agent interferes with gene expression (transcription, processing, translation, post-translational modification), such as, by interfering with the gene's mRNA and blocking translation of the gene product or by post-translational modification of a gene product, or by causing changes in intracellular localization. In another example, a specific binding agent binds to a protein encoded by of one of the genes disclosed herein to be associated with the specific condition or disease with a binding affinity in the range of 0.1 to 20 nM and reduces or inhibits the activity of such protein. In some examples, the agent increases gene expression (transcription, processing, translation, post-translational modification) or the activity of the protein associated with the specific condition or disease.

Examples of specific binding agents include siRNAs, antibodies, ligands, recombinant proteins, peptide mimetics, and soluble receptor fragments. One example of a specific binding agent is a siRNA. Methods of making siRNAs that can be used clinically are known in the art. Particular siRNAs and methods that can be used to produce and administer them are described in detail below. In a specific example, a specific binding agent includes a Galectin-3 siRNA molecule.

Another specific example of a specific binding agent is an antibody, such as a monoclonal or polyclonal antibody. Methods of making antibodies that can be used clinically are known in the art. Particular antibodies and methods that can be used to produce them are known to those of ordinary skill in the art. Further, antibodies to Galectin-1 and Galectin-3 are commercially available.

In a further example, small molecular weight inhibitors/antagonists or activators/agonists of the receptor protein can be used to regulate activity such as the expression or production of muscular dystrophy-associated molecules. In a particular example, small molecular weight inhibitors/antagonists or activators/agonists of the proteins encoded by the genes of thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), and/or tissue inhibitor of metalloproteinase 2 (Timp2) are used.

Specific binding agents can be therapeutic, for example by altering the biological activity of a nucleic acid or protein that is associated muscular dystrophy progression. For example, a specific binding agent that binds with high affinity to one or more genes disclosed herein to be upregulated in subjects with muscular dystrophy, may substantially reduce the biological function of the gene or gene product. In other examples, a specific binding agent that binds with high affinity to one of the proteins disclosed herein to be upregulated in subjects with muscular dystrophy, may substantially reduce the biological function of the protein. Such agents can be administered in effective amounts to subjects in need thereof, such as a subject having muscular dystrophy, such as DMD, LGMD, FHMD, BMD or MDC1A.

In other examples, a specific binding agent that binds with high affinity to one or more genes disclosed herein to be upregulated in subjects with muscular dystrophy, may substantially increase the biological function of the gene or gene product. In other examples, a specific binding agent that binds with high affinity to one of the proteins disclosed herein to be upregulated in subjects with muscular dystrophy, may substantially increase the biological function of the protein. Such agents can be administered in effective amounts to subjects in need thereof, such as a subject having muscular dystrophy, such as DMD, LGMD, FHMD, BMD or MDC1A.

For example, galectin or a composition comprising galectin can be therapeutic. The present disclosure relates to a method of providing benefit to a subject by administering to the subject a galectin or a composition that includes galectin, such as Galectin-1 or Galectin-3. In a particular embodiment, the present disclosure provides a method of enhancing muscle regeneration, such as to treat muscular dystrophy, in a subject by administering galectin or a galectin composition.

In various embodiments, the present disclosure provides a method of treating a subject with galectin or a composition that includes galectin. For example, some embodiments provide methods of improving muscular health, such as enhancing muscle regeneration, maintenance, or repair in a subject by administering to the subject an effective amount of galectin or a composition comprising galectin, including fragments, derivatives, or analogs thereof. In a specific example, the galectin is a complete galectin protein. In further examples, the galectin is selected from Galectin-1, Galectin-3, and combinations thereof. In further examples, the galectin or galectin composition includes a substance at least substantially homologous to Galectin-1 or Galectin-3. In yet further implementations, the galectin or galectin composition comprises a polypeptide at least substantially homologous to the Galectin-1 or Galectin-3.

In additional examples, the galectin or galectin composition consists of Galectin-1, Galectin-3, and combinations thereof. In further examples, the galectin or galectin composition consists of a substance at least substantially homologous to Galectin-1 or Galectin-3. In a specific example, the galectin or galectin composition does not include a galectin fragment, such as including only a complete galectin protein.

In yet another example, the galectin or galectin composition consists essentially of Galectin-1, Galectin-3, and combinations thereof. In further examples, the galectin or galectin composition consists essentially of a substance at least substantially homologous to Galectin-1 or Galectin-3. In yet further implementations, the galectin or galectin composition consists essentially of a polypeptide at least substantially homologous to the galectin α1 chain. In a specific example, the galectin or galectin composition does not include a galectin fragment, such as including essentially only a complete galectin protein.

Further implementations of the disclosed method include diagnosing the subject as having a condition treatable by administering galectin or a composition comprising galectin, such as by administering Galectin-1, Galectin-3 or a combination thereof or a composition containing Galectin-1, Galectin-3 or a combination. In one example, the subject is diagnosed as suffering from muscular dystrophy, such as LGMD, FHMD, Beckers muscular dystrophy and/or MDC1A. In further instances the condition is characterized by the failure of a subject, or the reduced ability of the subject, to express one or more proteins associated with the formation or maintenance of the extracellular matrix, such as impaired or non-production of a galectin, an integrin, dystrophin, utrophin, or dystroglycan.

In a specific embodiment, the present disclosure also provides a method for increasing muscle regeneration in a subject. For example, geriatric subjects, subjects suffering from muscle disorders, and subjects suffering from muscle injury, including activity induced muscle injury, such as injury caused by exercise, may benefit from this embodiment.

In yet further embodiments of the disclosed method, the galectin or galectin composition, such as Galectin-1, Galectin-3 or a combination thereof containing composition, is administered in a preventative manner, such as to prevent or reduce muscular and/or bone damage or injury (such as activity or exercise induced injury). For example, geriatric subjects, subjects prone to muscle damage, or subjects at risk for muscular injury, such as athletes, may be treated in order to eliminate or ameliorate muscular damage, injury, or disease.

Implementations of the present disclosure may also be used to promote wound healing. In some examples, a galectin or a composition comprising galectin is administered into or proximate to a wound. In further examples, the substance is administered systemically. Although the substance is typically applied after the wound occurs, the substance can be applied prospectively in some examples.

In further embodiments, the method of the present disclosure includes administering the galectin or galectin composition, such as Galectin-1, Galectin-3 or a combination thereof containing composition, with one or more additional pharmacological substances, such as a therapeutic agent. In some aspects, the additional therapeutic agent enhances the therapeutic effect of the galectin or galectin composition. In further aspects, the therapeutic agent provides independent therapeutic benefit for the condition being treated. In various examples, the additional therapeutic agent is a component of the extracellular matrix, such as an integrin, dystrophin, dystroglycan, utrophin, or a growth factor. In further examples, the therapeutic agent reduces or enhances expression of a substance that enhances the formation or maintenance of the extracellular matrix.

In some examples, the galectin or galectin composition is applied to a particular area of the subject to be treated. For example, the galectin or galectin composition may be injected into a particular area to be treated, such as a muscle. In further examples, the galectin or galectin composition is administered such that it is distributed to multiple areas of the subject, such as systemic administration or regional administration.

Galectin, or a composition comprising galectin, such as Galectin-1, Galectin-3, or a combination thereof, can be administered by any suitable method, such as topically, parenterally (such as intravenously or intraperitoneally), or orally. In a specific example, the galectin or galectin composition is administered systemically, such as through parenteral administration, such as stomach injection or peritoneal injection.

Although the disclosed methods generally have been described with respect to muscle regeneration, the disclosed methods also may be used to enhance repair or maintenance, or prevent damage to, other tissues and organs. For example, the methods of the present disclosure can be used to treat symptoms of muscular dystrophy stemming from effects to cells or tissue other than skeletal muscle, such as impaired or altered brain function, smooth muscles, or cardiac muscles.

Pre-Screening Therapeutic Agents

In some examples, potential therapeutic agents are initially screened for treating muscular dystrophy, such as DMD, LGMD, FHMD, BMD or MDC1A, by detecting one or more muscular dystrophy-associated molecules (as discussed in detail below in Section VI.). For example, the disclosed muscular dystrophy-associated molecules can be used to identify agents capable of reducing or inhibiting one or more signs or symptoms of muscular dystrophy. In an example, subjects can be first pre-screened for the presence of muscular dystrophy, such as DMD, LGMD, FHMD, BMD or MDC1A, which will respond to a particular therapeutic agent prior to receiving treatment.

Administration

Methods of administration of the disclosed compositions are routine, and can be determined by a skilled clinician. For example, the disclosed therapies (such as those that include a binding agent specific for one of the disclosed muscular dystrophy-associated molecules or a galectin, such as Galectin-1) can be administered via injection, orally, topically, transdermally, parenterally, or via inhalation or spray. In a particular example, a composition is administered intravenously to a mammalian subject, such as a human. In another example, the composition is administered orally. In some examples, the composition is applied to a particular are of the subject to be treated. For example, the composition is injected into a muscle.

The therapeutically effective amount of the agents administered can vary depending upon the desired effects and the subject to be treated. In one example, the method includes daily administration of at least 1 μg of a therapeutic agent to the subject (such as a human subject). For example, a human can be administered at least 1 μg or at least 1 mg of the agent daily, such as 10 μg to 100 μg daily, 100 μg to 1000 μg daily, for example 10 μg daily, 100 μg daily, or 1000 μg daily. In one example, the subject is administered at least 1 μg (such as 1-100 μg) intravenously of the agent (such as a composition that includes a binding agent that specifically binds to one of the disclosed muscular dystrophy-associated molecules or a galectin, such as Galectin-1 or Galectin-3). In one example, the subject is administered at least 1 mg intramuscularly (for example in an extremity) of such composition. The dosage can be administered in divided doses (such as 2, 3, or 4 divided doses per day), or in a single dosage daily.

In particular examples, the subject is administered the therapeutic composition that includes a binding agent specific for one of the disclosed muscular dystrophy-associated molecules or a galectin, such as Galectin-1, Galectin-3 or a combination thereof, on a multiple daily dosing schedule, such as at least two consecutive days, 10 consecutive days, and so forth, for example for a period of weeks, months, or years. In one example, the subject is administered the therapeutic composition that includes a binding agent specific for one of the disclosed muscular dystrophy-associated molecules or a galectin, such as Galectin-1, Galectin-3 or a combination thereof daily for a period of at least 30 days, such as at least 2 months, at least 4 months, at least 6 months, at least 12 months, at least 24 months, or at least 36 months.

The compositions, such as those that include a binding agent specific for one of the muscular dystrophy-associated molecules or a galectin (such as Galectin-1, Galectin-3 or a combination thereof), can further include one or more biologically active or inactive compounds (or both), such as other agents known in the art for reducing or treating one or more signs or symptoms associated with muscular dystrophy and conventional non-toxic pharmaceutically acceptable carriers, respectively. For example, additional therapeutic agent which enhance the therapeutic effect of the disclosed compositions are included, such as a component of the extracellular matrix, such as an integrin, dystrophin, dystroglycan, utrophin, or a growth factor. In further examples, the additional therapeutic agent reduces or enhances expression of a substance that enhances the formation or maintenance of the extracellular matrix. In some examples, the additional substance can include aggrecan, angiostatin, cadherins, collagens (including collagen I, collagen III, or collagen IV), decorin, elastin, enactin, endostatin, fibrin, fibronectin, osteopontin, tenascin, thrombospondin, vitronectin, and combinations thereof. Biglycans, glycosaminoglycans (such as heparin), glycoproteins (such as dystroglycan), proteoglycans (such as heparan sulfate), and combinations thereof can also be administered. A particular laminin can be administered with other forms of laminin, laminin analogs, laminin derivatives, or a fragment of any of the foregoing.

In some examples, growth stimulants such as cytokines, polypeptides, and growth factors such as brain-derived neurotrophic factor (BDNF), CNF (ciliary neurotrophic factor), EGF (epidermal growth factor), FGF (fibroblast growth factor), glial growth factor (GGF), glial maturation factor (GMF) glial-derived neurotrophic factor (GDNF), hepatocyte growth factor (HGF), insulin, insulin-like growth factors, kerotinocyte growth factor (KGF), nerve growth factor (NGF), neurotropin-3 and -4, PDGF (platelet-derived growth factor), vascular endothelial growth factor (VEGF), and combinations thereof may be administered with one of the disclosed therapies.

In a particular example, a therapeutic composition that includes a therapeutically effective amount of a therapeutic agent (such as a binding agent specific for one of the disclosed muscular dystrophy-associated molecules or a galectin, such as Galectin-1, Galectin-3 or a combination thereof) further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

The compositions can be formulated in a palatable form for administration as a food additive or supplement. Such palatable forms are typically odor free or are masked or coated as is known to those of ordinary skill in the art of pharmaceutical formulation. Where the disclosed compounds are administered orally, particularly when they are administered as a nutritional supplement, the compounds can be mixed with a foodstuff base. Such mixtures can be in the form of an emulsion or an admixture with solid food. In some examples, the disclosed compositions, such as a Galectin-1 composition, can be mixed with yogurt. For example, health bars, without limitation, can be prepared by combining various excipients, such as binders, fillers, flavorings, colorants and the like, along with one or more galectins, such as Galectin-1, and mixing to a plastic mass consistency. The mass is then either extruded or molded to form "candy bar" shapes that are then dried or allowed to solidify to form the final product.

Alternatively, the compounds can be administered orally in a liquid dosage form as a solution, emulsion or suspension. The liquid dosage form can contain, for example, suitable solvents, preservatives, emulsifying agents, suspending agents, diluents, sweeteners, melting agents, and coloring and flavoring agents, which are known to those of ordinary skill in the art. The compounds also can be added to liquid vitamin formulations and electrolyte containing drinks. Drinks may be in the form of energy drinks, sports drinks, fruit drinks, citrus drinks, carbonated drinks, dry drink mixes, other suitable drink mediums or combinations thereof.

Additional Treatments

In particular examples, prior to, during, or following administration of an effective amount of an agent that reduces or inhibits one or more signs or symptoms associated with muscular dystrophy, the subject can receive one or more other therapies. In one example, the subject receives one or more treatments prior to administration of a disclosed agent specific for one of the disclosed muscular dystrophy-associated molecules or a galectin, such as galectin protein therapy (e.g., Galectin-1/Galectin-3 protein therapy). Examples of such therapies include, but are not limited to, laminin-111 protein therapy, which works to stabilize the sarcolemma and reduce muscle degeneration. In some examples, a source of muscle cells can be added to aid in muscle regeneration and repair. In some aspects of the present disclosure, satellite cells are administered to a subject in combination with laminin therapy. U.S. Patent Publication 2006/0014287, incorporated by reference herein to the extent not inconsistent with the present disclosure, provides methods of enriching a collection of cells in myogenic cells and administering those cells to a subject. In further aspects, stem cells, such as adipose-derived stem cells, are administered to the subject. Suitable methods of preparing and administering adipose-derived stem cells are disclosed in U.S. Patent Publication 2007/0025972, incorporated by reference herein to the extent not inconsistent with the present disclosure. Additional cellular materials, such as fibroblasts, can also be administered, in some examples.

V. Methods of Monitoring the Efficacy of a Treatment for Muscular Dystrophy

Methods are also disclosed herein to monitor the efficacy of a treatment for muscular dystrophy. In some examples, the method of determining the effectiveness of an agent for the treatment of muscular dystrophy in a subject with muscular dystrophy includes detecting one or more disclosed muscular dystrophy-associated molecules in a sample from the subject following treatment with the agent; and comparing expression of such molecules following treatment to a reference value or control, wherein an alteration, such as a decrease or an increase, in the expression of the one or more muscular dystrophy-associated molecules following treatment indicates that the agent is effective for the treatment of muscular dystrophy in the subject. In some examples, these methods utilize a biological fluid, such as, but not limited to urine or serum, for the detection of a molecule associated with muscular dystrophy, including, but not limited to, disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) or any combination thereof. The methods include detecting, or determining the abundance (amount) or activity of one or more molecules associated with muscular dystrophy, including those disclosed herein.

The disclosed methods can include detecting at least one, such as two, three, four, five, six, seven, eight, nine, ten, eleven, or more molecules associated with muscular dystrophy. In one example, the method includes detecting at least one, such as two, three, four, five, six, seven, eight, nine, ten, eleven, twelve or thirteen of the following molecules associated with muscular dystrophy: disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2). In some examples, the methods include detecting at least Galectin-3. In some examples, the methods include detecting at least Galectin-1.

In some embodiments, the method includes detecting a decrease, such as a statistically significant decrease, such as an at least a 1.5, 2, 3, 4, or 5 fold decrease in the amount of one or more molecules associated with muscular dystrophy, including at least a 1.5, 2, 3, 4, or 5 fold decrease in one or more of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) as compared to a reference value.

In some embodiments, the method includes detecting a decrease, such as a statistically significant decrease, such as an at least 10% increase, including an at least 15%, at least 20%, at least 25%, at least 30%, at least 40%, at least 45%, at least 50%, at least 60%, at least 70%, at least 80%, at least 90%, including a 10% to 90% decrease, 20% to 80% decrease, 30% to 70% decrease or a 40% to 60% decrease (e.g., a 10%, 20%, 30%, 40%, 50%, 60%, 70%, 80%, 90%, 95%, 100%, 200% or more decrease) in the amount of one or more molecules associated with muscular dystrophy, including an at least a 10% decrease, including an at least 15%, at least 20%, at least 25%, at least 30%, at least 40%, at least 45%, at least 50%, at least 60%, at least 70%, at least 80%, at least 90%, including a 10% to 90% decrease, 20% to 80% decrease, 30% to 70% decrease or a 40% to 60% decrease (e.g., a 10%, 20%, 30%, 40%, 50%, 60%, 70%, 80%, 90%, 95%, 100%, 200% or more decrease) in one or more of disintegrin and metalloproteinase with thrombospondin motifs 5 (Adamts5), agrin (Agra), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) as compared to a reference value.

In some embodiments, the method includes detecting an increase, such as a statistically significant increase, such as an at least a 1.5, 2, 3, 4, or 5 fold increase in the amount of one or more molecules associated with muscular dystrophy, including at least a 1.5, 2, 3, 4, or 5 fold increase in one or more of disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) as compared to a reference value.

In some embodiments, the method includes detecting an increase, such as a statistically significant increase, such as an at least 10% increase, including an at least 15%, at least 20%, at least 25%, at least 30%, at least 40%, at least 45%, at least 50%, at least 60%, at least 70%, at least 80%, at least 90%, including a 10% to 90% increase, 20% to 80% increase, 30% to 70% increase or a 40% to 60% increase (e.g., a 10%, 20%, 30%, 40%, 50%, 60%, 70%, 80%, 90%, 95%, 100%, 200% or more increase) in the amount of one or more molecules associated with muscular dystrophy, including an at least a 10% increase, including an at least 15%, at least 20%, at least 25%, at least 30%, at least 40%, at least 45%, at least 50%, at least 60%, at least 70%, at least 80%, at least 90%, including a 10% to 90% increase, 20% to 80% increase, 30% to 70% increase or a 40% to 60% increase (e.g., a 10%, 20%, 30%, 40%, 50%, 60%, 70%, 80%, 90%, 95%, 100%, 200% or more increase) in one or more of the disclosed molecular dystrophy markers, such as Galectin-1 as compared to a reference value.

In some embodiments, the methods can be performed over time, to monitor the progression or regression of one or more signs or symptoms of muscular dystrophy in a subject, such as one or more signs or symptoms associated with DMD, LGMD, FHMD, BMD or MDC1A. The method can be performed multiple times over a specified time period, such as days, weeks, months or years. In several examples, the therapy includes treatment with an agent for muscular dystrophy. If the reference sample is a normal sample, and the test sample reading (e.g., expression or activity level of an evaluated muscular dystrophy-associated molecule) is essentially the same as the normal sample the subject is determined to have an effective therapy, while if the test sample has a significantly greater value for an evaluated muscular dystrophy-associated molecule relative to the normal sample, the subject is determined to have an ineffective therapy. Changes in the profile can also represent the progression (or regression) of the disease process. The subject can be monitored while undergoing treatment using the methods described herein in order to assess the efficacy of the treatment protocol. Following the measurement of the expression levels of one or more of the molecules identified herein, the assay results, findings, diagnoses, predictions and/or treatment recommendations can be recorded and communicated to technicians, physicians and/or patients, for example. In certain embodiments, computers are used to communicate such information to interested parties, such as, patients and/or the attending physicians. Based on the measurement, the therapy administered to a subject is modified. For example, the dose or dosing regimen is modified based on the information obtained using the methods disclosed herein.

In one embodiment, a diagnosis, prediction and/or treatment recommendation based on the expression level in a test subject of one or more of the muscular dystrophy-associated molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

VI. Methods of Identifying Agents for Treating Muscular Dystrophy

Methods are provided herein for identifying agents to treating muscular dystrophy, such as DMD, LGMD, FHMD, BMD and MDC1A. In some examples, the method of includes contacting a sample, such as a blood or urine sample, with one or more test agents under conditions sufficient for the one or more test agents to decrease the expression or biological activity of one or more of the disclosed muscular dystrophy-associated molecules. The method can also include detecting expression or biological activity of the one or more disclosed muscular dystrophy-associated molecules in the presence of the one or more test agents. The expression or biological activity of the one or more disclosed muscular dystrophy-associated molecules in the presence of the one or more test agents is then compared to a control, such as a reference value to determine if there is an alteration in expression or activity of the one or more disclosed muscular dystrophy-associated molecules, wherein decreased activity or expression of the one or more disclosed muscular dystrophy-associated molecules indicates that the one or more test agents is of use to treat the muscular dystrophy.

In one example, determining whether there is differential expression of one or more muscular dystrophy-associated molecules is by use of an in vitro assay. For example, an in vitro assay can be employed to compare expression of one or more muscular dystrophy-associated molecules in a sample, such as a blood or urine sample, in the presence and absence of the test agent. Expression levels can be determined by methods known to those of skill in the art including real time quantitative polymerase chain reaction, microarray analysis or Western blot analysis. In some examples, an at least 2-fold, at least 3-fold, or at least 5-fold, decrease in the activity of one or more disclosed muscular dystrophy-associated molecules in the presence of the one or more test agents as compared to the reference value indicates the one or more test agents is of use to treat muscular dystrophy. In some examples, an at least 2-fold, at least 3-fold, or at least 5-fold, increase in the activity of one or more disclosed muscular dystrophy-associated molecules in the presence of the one or more test agents as compared to the reference value indicates the one or more test agents is of use to treat muscular dystrophy.

Test Agents

The one or more test agents can be any substance, including, but not limited to, a protein (such as an antibody), a nucleic acid molecule (such as a siRNA), an organic compound, an inorganic compound, a small molecule or any other molecule of interest. In a particular example, the test agent is a siRNA that reduces or inhibits the activity (such as the expression) of one of the disclosed muscular dystrophy-associated molecules, such as disintegrin and metalloproteinase with thrombospondin motifs 5 (Adamts5), agrin (Agrn), collagen 6A1 (Col6a1), Galectin-3, matrix metalloproteinase 2 (Mmp2), integrin $\alpha3$ (Iga3), integrin $\alpha6$ (Iga6), integrin $\alpha7$ (Iga7), laminin-$\alpha4$ (Lama4), laminin-$\alpha5$ (Lama5), nidogen 1 (Nid1), tenascin C (Tnc), tissue inhibitor of metalloproteinase 1 (Timp1), tissue inhibitor of metalloproteinase 2 (Timp2). For example, the siRNA is directed to Galectin-3.

In other examples, the test agent is an antibody. For example, the antibody is directed to specifically bind to one of the disclosed muscular dystrophy-associated molecules, such as disintegrin and metalloproteinase with thrombospondin motifs 5 (Adamts5), agrin (Agrn), collagen 6A1 (Col6a1), Galectin-1, Galectin-3, matrix metalloproteinase 2 (Mmp2), integrin $\alpha3$ (Iga3), integrin $\alpha6$ (Iga6), integrin $\alpha7$ (Iga7), laminin-$\alpha4$ (Lama4), laminin-$\alpha5$ (Lama5), nidogen 1 (Nid1), tenascin C (Tnc), tissue inhibitor of metalloproteinase 1 (Timp1), tissue inhibitor of metalloproteinase 2 (Timp2). In a particular example, the antibody is directed to Galectin-1 or Galectin-3.

Disclosed test agents also include aptamers. In one example, an aptamer is a single stranded nucleic acid molecule (such as, DNA or RNA) that assumes a specific, sequence dependent shape and binds to a target protein (e.g., Galectin-1 or Galectin-3) with high affinity and specificity. Aptamers generally comprise fewer than 100 nucleotides, fewer than 75 nucleotides, or fewer than 50 nucleotides (such as 10 to 95 nucleotides, 25 to 80 nucleotides, 30 to 75 nucleotides, or 25 to 50 nucleotides). In a specific embodiment, a disclosed diagnostic specific binding reagent is a mirror image aptamer (also called a SPIEGELMER™). Mirror image aptamers are high affinity L enantiomeric nucleic acids (for example, L ribose or L 2'-deoxyribose units) that display high resistance to enzymatic degradation compared with D oligonucleotides (such as, aptamers). The target binding properties of aptamers and mirror image aptamers are designed by an in vitro selection process starting from a random pool of oligonucleotides, as described for example, in Wlotzka et al., *Proc. Natl. Acad. Sci.* 99(13):8898 8902, 2002. Methods of generating aptamers are known in the art (see e.g., Fitzwater and Polisky (Methods Enzymol., 267:275-301, 1996; Murphy et al., *Nucl. Acids Res.* 31:e110, 2003).

In another example, an aptamer is a peptide aptamer that binds to a target protein (e.g., a Galectin-1 or Galectin-3) with high affinity and specificity. Peptide aptamers can include a peptide loop (e.g., which is specific for Galectin-1 or Galectin-3) attached at both ends to a protein scaffold. This double structural constraint greatly increases the binding affinity of the peptide aptamer to levels comparable to an antibody's (nanomolar range). The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

VII. Kits

Provided by this disclosure are kits that can be used to diagnose, prognose or treat muscular dystrophy. For example, a kit is disclosed herein for diagnosing or prognosing muscular dystrophy, such as DMD, LGMD, FHMD, BMD or MDC1A, by reducing or inhibiting one or more symptoms associated with the muscular dystrophy in which the kit includes at least one agent capable of altering the expression or biological activity of one or more of the disclosed muscular dystrophy-associated molecules. The disclosed kits can include instructional materials disclosing means of use of the compositions in the kit. The instructional materials can be written, in an electronic form (such as a computer diskette or compact disk) or can be visual (such as video files). For example, instructions indicate to first perform a baseline measurement of a particular activity, such as measuring expression levels of one or more of the disclosed muscular dystrophy-associated molecules, such as Galectin-1 or Galectin-3. Then, administer a composition known to regulate such molecules according to the teachings herein. Administration is followed by re-measuring the particular activity. The activity level prior to treatment is compared to activity observed following treatment. An alteration in activity of at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to such activity in the absence of the composition indicates an effective treatment. In particular embodiments, a greater than 50% alteration indicates an effective treatment. An effective treatment can include, but are not limited to, an increase in patient survival, a slowing of the progression of the particular type of muscular dystrophy, a good prognosis, or a prevention of further muscle damage.

Kits are provided that can be used in the therapy assays disclosed herein. For example, kits can include one or more compositions, agents (such as antibodies) capable of detecting one or more of the muscular dystrophy biomarkers (for example, measuring Galectin-1 or Galectin-3, or combinations thereof). One skilled in the art will appreciate that the kits can include other agents to facilitate the particular application for which the kit is designed.

In one example, a kit is provided for treating DMD. For example, such kits can include one or more compositions capable of targeting inhibiting or reducing Galectin-3 activity or expression.

In some examples, a kit is provided for detecting one or more of the disclosed muscular dystrophy biomarkers in a biological sample. Kits for detecting muscular dystrophy-associated molecules can include one or more probes that specifically bind to the molecules. In an example, a kit includes an array with one or more of disintegrin and metalloproteinase with thrombospondin motifs 5 (Adamts5), agrin (Agra), collagen 6A1 (Col6a1), Galectin-1, Galectin-3, matrix metalloproteinase 2 (Mmp2), integrin α3 (Iga3), integrin α6 (Iga6), integrin α7 (Iga7), laminin-α4 (Lama4), laminin-α5 (Lama5), nidogen 1 (Nid1), tenascin C (Tnc), tissue inhibitor of metalloproteinase 1 (Timp1), tissue inhibitor of metalloproteinase 2 (Timp2) or any combination thereof and controls, such as positive and negative controls. In other examples, kits include antibodies that specifically bind to one of the muscular dystrophy-associated biomarkers disclosed herein. In some examples, the antibody is labeled (for example, with a fluorescent, radioactive, or an enzymatic label). Such a diagnostic kit can additionally contain means of detecting a label (such as enzyme substrates for enzymatic labels, filter sets to detect fluorescent labels, appropriate secondary labels such as a secondary antibody, or the like), as well as buffers and other reagents routinely used for the practice of a particular diagnostic method. In some examples, a kit includes at least one probe or antibody that specifically binds to Galectin-3 and the kit is used to diagnose or prognose DMD, LGMD, FHMD, BMD or MDC1A. In some examples, a kit includes at least one probe or antibody that specifically binds to Galectin-3 and the kit is used to prognose DMD and/or determine the efficacy of a treatment for DMD.

The disclosure is further illustrated by the following non-limiting Examples.

EXAMPLES

Example 1

Biomarkers for MDC1A

This example investigates the use of Galectin-1 and Galectin-3 a biomarkers for MDC1A.

i. Materials and Methods

Western Blotting.

Gastrocnemius muscles from 4- and 8-week old male wild-type and $dy^W$–/– animals were pulverized with a mortar and pestle cooled in liquid nitrogen. Protein was extracted from both serum and muscle tissue in RIPA buffer (50 mM Hepes pH 7.4, 150 mM NaCl, 1 mM $Na_3VO_4$, 10 mM NaF, 0.5% Triton X-100, 0.5% NP50, 10% glycerol, 2 mM PMSF and a 1:200 dilution of Protease Inhibitor Cocktail Set III) and quantified using a Bradford assay (Bio-Rad Laboratories Inc, Herculues, Calif.). Proteins were separated by SDS-PAGE. Galectin-1 was detected using a 1:1000 dilution of anti-Galectin-1 antibody (H00003956-D01P Abnova, Walnut, Calif.). Galectin-3 was detected using a 1:1000 dilution of anti-galecin-3 antibody (ab53082, Abcam). Blots were incubated with primary antibody overnight at 4° C. Blots were then incubated with a 1:5000 dilution of goat-anti-rabbit-IgG secondary antibody (Li-Cor Biosciences, Lincoln, Nebr.) for 1 hour. Blots were imaged using an Odyssey Imaging System and bands were quantified using the same system. Tissue blots were normalized to α-tubulin using a 1:5000 dilution of anti-α-tubulin (AbCam, Cambridge, Mass.) followed by a goat-anti-mouse-IgG (Li-Cor Biosciences, Lincoln, Nebr.).

Immunofluorescence.

Cryosections (8 mm) of 4- and 8-week old male tibialis anterior (TA) muscles were cut using a LeicaCM 1850 cryostat and mounted onto pre-cleaned Surgipath slides. Sections were fixed using 4% paraformaldehyde (PFA) for 5 minutes then rehydrated using PBS. Slides were blocked in 5% BSA in PBS then incubated with a 1:500 dilution of ab53082 (AbCam) for 1 hour. Slides were then incubated with a 1:1000 dilution of FITC-conjugated anti-rabbit-IgG antibody for 1 hour. Slides were mounted using Vectashield with DAPI and imaged using a Zeiss Axioskop 2 plus fluorescence microscope. Images were captured using a Zeiss AxioCam HRc digital camera with Axiovision 4.1 software.

Quantitative Real-Time PCR Analysis.

Total RNA was purified from five 4- and 8-week old male wild-type and $dy^{W}$–/– grastrocnemius muscles using Trizol (Invitrogen, Carlsbad, Calif.) reagent. After the concentration was determined, mRNA was pooled equally by genotype for cDNA production. The cDNA was prepared from 3 μg of pooled total RNA with random hexamers and Superscript III (Invitrogen, Carlsbad, Calif.) using standard procedures. Quantitative real-time PCR was conducted with 50 pg total cDNA using SYBR Green Jumpstart (Sigma-Aldrich, St Louis, Mo.) with Lgals1 primer sequences and Lgals3 primer sequences and levels were normalized to that of Gapdh.

Statistics.

Figure 1B:
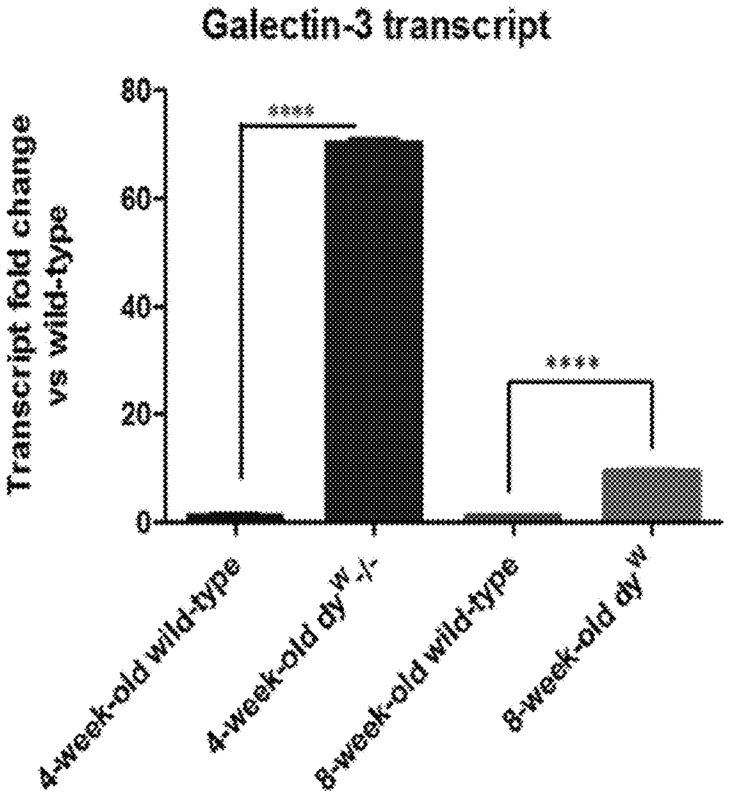

The fold change over wild-type was calculated using the ΔΔCt method after normalization and the average fold change in transcript and (±s.e.m.) were calculated. One and two way ANOVA with a Bonferroni post test correction were used to determine statistical significance using GraphPad Prism ii. Results Quantitative Real-Time PCR was used to determine changes in the transcription of Lgals1 and Lgals3 (FIGS. 1A-1B). Both 4- and 8-week old dystrophic mice had significantly increased transcripts of Lgals3 compared to age-matched wild-type mice. The 4-week old mice had 70.02 fold increase in Galectin-3 transcript compared to wild-type animals. Lgals3 transcription was reduced in the 8-week old mice; however, it was still significantly elevated 9.37 fold compared to wild-type animals (FIG. 1B). These results indicate the loss of laminin-α2 resulted in increased transcription of Galectin-3 and that transcription levels drop as the dystrophic mice age.

Both 4- and 8-week old dystrophic mice had significantly increased transcripts of Lgals1 compared to age-matched wild-type animals as well. The 4-week old mice had a 9.19 fold increase in Galectin-1 transcript compared to wild-type animals. Lgals1 transcription was reduced in the 8-week old mice; however, it was still significantly elevated 1.7 fold compared to wild-type animals (FIG. 1A). These results indicate the loss of laminin-α2 results in increased transcription of Galectin-1 and that transcription levels drop as the dystrophic mice age.

Figure 2A:
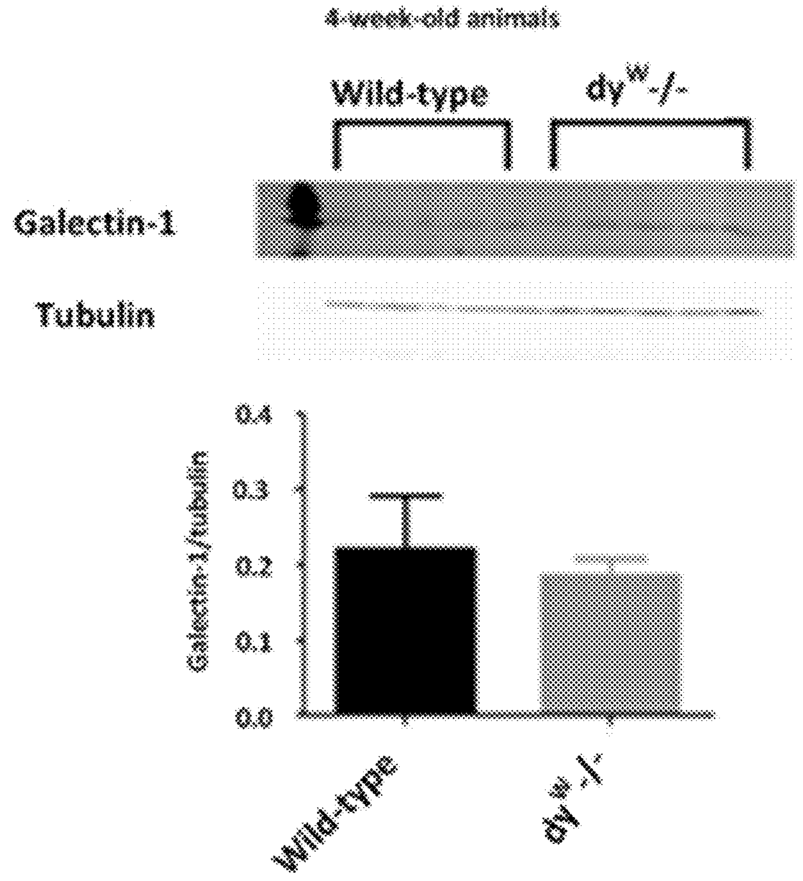

Western blotting analysis revealed no significant difference in Galectin-1 protein levels in 4- or 8-week old $dy^{W}$–/– animals when compared to age-matched wild-type animals (FIGS. 2A and 2B, respectively). There was also no significant difference between the Galectin-1 protein when comparing 4- and 8-week old $dy^{W}$–/– animals (FIG. 2C).

Figure 3A:
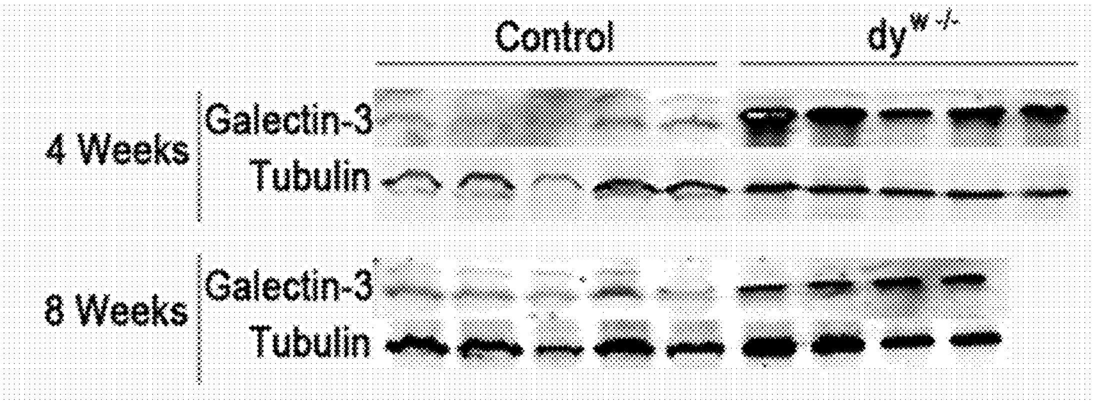
FIG. 3A is a digital image of Western blotting results for Galectin-3 in the $dy^W$–/– and wild-type mice at 4- and 8-weeks of age.
Figure 3B:
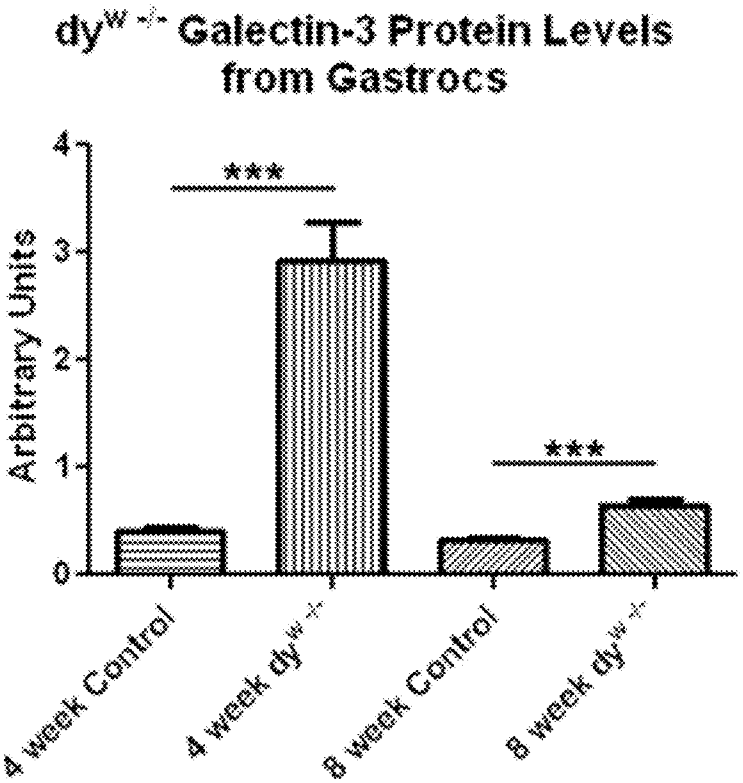
FIG. 3B is a bar graph quantitating the level of Galectin-3 protein in the grostocnemius muscle of 4-week old and 8-week old $dy^W$–/– animals as compared to wild type (control) mice.

Western blotting analysis for Galectin-3 protein revealed significantly more Galectin-3 protein in 4-week old $dy^{W}$–/– animals compared to age-matched wild-type animals (FIGS. 3A and 3B) and 8-week old $dy^{W}$–/– animals compared to age-matched wild-type animals.

Figure 4A:
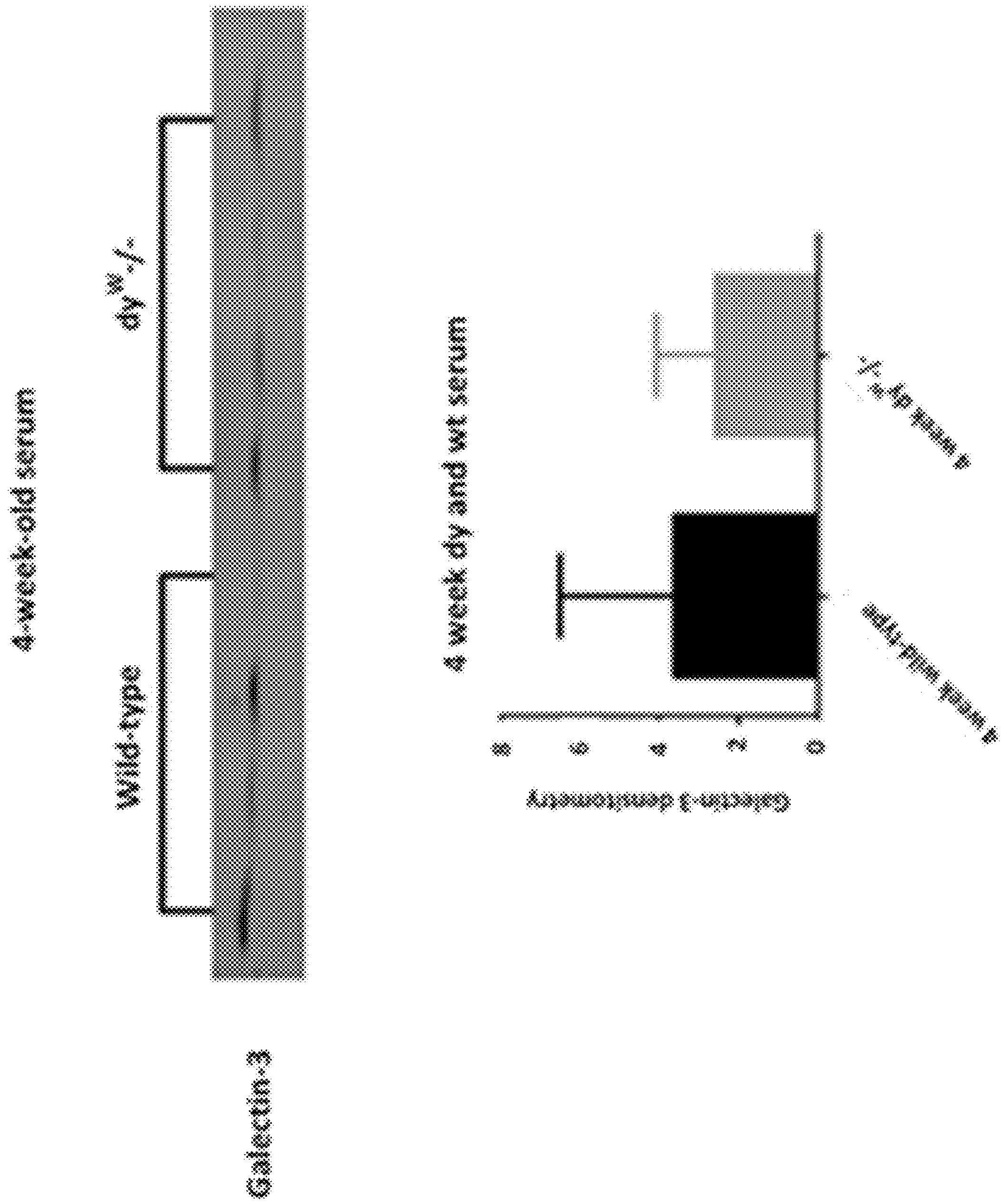
FIGS. 4A and 4B are digital images and bar graphs illustrating Western blotting studies for Galectin-3 in the serum $dy^W$–/– and wild-type mice at 4- and 8-weeks of age.
Figure 4B:
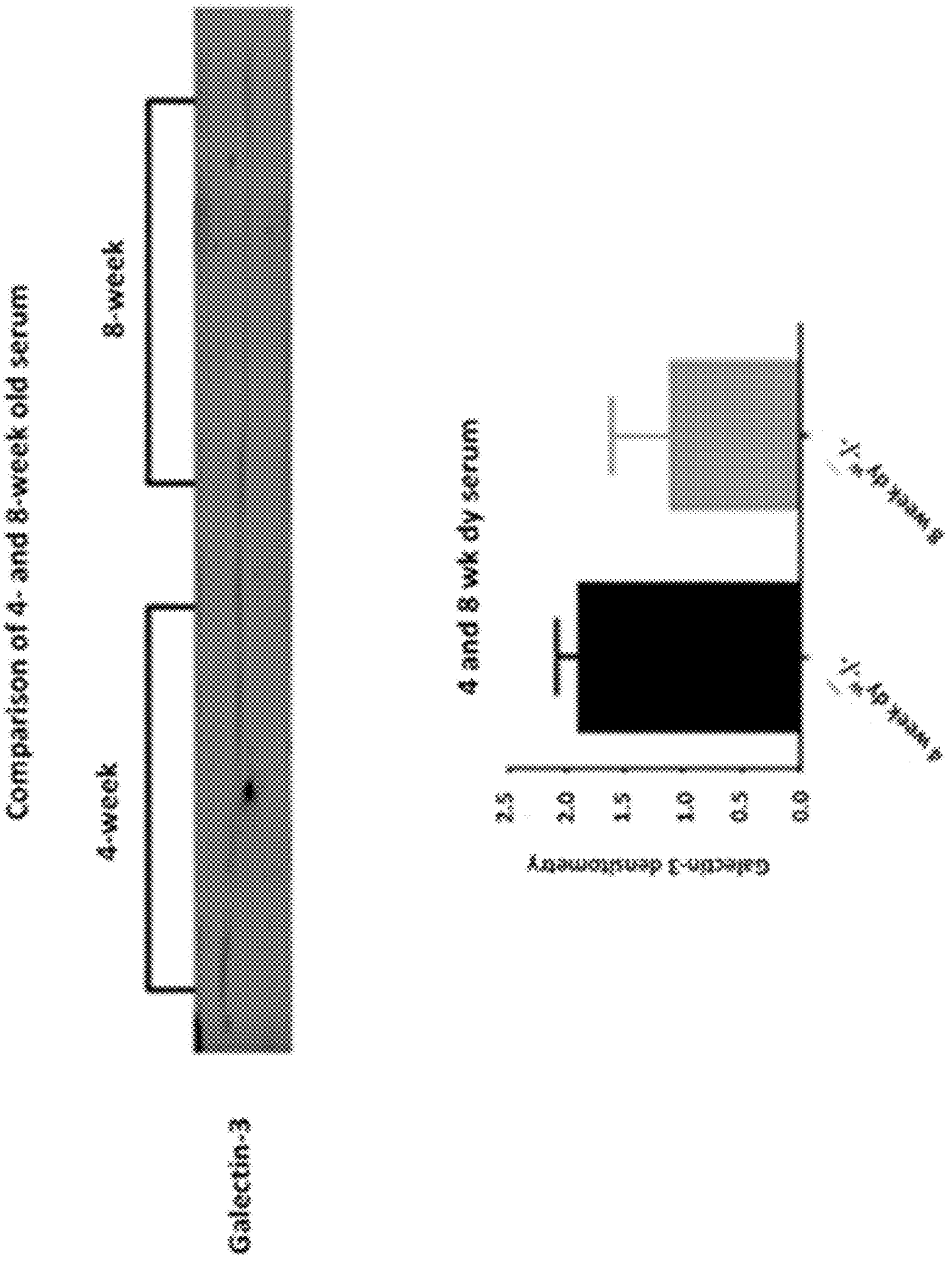

Western blotting on serum revealed no significant difference in Galectin-3 protein between 4-week old $dy^{W}$–/– mice and age-matched wild-type mice (FIG. 4A). In addition, serum western blots showed significantly more Galectin-3 protein in 4-week old $dy^{W}$–/– mice than 8-week old $dy^{W}$–/– mice (FIG. 4B). These results revealed that the amount of Galectin-3 released into the blood stream is different than that held in the muscle.

Figure 5:
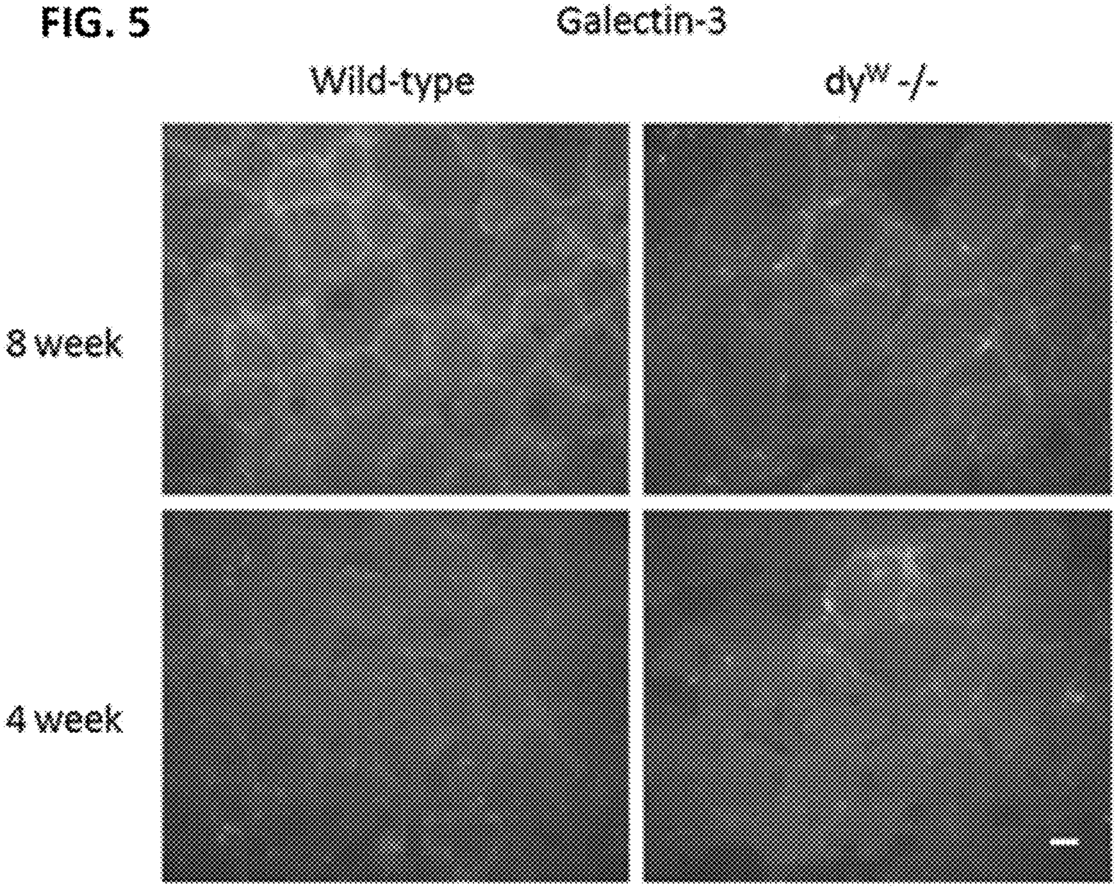
FIG. 5 is a series of digital images of Galectin-3 immunofluorescence on 4- and 8-week $dy^W$–/– and wild-type mice. Immunofluorescence was used to evaluate Galectin-3 levels in the tibialis anterior muscle of mice. Galectin-3 was found to be elevated in 4-week old $dy^W$–/– mice when compared to that in the wild-type mice. Galectin-3 was found to be similar in 8-week $dy^W$–/– mice and wild-type mice. Galectin-3 levels were also found to be similar between 4- and 8-week old $dy^W$–/– mice. Galectin-3 levels appear to increase in the wild-type mice as they age.

Immunofluorescence for Galectin-3 was also completed on the tibialis anterior muscle of 4- and 8-week old $dy^{W}$–/– mice and wild-type mice. Immunofluorescence revealed a similar pattern as to that shown in the tissue western blots. 4-week old $dy^{W}$–/– mice had elevated levels of Galectin-3 compared to age-matched wild-type animals. Galectin-3 levels appeared to be similar in 4- and 8-week old $dy^{W}$–/– mice as well as between 8-week old $dy^{W}$–/– and age-matched wild-type mice. Galectin-3 levels also appeared to increase as the wild-type animals age (FIG. 5).

Although Galectin-1 transcript was significantly elevated in the $dy^{W}$–/– animals, this did not translate to an elevation in detectable Galectin-1 protein. These studies indicate that Galectin-1 is not a good candidate as a biomarker for the $dy^{W}$–/– mouse model of MDC1A. In contrast, Galectin-3 was significantly elevated at the transcript level of $dy^{W}$–/– mice, and at the protein level in the muscle, indicating its use as a biomarker of MDC1A.

Example 2

Biomarkers for DMD

This example demonstrates the use of Galectin-1 and Galectin-3 a biomarkers for DMD.

i. Materials and Methods

Western Blotting.

Gastrocnemius muscles from 2-, 5- and 10-week old male wild-type and mdx animals were pulverized with a mortar and pestle cooled in liquid nitrogen. Protein was extracted from both serum and muscle tissue in RIPA buffer (50 mM Hepes pH 7.4, 150 mM NaCl, 1 mM $Na_3VO_4$, 10 mM NaF, 0.5% Triton X-100, 0.5% NP50, 10% glycerol, 2 mM PMSF and a 1:200 dilution of Protease Inhibitor Cocktail Set III) and quantified using a Bradford assay (Bio-Rad Laboratories Inc, Herculues, Calif.). Proteins were separated by SDS-PAGE. Galectin-1 was detected using a 1:1000 dilution of anti-Galectin-1 antibody (H00003956-D01P Abnova, Walnut, Calif.). Galectin-3 was detected using a 1:1000 dilution of anti-galecin-3 antibody (ab53082, Abcam). Blots were incubated with primary antibody overnight at 4° C. Blots were then incubated with a 1:5000 dilution of goat-anti-rabbit-IgG secondary antibody (Li-Cor Biosciences, Lincoln, Nebr.) for 1 hour. Blots were imaged using an Odyssey Imaging System and bands were quantified using the same system. Blots were normalized to α-tubulin using a 1:5000 dilution of anti-α-tubulin (AbCam, Cambridge, Mass.) followed by a goat-anti-mouse-IgG (Li-Cor Biosciences, Lincol, Nebr.).

Immunofluorescence.

Cryosections (8 mm) of 5- and 10-week old male tibialis anterior (TA) muscles were cut using a LeicaCM 1850 cryostat and mounted onto pre-cleaned Surgipath slides. Sections were fixed using 4% paraformaldehyde (PFA) for 5 minutes then rehydrated suing PBS. Slides were blocked in 5% BSA in PBS then incubated with a 1:500 dilution of ab53082 (AbCam) for 1 hour. Slides were then incubated with a 1:1000 dilution of FITC-conjugated anti-rabbit-IgG antibody for 1 hour. Slides were mounted using Vectashield with DAPI and imaged using a Zeiss Axioskop 2 plus fluorescence microscope. Images were captured using a Zeiss AxioCam HRc digital camera with Axiovision 4.1 software.

Quantitative Real-Time PCR Analysis.

Total RNA was purified from five 5- and 10-week old male wild-type and mdx grastrocnemius muscles using Trizol (Invitrogen, Carlsbad, Calif.) reagent. After the concentration was determined, mRNA was pooled equally by genotype for cDNA production. The cDNA was prepared from 3 μg of pooled total RNA with random hexamers and Superscript HI (Invitrogen, Carlsbad, Calif.) using standard procedures. Quantitative real-time PCR was conducted with 50 pg total cDNA using SYBR Green Jumpstart (Sigma-Aldrich, St Louis, Mo.) with Lgals1 primer sequences and Lgals3 primer sequences (and levels were normalized to that of Gapdh.

Statistics.

The fold change over wild-type was calculated using the ΔΔCt method after normalization and the average fold change in transcript and (±s.e.m.) were calculated. One and two way ANOVA with a Bonferroni post test correction were used to determine statistical significance using GraphPad Prism.

ii. Results

Quantitative Real-Time-PCR was used to determine changes in the transcription of Lgals1 and Lgals3. Both 5- and 10-week old dystrophic mice had significantly increased transcripts of Lgals3 compared to age-matched wild-type mice. The 5-week old mice had an 11.42 fold increase in Galectin-3 transcript compared to wild-type animals, while the 10-week old mice had a 67.20 fold increase in Galectin-3 transcript compared to wild-type animals. Transcript levels of Lgals3 also increased from the 5-week old mdx mice (11.42 fold increase) to the 10-week old mdx mice (67.20 fold increase). These results indicate the loss of dystrophin resulted in increased transcription of Galectin-3 and that transcription levels increased as the dystrophic mice age.

Figure 6A:
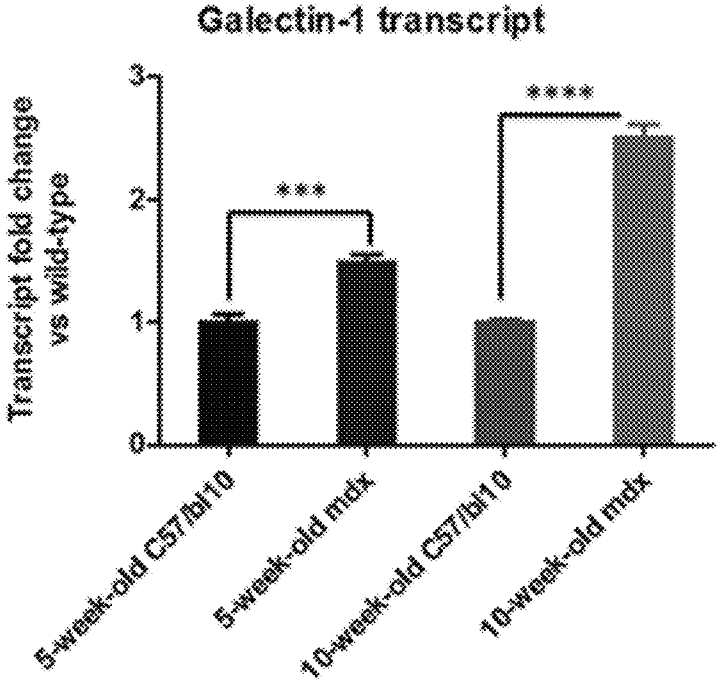
FIGS. 6A and 6B are bar graphs illustrating transcription of Lgals1 and Lgals3 were altered in the mdx mouse.
Figure 6B:
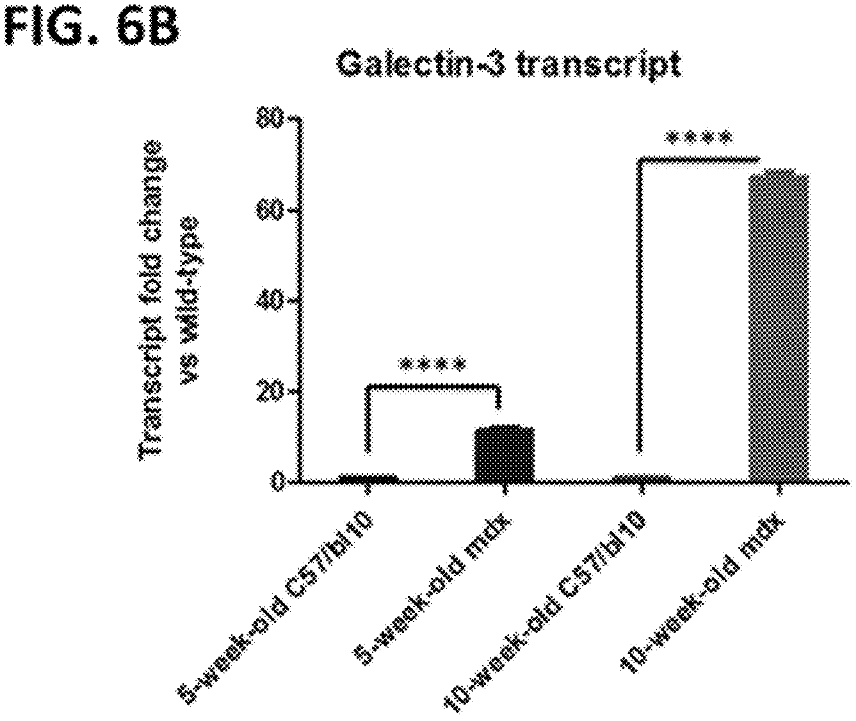

Only the 10-week old mdx mice had significantly increased levels of Lgals1 transcript compared to wild-type animals. The 5-week old mice had a 1.49 fold increase in Galectin-1 transcript, while the 10-week old dystrophic mice had a 2.51 fold increase in Galectin-1 transcript compared to wild-type animals. In addition, transcript levels of Lgals1 increased from the 5-week old mdx mice (1.49 fold increase) to the 10-week old mdx mice (2.51 fold increase) (FIG. 6). These results indicate the loss of dytstrophin resulted in increased transcription of Galectin-1 and that transcription levels increased as the dystrophic mice age.

Figure 7A:
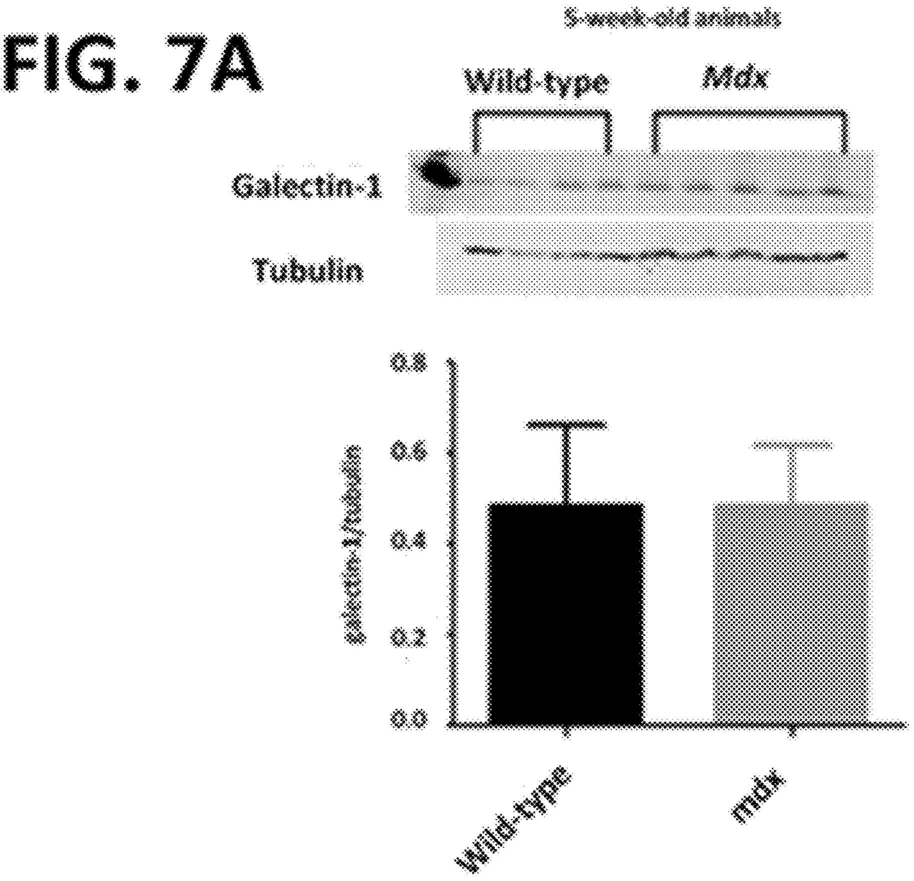
FIGS. 7A-7C are bar graphs and digital images of Western blotting results for Galectin-1 in mdx and wild-type mice at 2-, 5- and 10-weeks of age.
Figure 7B:
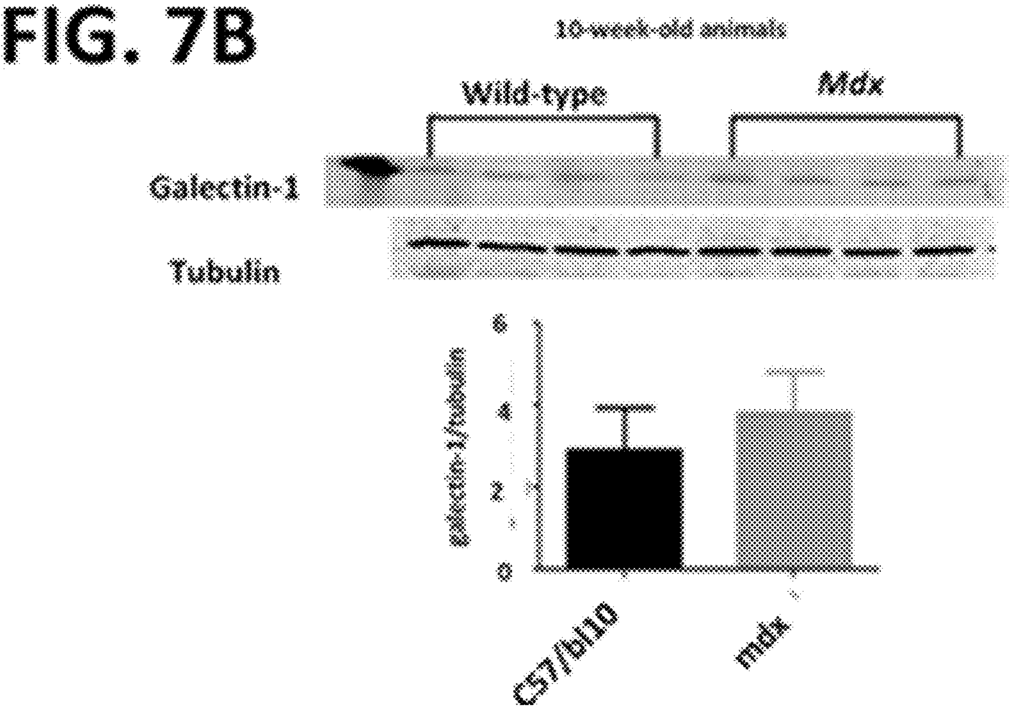
Figure 7C:
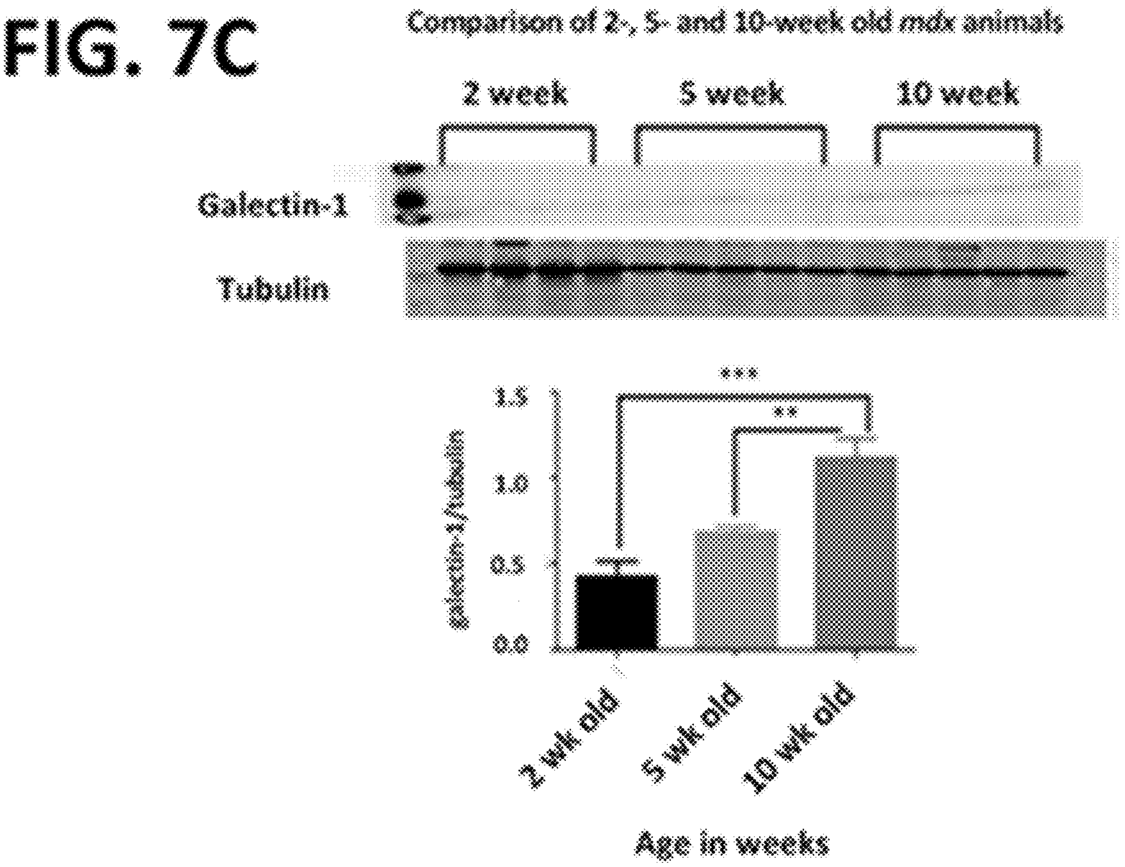

Western blotting analysis revealed no significant difference in Galectin-1 protein levels in the gastrocnemius muscle of 5- or 10-week old mdx animals when compared to age-matched wild-type animals (FIGS. 7A and 7B, respectively). There was, however, a significant difference between the Galectin-1 protein when comparing 2-, 5- and 10-week old mdx animals (FIG. 7C).

Figure 8A:
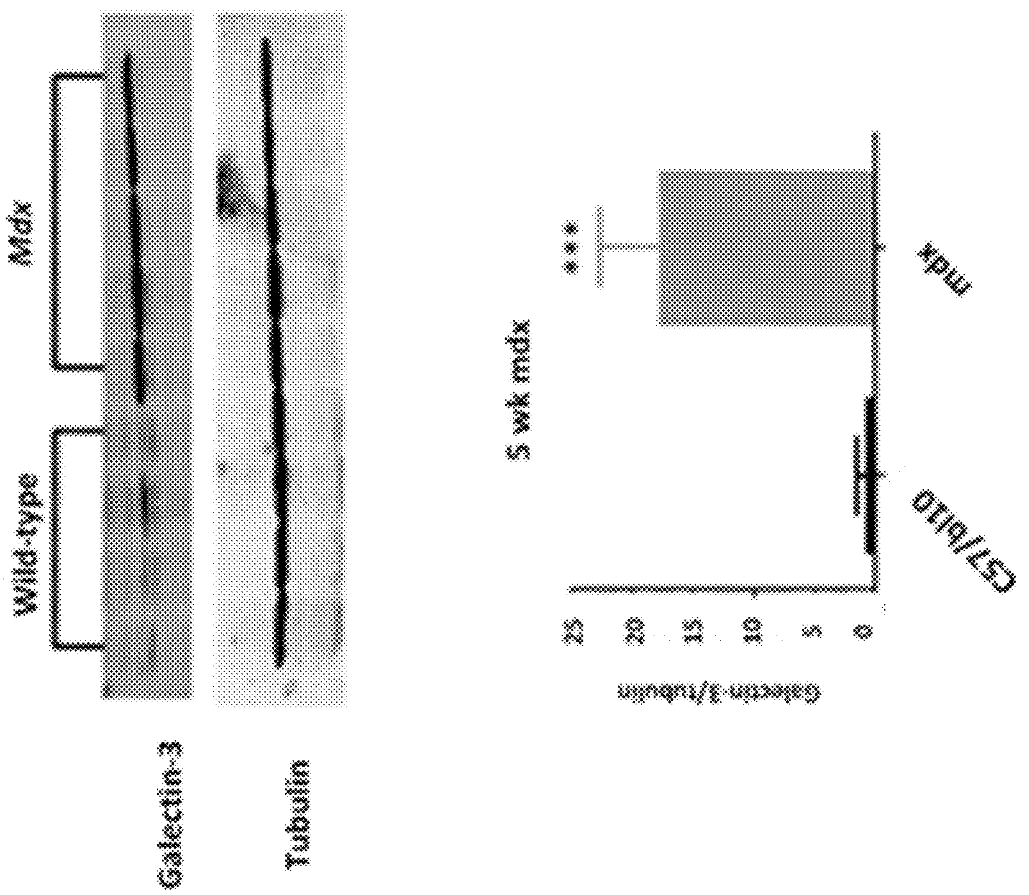
FIGS. 8A and 8B are bar graphs and digital images of Western blotting results for Galectin-3 in the mdx and wild-type mice at 5- and/or 10-weeks of age.
Figure 8B:
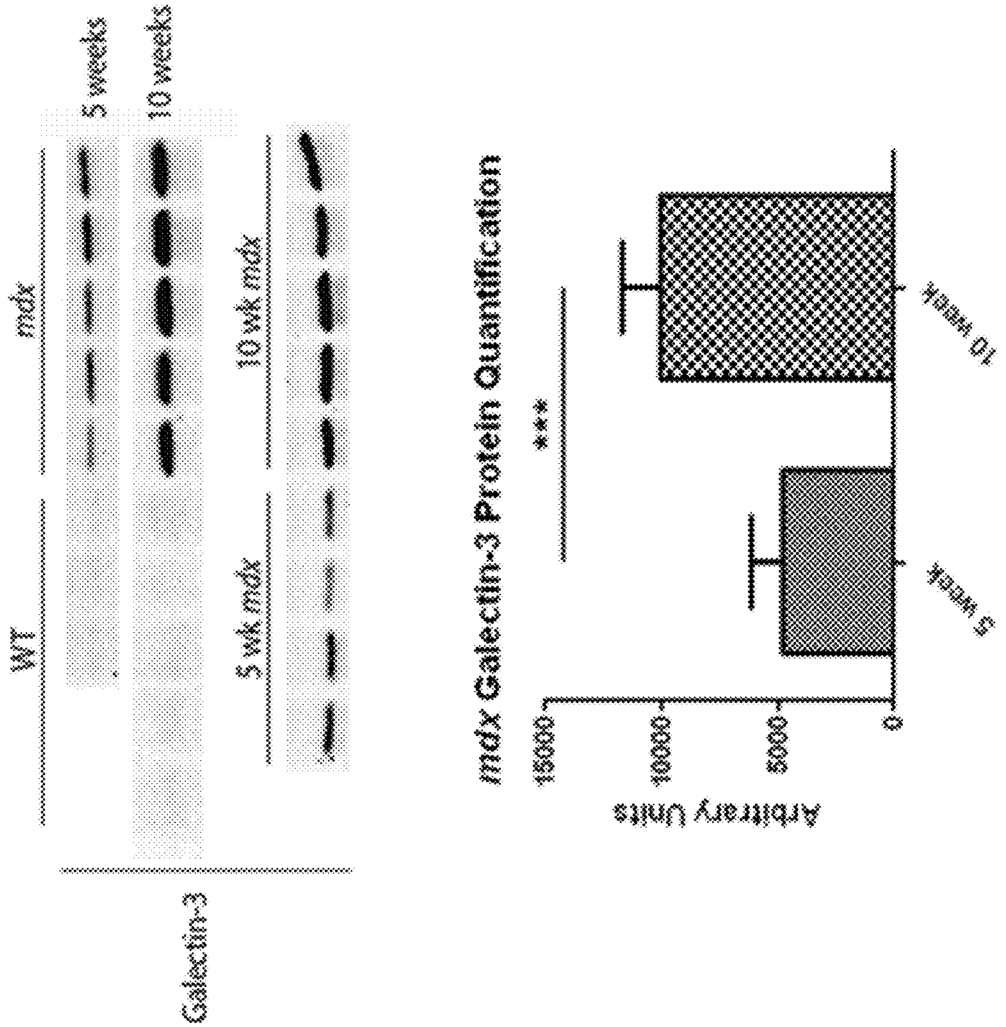

At 5-weeks of age, the mdx animals had significantly more Galectin-3 protein in the gastrocnemius muscle than the wild-type animals (FIG. 8A.). In addition, there was a significant difference in the Galectin-3 protein levels between 5- and 10-week old mdx animals (FIG. 8B).

Figure 9A:
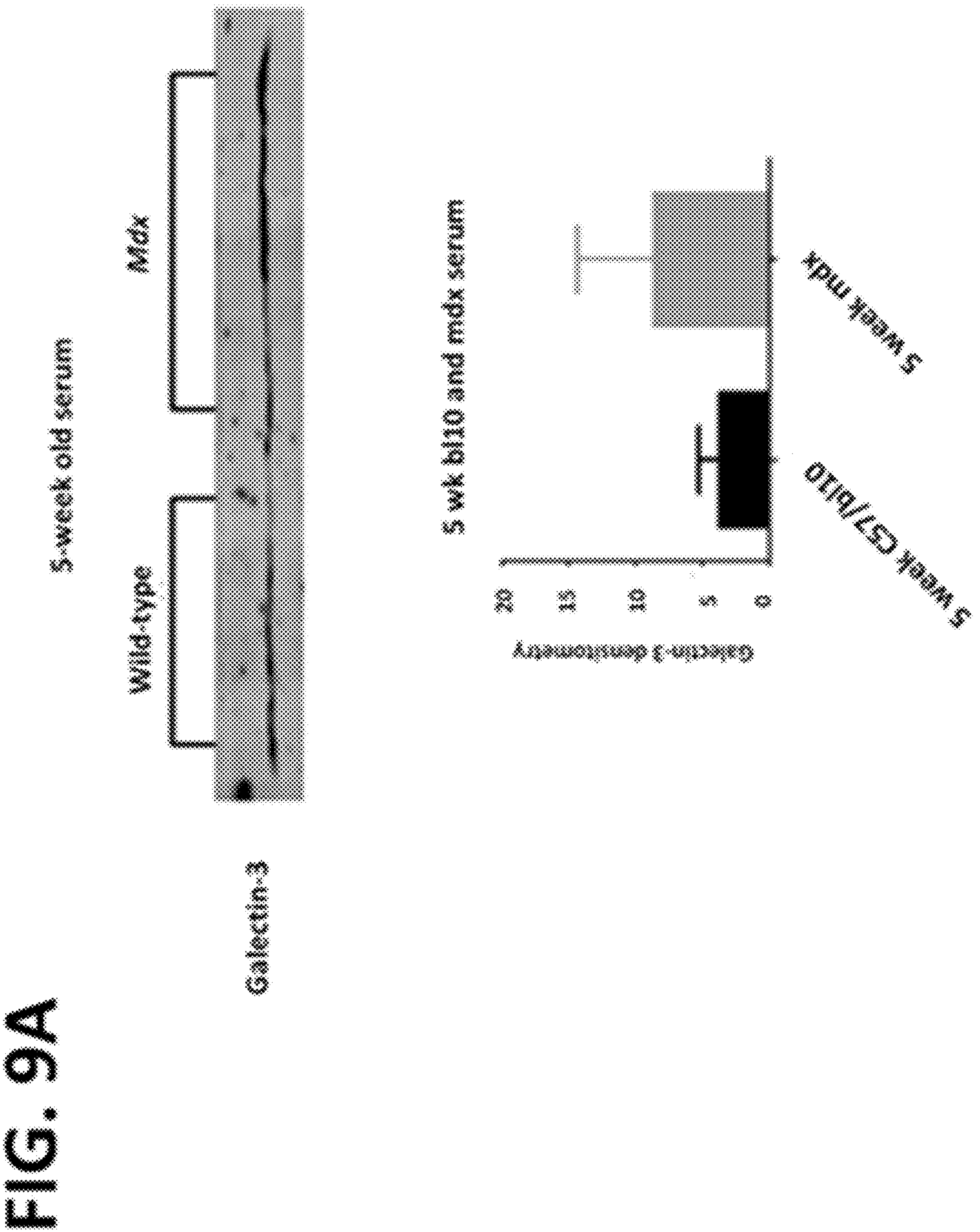
FIGS. 9A and 9B are bar graphs and digital images of Western blotting studies for Galectin-3 in the serum of mdx and wild-type mice at 5- and 10-weeks of age.
Figure 9B:
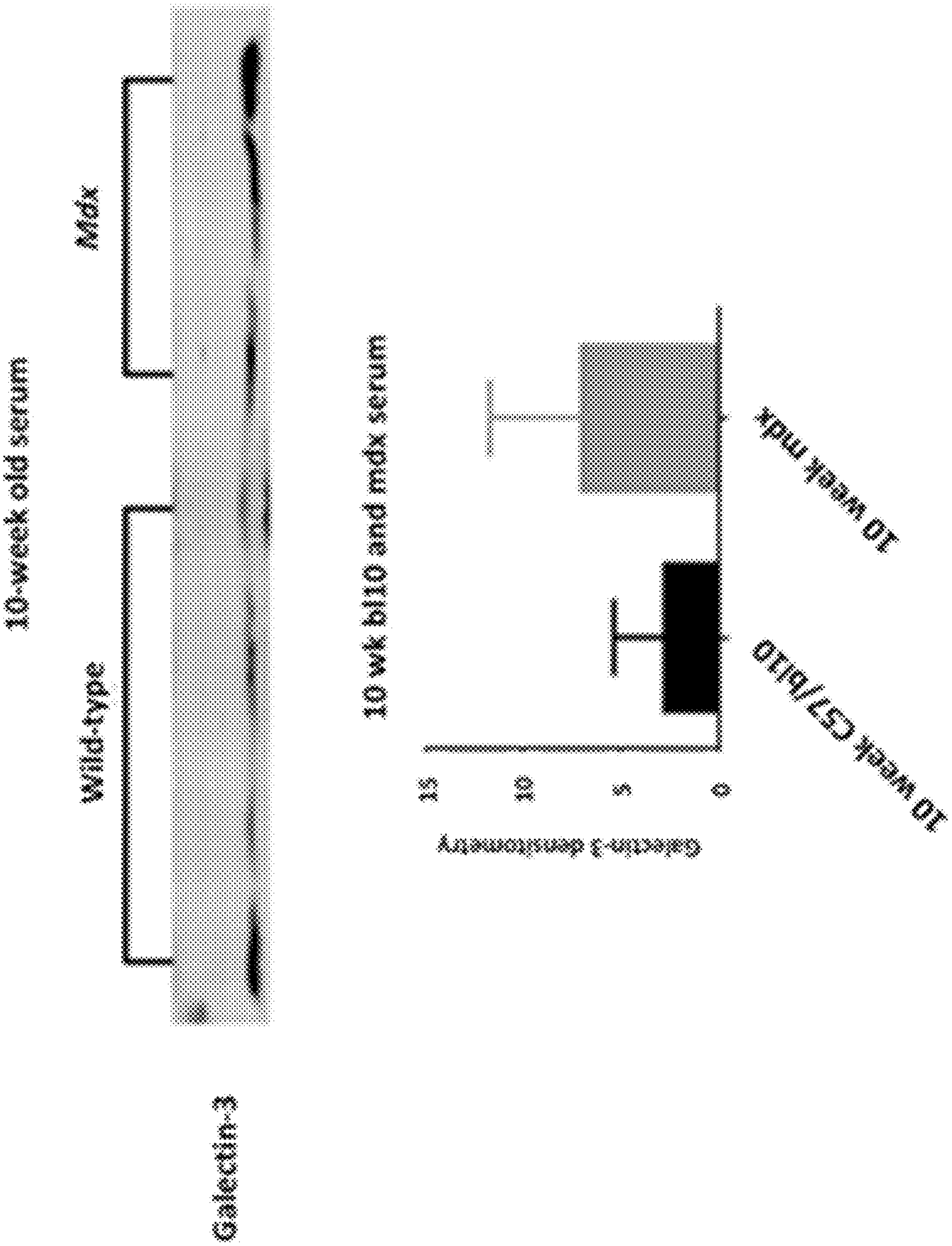

Western blotting on 5- and 10-week old mdx and wild-type serum revealed similar results to the tissue blots, although there was no significant difference in Galectin-3 protein levels (FIG. 9A and FIG. 9B, respectively). However, at both age points the mdx mice were trending towards more Galectin-3 protein.

Figure 10:
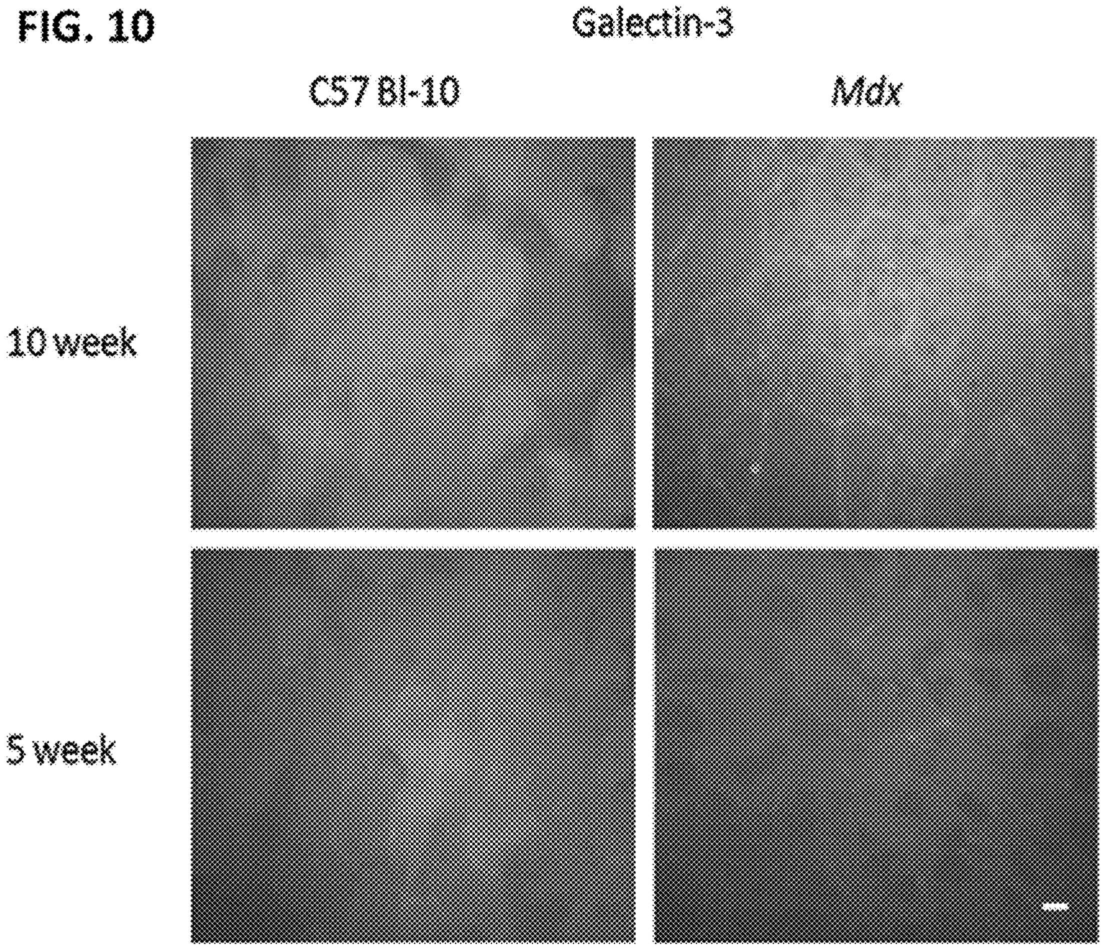
FIG. 10 is a series of digital images of Galectin-3 immunofluorescence on 5- and 10-week mdx and wild-type mice. Immunofluorescence was used to evaluate Galectin-3 levels in the tibialis anterior muscle. Galectin-3 was found to be elevated in 5- and 10-week old mdx mice when compared to that in the wild-type mice. Galectin-3 was found to be elevated in 10-week old mdx mice compared to that in the 5-week old mice while Galectin-3 levels were similar between 5- and 10-week wild-type mice.

Immunofluorescence for Galectin-3 was also completed on the tibialis anterior (TA) muscle of 5- and 10-week old mdx and wild-type mice. Immunofluorescence revealed a similar pattern as to that shown through western blotting. Both 5- and 10-week old mdx mice had elevated levels of Galectin-3 compared to age-matched wild-type animals. Galectin-3 levels also appeared to be elevated in 10-week old mdx mice compared to 5-week old mdx mice (FIG. 10).

These results revealed that although Galectin-1 transcript was significantly elevated in the mdx animals, is did not translate to an elevation in detectable Galectin-1 protein. Western blotting revealed no significant difference between Galectin-1 levels in mdx and wild-type mice, but a significant difference was seen between 5- and 10-week old mdx mice. A biomarker needs to not only follow the progression of the disease, but must also be differentiable from levels found in disease-free patients. As the results do anot reveal these differences in Galectin-1 levels, it is not a good candidate as a biomarker for the mdx mouse model of DMD.

In this study, however, Galectin-3 was significantly elevated at the transcript level of mdx mice, as well as at the protein level in the muscle. Galectin-3 was secreted by macrophages and monocytes, two cells seen in fibrosis, a hallmark of DMD. Therefore, these studies support the use of Galectin-3 as a biomarker for DMD.

Additional studies have been performed evaluating the levels of Galectin-3 in the muscle of the GRMD dog model of DMD. The GRMD model develops progressive and fatal muscle disease and has been shown to exhibit pathophysiological disease features identical to DMD including progressive loss of muscle function, muscle membrane fragility, cardiomyopathy and premature death (Kornegay et al., *Muscle Nerve* 11:1056-1064, 1988; Cooper et al., *Nature* 334:154-156, 1988). The GRMD dog model is generally accepted as the gold standard preclinical model to test therapeutics for DMD.

Figure 11:
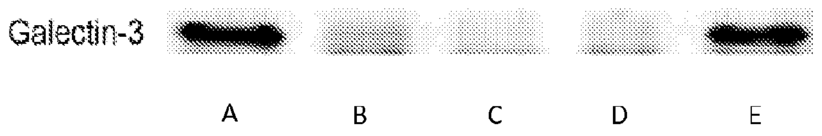
FIG. 11 is a digital image of a Western blot study for Galectin-3 levels in the muscle of the golden retriever muscular dystrophy (GRMD) dog model of DMD. Elevated levels of Galectin-3 protein are detected in the muscle of GRMD dogs, lanes A and E. Little or no Galectin-3 was observed in unaffected control dog samples, lanes B-D.

Western analysis revealed GRMD dogs had increased Galectin-3 levels in the Vastus lateralus muscle of GRMD as compared to control dogs (FIG. 11). Immunofluorescence studies revealed that Galectin-3 is found surrounding myofibers and associated with blood vessels of unaffected dogs. In sharp contrast, the amount of Galectin-3 increases in muscle and localization changes to discrete sites that are associated with smooth muscle actin positive regions which correspond to small blood vessels. In unaffected dogs, Galectin-3 was localized around myofibers and associated with large blood vessels within the endothelial/smooth muscle of such vessels. Loss of dystrophin in GRMD dogs resulted in higher levels of Galectin-3 with punctate staining in skeletal muscle tissue. There was also a loss of Galectin-3 localization from large muscle blood vessels to smaller blood vessels in GRMD dogs and the colocalization of Galectin-3 and smooth muscle actin was lost.

Galectin3 serum levels in wild-type and mdx mice were determined by ELISA (Table 3). There was very little variation in the wild-type (WT) control animals at all ages observed. Mdx animals exhibited a steady increase in average serum levels from 5 weeks to 10 weeks, when dystrophic pathology were most consistently observed. After 10 weeks there was variance in these animals. Exercise had no effect on the serum levels of 5-week old mdx mice.

TABLE 3

Galectin3 serum levels in wild-type and mdx mice.

| | Age (months) | Average Serum Level (ng/mL) | SEM | N |
|---|---|---|---|---|
| WT | 3.5 | 47.76 | 5.71 | 3 |
| C57BL/10 | 9.5 | 40.92 | 4.67 | 8 |
| | 10 | 52.09 | 5.62 | 7 |
| | 11 | 54.90 | 23.56 | 4 |
| | 12 | 50.97 | 5.70 | 10 |
| mdx | 1.25 | 45.40 | 11.05 | 8 |
| | 2 | 108.45 | 29.96 | 5 |
| | 3 | 120.11 | 21.04 | 15 |
| | 4.5 | 47.86 | 18.00 | 2 |
| | 5 | 86.55 | 45.58 | 2 |
| | 5.5 | 71.16 | 17.47 | 7 |
| | 6 | 301.90 | 153.33 | 5 |
| | 7.5 | 557.53 | 198.73 | 4 |
| | 8.5 | 141.38 | 76.98 | 3 |
| | 9 | 204.76 | 85.47 | 10 |
| | 9.5 | 207.63 | 176.75 | 2 |
| exercised mdx | 1.25 | 60.14 | 10.48 | 4 |

In addition, Galectin-3 serum levels were measured in MDC1A patients and compared to age matched controls (Table 4). Patients and controls were broken into age-matched categories by age or gender starting with up to three years in which patients had significantly higher serum levels then controls. After age 3, for both males and females, patients appear to have slightly lower serum levels. A final category for patients was based on a lack of muscular ability and these patients had the lowest serum levels. Table 5 provides a summary of the MDC1A patient data shown in Table 4.

TABLE 4

Galectin-3 serum analysis of MDC1A patients compared to age matched controls.

| | Galectin-3 pg/mL | Age | Gender | Muscular Abilities |
|---|---|---|---|---|
| Controls | 1845 | 0.9 | M | |
| | 3091 | 1.3 | M | |
| | 4867 | 1.5 | F | |
| | 4193 | 2.5 | F | |
| | 3441 | 2.7 | M | |
| | 2357 | 4.0 | F | |
| | 5825 | 5.9 | M | |
| | 6288 | 6.4 | M | |
| | 2185 | 7.3 | F | |
| | 5412 | 7.9 | M | |
| Patients | 5687 | 0.9 | M | good head control, unable to sit without assistance |
| | 1172 | 1.4 | M | briefly able to sit without assistance |
| | 7367 | 1.5 | F | sat without assistance |
| | 12263 | 1.7 | F | sat without assistance |
| | 5002 | 2.8 | M | sat without assistance |
| | 1549 | 3.9 | F | sat without assistance |
| | 4372 | 5.6 | M | sat without assistance |
| | 4417 | 6.5 | M | sat without assistance |
| | 3135 | 7.8 | M | sat without assistance |
| | 633 | 11.6 | F | good head control, unable to sit without assistance |

TABLE 5

Average Serum Levels of Galectin-3 in various patient populations.

| | Average Serum Levels (ng/mL) | N |
|---|---|---|
| Controls Under 3 | 3.49 | 5 (3M, 2F) |
| Patients Under 3 (mobile) | 7.58 | 4 (2M, 2F) |
| Patient Under 3 (non-mobile) | 1.17 | 1M |
| Male Controls Over 3 | 5.84 | 3 |
| Male Patients Over 3 (mobile) | 3.97 | 3 |
| Female Controls Over 3 | 2.27 | 2 |
| Female Patient Over 3 (mobile) | 1.55 | 1 |
| Female Patient Over 3 (non-mobile) | 0.63 | 1 |

The dyw−/− mouse has a bell shaped curve for Galectin-3 protein in muscle which peaks around 4 weeks and then falls by 8 weeks as the mice became less and less active due to muscle weakness. A similar pattern was observed in MDC1A patient serum compared to controls. Before the age of 3, the average serum level of Galectin-3 was over 2-fold higher than that in controls (~7.5 ng/mL compared to 3.5 ng/mL, respectively). However, after the age of 3 the levels were lower than gender matched controls. The observed decrease indicates a significant loss of muscle as supported by the fact that the two patients who were non-mobile and unable to sit without assistance had extremely low serum levels of Galectin-3. These studies further indicate a role of Galectin-3 in MD and a use of such to indicate the presence of MD. Additionally, for MDC1A, Galectin-3 serum levels are diagnostic before the age of 3 (high Gal-3 serum levels) and potentially prognostic for severe pathology (extremely low Gal-3 serum levels).

Example 3

Additional Biomarkers for MDC1A

This example describes possible biomarkers for MDC1A.

i. Material and Methods

Transgenic α7 Integrin $Dy^{W}$−/− Mice.

Transgenic α7 integrin $dy^{W}$−/− mice were generated by breeding mice that overexpressed the α7BX2 integrin in skeletal muscle with $dy^{W}$+/− animals. Resultant pups which were heterozygous for the laminin α2 mutant allele and positive for the α7 BX2 transgene were bred to $dy^{W}$+/− mice. The male pups from these matings included $dy^{W}$+/+; itga7-(wild-type), $dy^{W}$−/−; itga7-($dy^{W}$−/−) (laminin-α2 deficient) and $dy^{W}$−/−; itga7+(laminin-α2 deficient that overexpress the α7 BX2 integrin) mice. Male littermates were used as controls for all studies. Genomic DNA was isolated from tail biopsies taken at 10 days of age using the Wizard SV Genomic DNA Purification System (Promega, Madison, Wis.). Polymerase chain reaction (PCR) was used as previously described to detect the laminin-α2 allele and the α7 BX2 transgene.

Isolation of Skeletal Muscle.

Four-week-old wild-type, $dy^{W}$−/− and $dy^{W}$−/−; itga7+ male mice were sacrificed, Skeletal muscles were dissected and flash frozen in liquid nitrogen cooled isopentane. Tissues were stored at −80° C.

Western Blot Analysis.

Gastrocnemius muscles from 4 week old male mice were pulverized with a mortar and pestle cooled in liquid nitrogen. Protein was extracted in RIPA buffer (50 mM Hepes pH 7.4, 150 mM NaCl, 1 mM $Na_3VO_4$, 10 mM NaF, 0.5% Triton X-100, 0.5% NP50, 10% glycerol, 2 mM PMSF and a 1:200 dilution of Protease Inhibitor Cocktail Set III) and quantified by a Bradford assay (Bio-Rad Laboratories Inc, Hercules, Calif.). Proteins were separated by SDS-PAGE. The α7 integrin was detected with a 1:1000 dilution of anti-α7B antibody overnight. Integrin α7A was detected using 1:1000 dilution of CDB 345 antibody overnight. Integrin α3 was quantified using AB1920 antibody (Chemicon). The α1D integrin was visualized using α1D-antibody overnight. All primary antibodies were followed by a 1:5000 goat-anti-rabbit secondary antibody (Li-Cor Biosciences, Lincoln, Nebr.) for 1 hour. Galectin-1 was detected with a 1:1000 dilution of H00003956-D01P (Abnova, Walnut, Calif.). Galectin-3 was detected with a 1:1000 dilution of ab53082 (Abeam, Cambridge, Mass.). Immunoblots were normalized by using a 1:5000 dilution of an anti-α tubulin (AbCam, Cambridge, Mass.) antibody followed by a 1:5000 dilution of goat-anti-mouse secondary antibody, Band intensities were determined with an Odyssey Imaging System.

Immunofluorescence.

Cryosections (8 μm) of 4 week old male Tibialis Anterior (TA) muscle were cut using a LeicaCM 1850 cryostat and mounted on precleaned Surgipath slides. Sections were fixed using 4% paraformaldehyde (PFA) for 2 or 5 minutes then rehydrated using Phosphate Buffered Saline (PBS). Slides were blocked in 5% Bovine Serum Albumin (BSA) in PBS then incubated with laminin-α2G or α1D integrin antibody. For detection of Galectin-1 H00003959-D01P (Abnova) antibody was used. Galectin-3 was visualized using ab53082 (abcam). Antibody T3413 (Sigma) was used to detect Tenascin C. MMP2 and TIMP1 were detected using antibodies ab37150 and ab86482 respectively (Abcam). Slides were then incubated using an appropriate secondary which was a FITC-anti rabbit in all cases except for Tenascin C which was a FITC-anti rat secondary antibody. For detection of spectrin, slides were fixed for 1 minute in ice cold acetone then treated with the M.O.M™ kit according to package instructions (FMK-2201 Vector Laboratories, inc. Burlingame, Calif.). A mouse monoclonal spectrin antibody (Novo Castra NCL-spec2) was then used at 1:100 for 30 minutes followed by a FITC-anti mouse secondary at 1:1000 for 1 hour. Slides were mounted using Vectashield with DAPI and imaged using a Zeiss Axioskop 2 Plus fluorescent microscope. Images were captured using a Zeiss AxioCam HRc digital camera with Axiovision 4.1 software.

Inflammatory Cell Infiltrate.

Four week old TA muscle cryosections were fixed in 4% PFA for 5 minutes followed by rehydration with PBS. Slides were incubated with FITC Rat Anti-Mouse CD11b antibody (BD Biosciences, San Jose, Calif.) at 1:1000 for 1 hour to detect macrophages in the muscle tissue. Slides were washed with PBS and mounted using Vectashield with DAPI. Muscle sections from five mice of each genotype were analyzed and CD11b positive cells per twenty fields at 400× magnification were counted. A Zeiss Axioskop 2 Plus fluorescent microscope was used to view the slides and images were captured using a Zeiss AxioCam HRc digital camera with Axiovision 4.1 software Confocal Microscopy.

The TA muscles from 4 week old male mice from each genotype were sectioned and subjected to immunfluorescence. For detection of α7B integrin sections were fixed in ice cold acetone (−20° C.) for 1 minute then rehydrated using phosphate-buffered saline (PBS). Cryosections were blocked in a 5% bovine serum albumin in PBS solution for 20 minutes followed by incubation with CDB347 (which recognizes the cytoplasmic domain of both mouse and rat α7B integrin) or α1D A2 antibodies for 1 hour. Slides were then washed with 1% BSA and incubated with FITC-conjugated anti-rabbit antibody for 1 hour. Slides were again washed with 1% BSA. To outline the myofibers sections were incubated with rhodamine labeled wheat germ agglutinin for 30 minutes. Slides were mounted using Vectashield with DAPI. Images were captured using an Olympus Fluoview™ Confocal Scanning System.

Survival and Weight Gain Analysis.

Male mice were allowed to age and monitored daily for weight loss and any signs of pain, distress or illness. A weight loss of >10% over a one week period was also considered a terminal sign and the animals were humanely euthanized. Weights from animals of each genotype were compared at 3, 8, and 12 weeks of age.

Grip Strength and Activity Assays.

The forelimb grip strength of four and eight week-old male wild-type, $dy^W$−/− and $dy^W$−/−; itga7+ mice were measured using a SDI Grip Strength System and a Chatillon DFE Digital Force Gauge (San Diego Instruments, Inc., San Diego, Calif.) as per standard protocol. Five consecutive tests were performed for each mouse and the data averaged for each mouse genotype. In order to assess mobility four and eight week old male wild-type, $dy^W$−/− and $dy^W$−/−; itga7+ mice were placed in a clean cage by themselves and monitored for five minutes. Periods of moving about the cage, standing up, and digging were considered times of activity. Additionally during this time period the number of times the mouse stood up was recorded. Stand up testing was only performed on animals which were physically able to stand up. Some mice were excluded from these samples due to the extent of their peripheral neuropathy.

Hematoxylin and Eosin Staining.

Cryosections from 4 week-old TA and diaphragm muscle were stained using Hematoxylin and Eosin and used to determine the percentage of myofibers that contained centrally located nuclei using a Zeiss Axioskop 2 plus fluorescent microscope. A minimum of 1000 fibers per animal (5 animals per group) were counted and the percentage of myofibers with centrally located nuclei calculated. Images were captured using a Zeiss AxioCam HRc digital camera and Axiovision 4.1 software.

Myofiber Area Determination.

Cryosections from 4 week old TA and diaphragm muscles were fixed for 5 minutes in 4% paraformaldehyde (PFA) and rehydrated in PBS. Myofibers were outlined with 2 μg/ml Oregon Green-488 conjugated WGA (Molecular Bioprobes, Eugene, Oreg.) for 30 minutes. Sections were then washed with PBS for 15 minutes and mounted in Vectashield. A minimum of 1000 fibers per animal with five animals per group were assessed for the TA muscle. For diaphragm muscle a minimum of 500 fibers per animal with five animals per genotyped were used. Myofiber cross-sectional area was determined with a Zeiss Axioskop 2 Plus fluorescent microscope and images were captured with a Zeiss AxioCam HRc digital camera with Axiovision 4.1 software.

Quantitative Real-Time PCR Analysis.

Total RNA was purified from five 4 week old male mice wild-type, $dy^W$−/−, and $dy^W$−/−; itga7+ gastrocnemius muscles using Trizol (Invitrogen, Carlsbad, Calif.) reagent. After the concentration was determined, mRNA was pooled equally by genotype for cDNA production. The cDNA was prepared from 4 μg of pooled total RNA with random hexamers and Superscript III (Invitrogen, Carlsbad, Calif.) using standard procedures. Quantitative real-time PCR was conducted with 50 pg total cDNA using SYBR Green Jumpstart (Sigma-Aldrich, St Louis, Mo.) with primer sequences to mouse extracellular matrix genes are listed in Table 2 and normalized to Gapdh. The fold change over wild-type was calculated using the ΔΔCt method after normalization and the average fold change in transcript and standard error of the mean were calculated.

Statistics.

Data is reported as the mean+/− standard deviation. One way analysis of variance (ANOVA) was used to compare animals across groups. Kaplan-Meier Log-Rank test was used to determine significance of life span changes. Myofiber cross-sectional area was analyzed using the GLIMMIX statistical analysis package in SAS. A p-value of <0.05 was considered significant.

ii. Results

Transgenic α7 Integrin Expression Alters the Composition of the Extracellular Matrix in Laminin-α2 Deficient Muscle.

The loss of laminin-211/221 in the muscle extracellular matrix is an underlying cause of muscle disease in MDC1A. Since the α7 integrin is a major laminin receptor in muscle we next determined the mechanism by which increased α7β1 integrin rescued $dy^W$−/− mice in the absence of its laminin-211/221 ligand. QRT-PCR was used to examine the expression profile of genes encoding an array of extracellular matrix proteins in the gastrocnemius muscle of 4 week old wild-type, $dy^W$−/− and $dy^W$−/−; itga7+ mice. QRT-PCR revealed that $dy^W$−/− mice exhibited increased levels of a disintegrin and metalloproteinase with thrombospondin motifs 5 (Adamts5), agrin (Agn), collagen 6A1 (Col6A1), Galectin-1 (Lgals1), Galectin-3 (Lgals3), matrix metalloprotease 2 (Mmp2), integrin α3 (Itga3), Integrin α6 (Itgα6), Integrin α7 (Itga7), laminin-α4 (Lama4), laminin-α5 (Lama5), nidogen (Nid1), tenascin C (TnC), tissue inhibitor of metalloproteinase 1 (Timp1) and tissue inhibitor of metalloproteinase 2 (Timp2) transcripts compared to wild-type (Table 6).

TABLE 6

Changes in gene expression in $dy^W$−/− mice.

| Gene Name | $dy^W$−/− (fold increase over Wild-type) | $dy^W$−/−; itga7+ (fold increase over Wild-type) | Significant Change ($dy^W$−/− vs $dy^W$−/−; itga7+) (p-value < 0.05) |
|---|---|---|---|
| Adamts5 | 1.97 ± 0.14 | 2.33 ± 0.08 | No |
| Agrn | 9.23 ± 0.53 | 6.55 ± 0.15 | Yes |
| Col6a1 | 5.56 ± 0.27 | 7.45 ± 0.51 | Yes |
| Lgals1 | 9.19 ± 0.28 | 12.13 ± 0.31 | Yes |
| Lgala3 | 70.02 ± 0.83 | 80.43 ± 1.96 | Yes |
| Mmp2 | 19.21 ± 0.86 | 12.40 ± 0.43 | Yes |
| Itga3 | 4.99 ± 0.41 | 4.53 ± 0.23 | No |
| Itga6 | 2.68 ± 0.09 | 3.71 ± 0.09 | Yes |
| Itga7 | 4.08 ± 0.11 | 17.15 ± 0.42 | Yes |
| Lama4 | 11.96 ± 0.40 | 12.60 ± 0.90 | No |
| Lama5 | 5.63 ± 0.34 | 6.16 ± 0.34 | No |
| Nid1 | 4.32 ± 1.56 | 6.07 ± 1.33 | No |
| Tnc | 28.05 ±1.30 | 49.60 ± 3.64 | Yes |
| Timp1 | 276.20 ± 22.35 | 328.56 ± 20.40 | Yes |
| Timp2 | 6.30 ± 0.18 | 6.34 ± 0.21 | No |

Results are the fold increase in expression compared with that in wild-type mice. Significance is taken as P < 0.5.

Transgenic expression of the α7 integrin in $dy^W$−/−; itga7+ mice resulted in reduced levels of agrin and Mmp2 transcripts compared to $dy^W$−/− mice (Table 1). Transgenic expression of the α7 integrin in $dy^W$−/−; itga7+ mice resulted in increased transcripts for CoI6A1, Lgals1, Lgals3, Itga3, Itga6, Itga7, Tnc and Timp1 compared to $dy^W$−/− mice (Table 1).

Next determined was if transgenic expression of the α7 integrin altered expression of Galectin-1 and -3 in the muscle of laminin-α2 null mice. Compared to wild-type mice, Galectin-1 transcript was increased 9.2-fold in $dy^W$−/− muscle and 12.1-fold in $dy^W$−/−; itga7+ animals (Table 1). This increase in Galectin-1 transcript correlated with a 1.8-fold increase in Galectin-1 protein in $dy^W$−/−; itga7+ animals compared to wild-type. These results indicate an increase in Galectin-1 protein in the gastrocnemius muscle of $dy^W$−/−; itga7+ animals.

Galectin-3 transcript was increased 70-fold and 80-fold in 4 week old $dy^W$−/− and $dy^W$−/−; itga7+ muscle respectively compared to wild-type (Table 1). This increase in Galectin-3 transcript resulted in a 2-fold increase in Galectin-3 protein in $dy^W$−/− mice and a 7-fold increase in Galectin-3 protein in $dy^W$−/−; itga7+ animals compared to wild-type. These results indicate loss of laminin-α2 resulted in increased Galectin-3 in the muscle extracellular matrix of $dy^W$−/− mice and that transgenic expression of α7 integrin further enhanced the levels of Galectin-3 in laminin-α2 deficient muscle.

Tenascin C is normally localized at the myotendinous junctions and has been shown to be enriched at extrajunctional sites of laminin-α2 deficient muscle which correlate with regions of muscle regeneration. QRT-PCR was used to examine if transgenic overexpression of the α7 integrin altered the expression of tenascin C in the muscle of $dy^W$−/− mice. QRT-PCR confirmed a 28-fold increase in tenascin C transcript in the gastrocnemius muscle of $dy^W$−/− mice and a 49-fold increase in tenascin C transcript in $dy^W$−/−; itga7+ gastrocnemius muscle compared to wild-type. These results indicate transgenic expression of the α7 integrin augmented tenascin C transcription in laminin-α2 null muscle.

Immunofluorescence was used to confirm qRT-PCR and immunoblotting for several proteins Immunofluorescence also demonstrated increased extracellular galectin 1, Galectin-3, and Tenascin C in the extracellular matrix with Galectin-3 and tenascin C being more prevalent in the $dy^W$−/−; itga7+ mice. Immunostaining demonstrated reduced MMP2 and increased TIMP1 in the extracellular matrix of the $dy^W$−/−; itga7+ mice compared with the $dy^W$−/− mice. These results indicate that overexpression of the α7 integrin results in both augmentation and stabilization of the existing extracellular matrix in $dy^W$−/−; itga7+ animals.

Transgenic Expression of α7 Integrin Prevents Muscle Disease Progression in the Diaphragm of $Dy^W$ Mice.

MDC1A patients exhibit severe restrictive respiratory syndrome and require ventilator assistance to breathe as a result of severe diaphragm muscle pathology. Histological analysis and measurements of myofiber area were used to examine if transgenic expression of the α7 integrin prevented the onset of severe diaphragm muscle pathology. H&E studies revealed transgenic expression of the α7 integrin in 4 week old $dy^W$−/− diaphragm muscle resulted in reduced mononuclear cell infiltrate, hypotrophic muscle fibers, centrally located nuclei and fibrosis.

Analysis of myofiber cross-sectional areas confirmed the improvement in the muscle pathology observed in the histological studies. Compared to wild-type with a peak myofiber cross-sectional area of between 3.5-4.5 $\mu m^2$, $dy^W$−/− muscle exhibited a large number of hypotrophic muscle fibers with a peak myofiber area of only 2 $\mu m^2$. In contrast $dy^W$−/−; itga7+ diaphragm myofibers exhibited a peak myofiber area of between 3.5-5 $\mu m^2$ and a curve more similar to wild-type. At the maximum frequency myofiber area, all three groups were significantly different from one another. These results indicate transgenic expression of the α7 integrin prevents muscle disease progression in the diaphragm of laminin-α2 null mice. The studies described in this Example were described in detail by Doe et al. in *J. Cell Science:* 124: 2287-2297, 2011 which is hereby incorporated by reference in its entirety.

Example 4

Galectin-1 Treatment Decreases Muscle Damage in Mdx Mice

This example illustrates Galectin-1 increases muscle repair in mdx mice.

Figure 12:
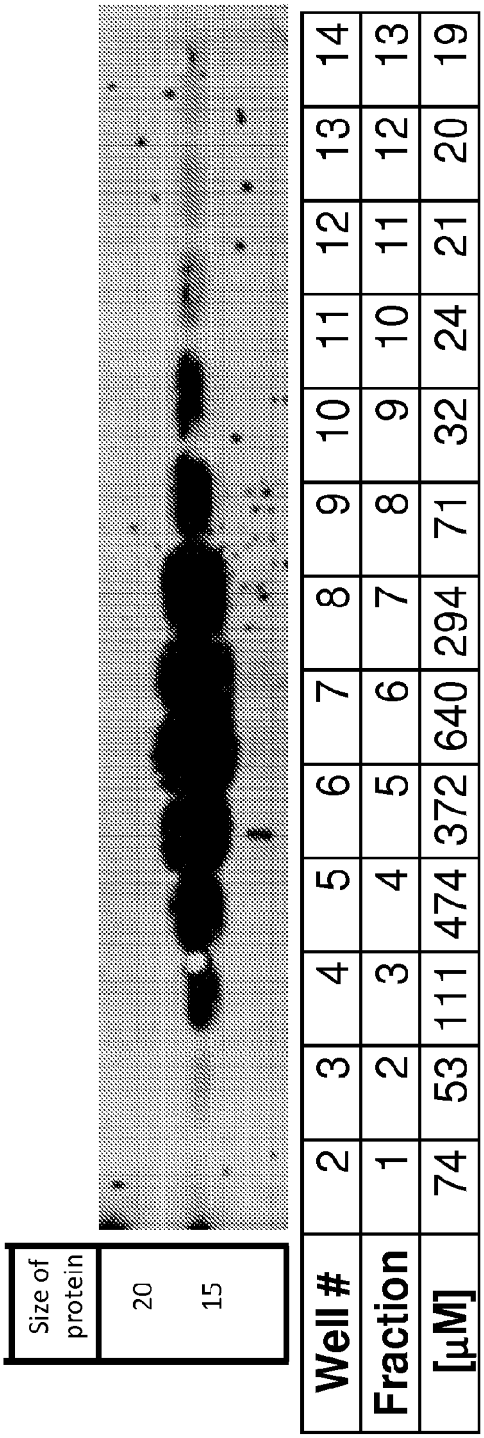
FIG. 12 is a digital image of Galectin-1 fractions eluted from Talon affinity columns.

To produce recombinant Galectin-1, PCR amplified LGALS1 cDNA isolated from total mouse muscle mRNA was cloned into a pET23b vector. Rosetta *E. coli* cells were transformed with pET23b-LGALS1 vector utilizing standard techniques. Recombinant Galectin-1 was isolated and determined to have a sequence corresponding to GENBANK® Accession No. NP_032521.1 as provided by GENBANK® on Aug. 10, 2012 except with a single amino acid substitution at amino acid position 10, in which glutamine (Q) was substituted for leucine (L). Recombinant Galectin-1 was purified by loading induced cell lysate onto Talon affinity column. The purity of Galectin-1 fractions was then determined by using BCA protein analysis, Western blot analysis and Coomassie blue staining (see FIG. 12).

Figure 13:
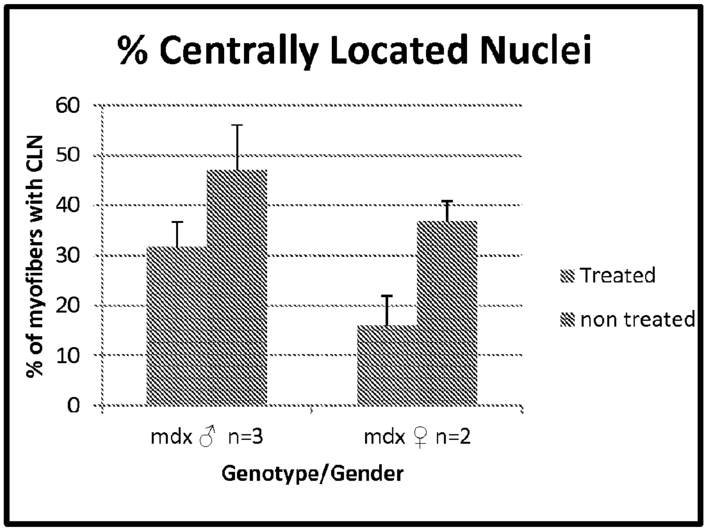
FIG. 13 is a graph and table illustrating Galectin-1 treatment decreases muscle damage in mdx mice.
Figures 17A, 17B, 17C, 17D, 17E, 17F, 17G, 17H, 17I, 17J:
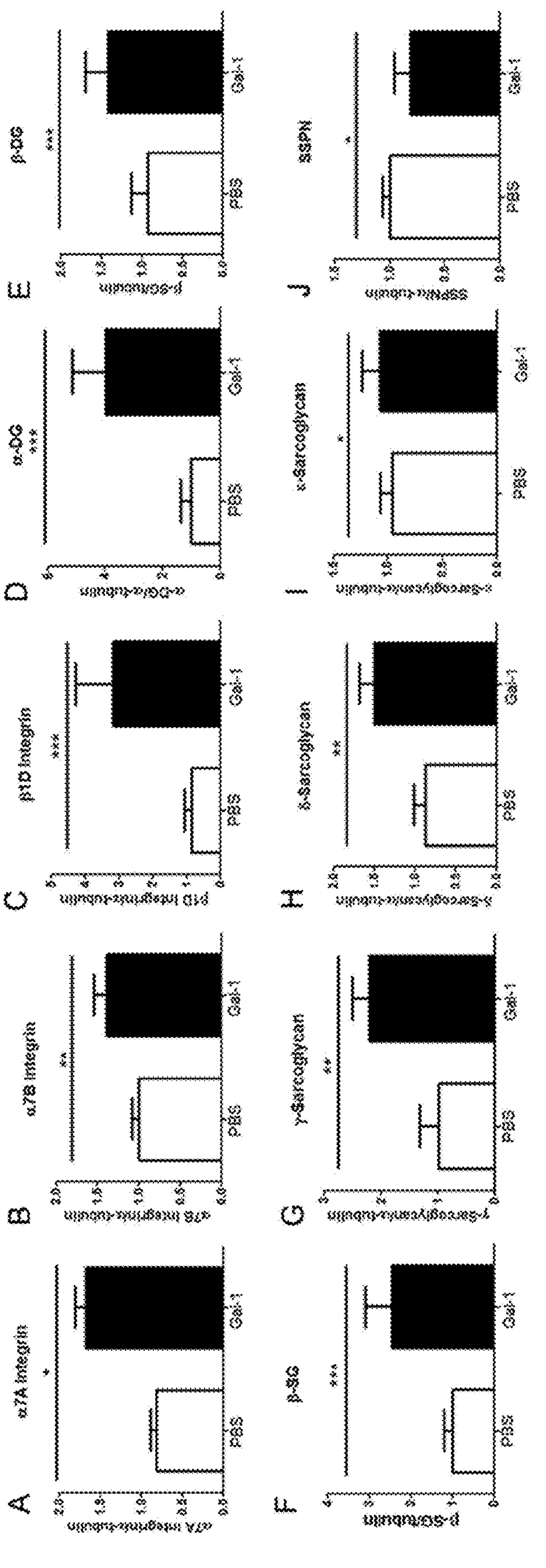
FIGS. 17A-17J are bar graphs illustrating Galectin-1 treatment of mdx mice increases protein levels of members of the sarcolemmal stabilizing dystroglycan complex (DGC) which are normally lost in the absence of dytrophin. The TA proteins of mdx mice treated weekly by intraperitoneal injections of PBS or 5 mg/kg recombinant Galectin-1 and were examined using standard western blotting procedures. Results for α7A Integrin (FIG. 17A), α7B Integrin (FIG. 17B), β1D Integrin (FIG. 17C), α-dystroglycan (FIG. 17D), β-dystroglycan (FIG. 17E), β-sarcoglycan (FIG. 17F), γ-sarcoglycan (FIG. 17G), δ-sarcoglycan (FIG. 17H), ϵ-sarcoglycan (FIG. 17I), and sarcospan (FIG. 17J) were quantified for the two mouse groups and graphed relative a-tubulin. Significance was calculated by student t-test (*p<0.05, p<0.01, *p<0.001).

To determine the effect of Galectin-1 treatment on muscle damage in mdx mice, mdx mice were injected with 100 μl of 13 μM recombinant Galectin-1 through intramuscular injections into their TA muscle. Sections of TA muscle were stained using Hematoxylin and Eosin (H&E). The mdx TA injected with Galectin-1 showed decreased muscle damage over those injected with PBS, as indicated by decreased percentage of myofibers with CLN (FIG. 13). FIG. 14 illustrates Galectin-1 treatment increases α7 integrin. These studies indicate that Galectin-⅓ protein therapy can be beneficial for MD-Galectin-1 increases alpha7 integrin and provides additional extracellular matrix (ECM) for attachment of muscle cells.

Example 5

Galectin-1 Treatment Increases/Maintains Muscle Strength and/or Bone Density

This example illustrates Galectin-1 treatment can be used to increase and/or maintain muscle strength and/or bone density.

i. Material and Methods

Recombinant Galectin-1 Production.

The mouse Galectin-1 cDNA was produced using standard reverse transcriptase (Superscript III, Invitrogen) from mouse muscle Total RNA (Trizol, Invitrogen) followed by PCR using Platinum Taq Supermix (Invitrogen). This PCR product was then subcloned into the pGEM T-Easy vector, sequenced and compared to NCBI database sequence, and finally cloned into the pet23b vector (EMD Millipore) in frame with the 6× His tag. This vector was then transfected into Rosetta *e. coli* (EMD Millipore), grown and induced with 0.4 mM IPTG (Invitrogen) to express Galectin-1. Galectin-1 was then purified as described in the pet vector handbook using the nickel Talon (Clontech) column and imidazole (Sigma-Aldrich) buffer for elution. Purified Galectin-1 was then dialyzed in PBS and used in various studies.

Tissue Culture.

C2C12 myoblasts and myotubes were grown as previously described (Rooney PNAS 2009). α7βgal+/− myoblasts were originally isolated and maintained as described (Rooney PNAS 2009). Briefly, myoblasts were grown and maintained in DMEM without phenol red (GIBCO, Grand Island, N.Y.), 20% FBS (Atlanta Biologicals, Lawrenceville, Ga.), 0.5% chick-embryo extract (CEE, Seralab, West Sussex, UK), 1% L-glutamine (GIBCO, Grand Island, N.Y.) and 1% penicillin/streptomycin (PS) (GIBCO, Grand Island, N.Y.). All myoblasts were maintained below 70% confluence until use in assay. Myoblasts were differentiated into myotubes in DMEM without phenol red (GIBCO, Grand Island, N.Y.), 1% horse-serum, and 1% Penicillin/Streptomycin (P/S)+L-Glutamine. All cells were maintained in TC incubators at 37° C. with 5% CO2.

Myoblast α7 Integrin Drug Enhancement Assay.

A total of 5000 α7βgal$^{-/-}$ myoblasts were dispensed in 100 μL growth media using a 12-well multi-pippette onto Nunc black sided TC coated 96-well plate. After 24 hours different concentrations of recombinant Galectin-1 were added to treatment wells, with identical amounts of PBS added as a negative control for comparison. After incubating for 48 hours the media was aspirated, and cells were lysed with 50 μL of Mammalian Protein Extraction Reagent (MPER) per well followed by incubation at RT for 10 minutes. β-galactosidase (βgal) levels in each well were determined by adding 50 μL of FDG solution (20% 0.1M Sodium phosphate buffer pH 7.0 (Sigma), 0.2% 1 M mgC12 (Sigma), 0.2% 20 mM Fluorescein di-galactoside (FDG) (Marker Gene Technologies), and 79.6% dH2O) and incubating for 20 minutes at RT in the dark. 100 μL/well stop solution (2× TE) was then added and plates were read for fluorescence on the Victor V (Perkin-Elmer) with an excitation filter at 485 nm, an emission filter at 535 nm, and a 0.1 s/well count time.

Galectin Treatment of C2C12 Myoblasts.

C2C12 myoblasts were treated with different amounts of recombinant Galectin-1 for 48 hours, washed in PBS, and lysed in either 1×RIPA with protease inhibitor cocktail for western blotting or in Trizol (Invitrogen) for quantitative real-time PCR. Intramuscular (IM) Tibialus anterior (TA) treatments. Between 20 ng and 150 μg of Galectin-1 was delivered into the left mouse TA muscle by IM injection with an equal volume of PBS delivered to the right. Mice were then sacrificed 48 hours later and the TA muscles were removed for use in other studies.

Intraperitoneal (IP) Galectin-1 treatments: Treatment of mice was started at 10 days of age either weekly or biweekly with 5 mg/kg or 20 mg/kg of recombinant Galectin-1 and with corresponding volume of PBS as controls. All treatments were well tolerated with no observed side-effects and positive results on muscle and bone. Mouse grip strength was determined using a tensometer as previously described (Rooney, PNAS 2009, which is hereby incorporated by reference in its entirety).

Western Blotting.

Protein concentrations of extracts from myoblast or mouse gastrocnemius tissue (protein extracted in RIPA+ Prot Inhibs) were analyzed by BCA (Pierce) and then loaded at identical concentrations into SDS-PAGE gels and run under standard conditions. Proteins were then transferred to nitrocellulose and probed using the rabbit polyclonal or mouse monoclonal antibodies against α7a Integrin, α7B Integrin, Galectin-1 (AbNova H00003956-D01P), β1D Integrin, α-dystroglycan, 3-dystroglycan H-242 (sc-28535), β-sarcoglycan H-98 (sc-28279), γ-sarcoglycan Z-24 (sc-133984), δ-sarcoglycan H-55 (sc-28281), ε-sarcoglycan H-67 (sc-28282, all sc antibodies are from SantaCruz Biotechnology), and sarcospan.

Quantitative Real-Time PCR (qRTPCR).

Total RNA from powdered mouse TA muscle or myoblasts was isolated using Trizol (Invitrogen, Grand Island, N.Y.) followed by DNase treatment (Promega, Madison, Wis.), and cDNA was made with random hexamers (IDTDNA) and Superscript III (Invitrogen, Grand Island, N.Y.) using standard procedures. Quantitative real-time PCR was performed using Quanta Perfecta SYBR-Green with ROX Master Mix and was run and analyzed as previously described (Doe et al., *J. Cell Science:* 124: 2287-2297, 2011). Primers against ITGA7, ITGB1, and LGALS1 were described in Doe et al, (Id.).

Crysectioning and Histology.

10 μm sections of TA muscles from mice were obtained using a Leica Cryostat. Hemotoxylin and eosin (H&E) staining was performed using standard procedures and images were taken using an Olympus Fluoview FV1000 Laser Confocal Microscope. Centrally located nuclei counts and minimum Ferrets diameter measurements were performed using standard procedures.

Mouse Digital Radiography.

Digital radiography was performed on 5-week and 10-week old mdx mice using a Sound-eklin tru/Digital radiography machine. Femur, lower jaw, and tibia length measurements involved the use of both Sound-eklin eSeries software and Image J and were simple line/curve length measurements from the radiograph. Spinal curvature (kyphosis) was analyzed by drawing a line from the base of the spine at the neck to the base of the spine at the beginning of the hip bone, A perpendicular line was then drawn from the apex of the spinal curve and the length of this line was used to measure kyphosis.

Statistical Analysis.

All statistical analysis was performed using GraphPad Prism 5 software. Averaged data are reported as the mean±the standard error of the mean (s.e.m.). Comparison for two groups was performed using a Student's t-test and between multiple groups using Kruskal-Wallis one-way ANOVA on ranks for nonparametric data. $P<0.05$ was considered statistically significant.

ii. Results

Figure 18C:
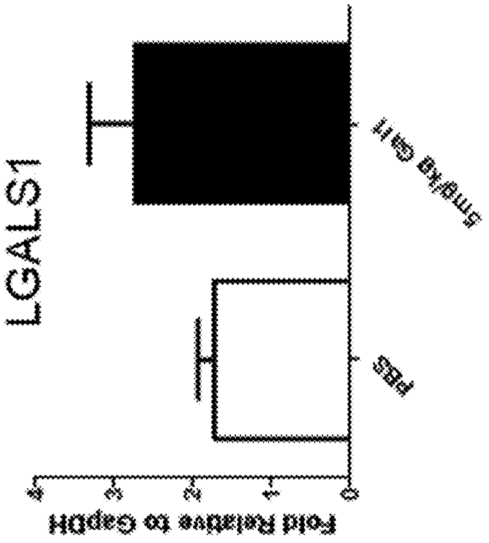
FIGS. 18A-18C are bar graphs illustrating galectin-1 treatment of mdx mice increases transcript levels of members of the α7β1 Integrin complex and LGALS1. The TA transcripts of mdx mice treated weekly by intraperitoneal injections of PBS or 5 mg/kg recombinant Galectin-1 and were analyzed using quantitative real-time PCR. Results for ITGA7 (FIG. 18A), ITGB1 (FIG. 18B), and LGALS1 (FIG. 18C) are shown after calculating relative fold compared to GAPDH.
Figure 18B:
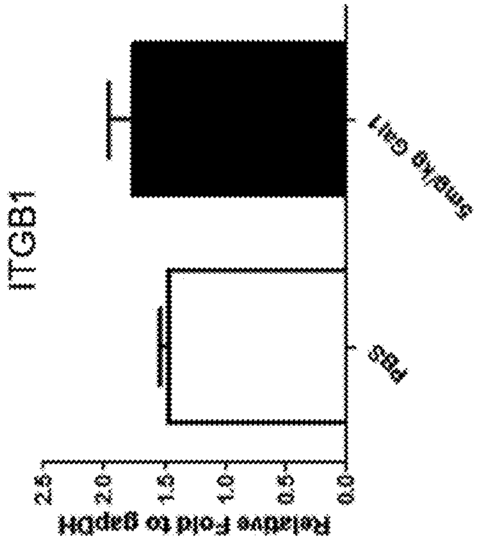
Figure 18A:
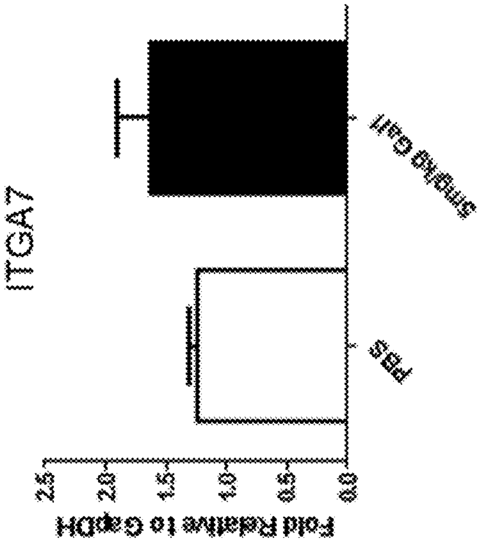
Figure 20:
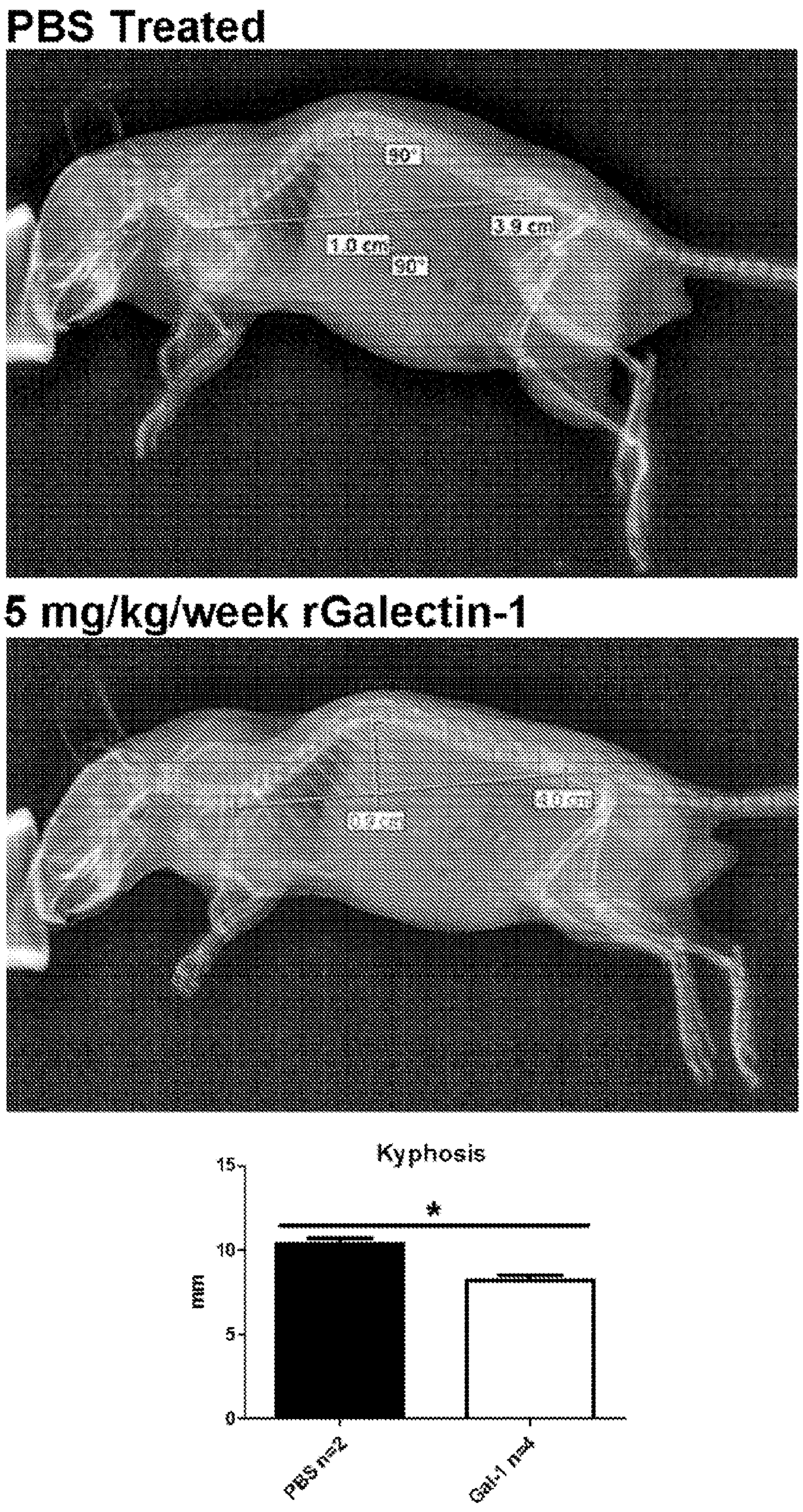
FIG. 20 is a set of digital images and a bar graph showing galectin-1 treatment of mdx mice leads to increased muscle strength which prevents kyphosis in 10-week old mice. Sagittal X-ray images were taken of PBS (top, n=2) or 5 mg/kg/week recombinant Galectin-1 (bottom, n=4) treated mdx mice at 10-weeks of age. Spinal curvature (kyphosis) was analyzed by drawing a line from the base of the spine at the neck to the base of the spine at the beginning of the hip bone. A perpendicular line was then drawn from the apex of the spinal curve and the length of this line was used to measure kyphosis. Significance was calculated by student t-test (*p<0.05).
Figures 21A, 21B, 21C, 21D, 21E, 21F:
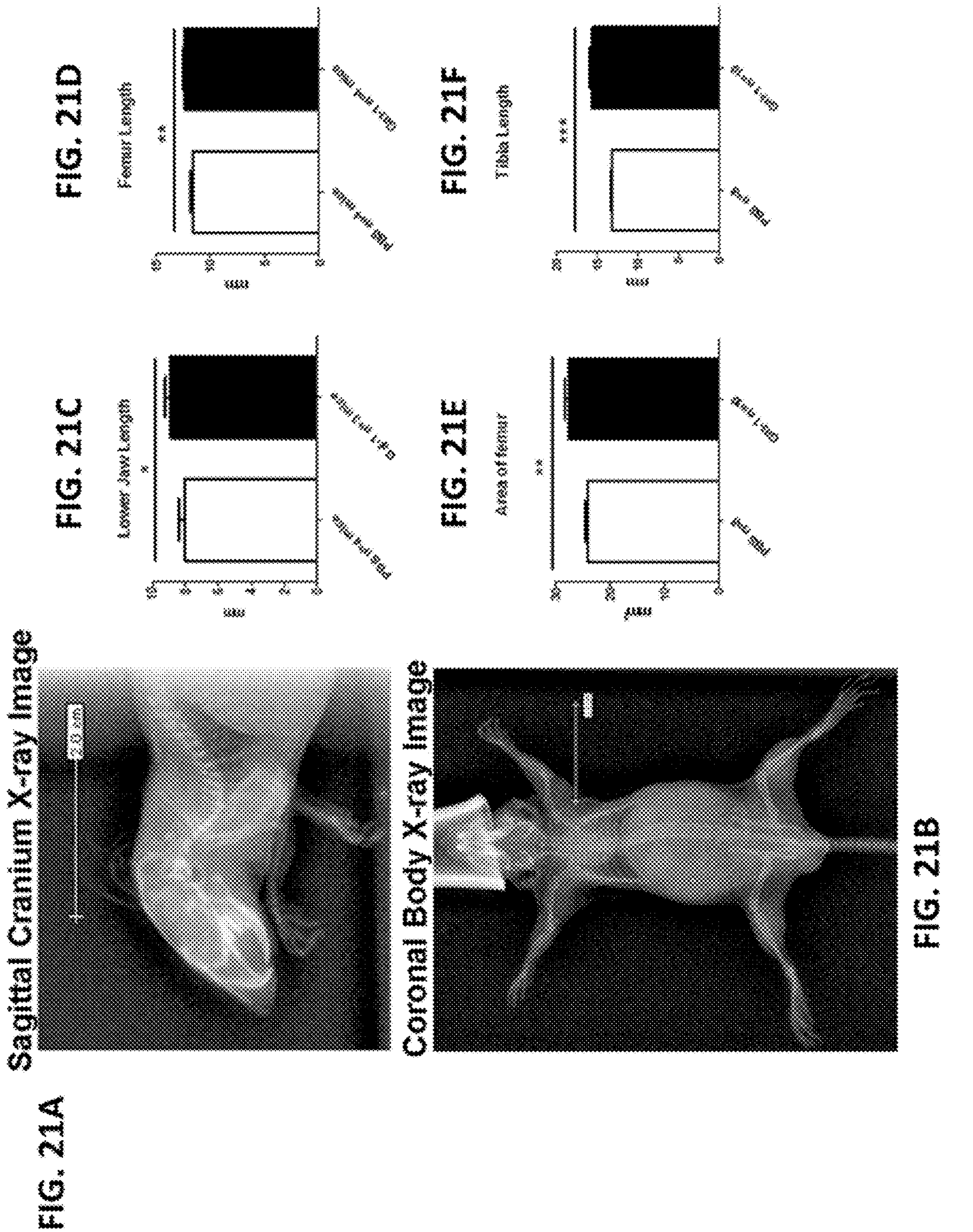
FIGS. 21A-21F illustrate galectin-1 treatment of mdx mice leads to increased bone growth during development. Sagittal cranium (FIG. 21A, example) and coronal body (FIG. 21B, example) X-ray images were taken of PBS or 5 mg/kg/week recombinant Galectin-1 treated mdx mice at 10-weeks of age. From these images the lower jaw lengths (FIG. 21C), femur lengths (FIG. 21D), femur area (FIG. 21E), and tibia lengths (FIG. 21F) were measured and graphed. Significance was calculated by student t-test (*p<0.05, p<0.01, *p<0.001).

FIGS. 15A-15D demonstrate Galectin-1 treatment of myoblasts and myotubes leads to elevated levels of $\alpha7$ and $\beta1$ Integrins at both the transcript and protein levels. FIGS. 16A-16D show intermuscular (IM) injections of mdx mouse tibialus anterior (TA) muscles with recombinant Galectin-1 reduced muscle damage and the need for regeneration as determined by the histological appearance of centrally located nuclei (CLN). Galectin-1 treatment of mdx mice was also found to increase protein levels of members of the sarcolemmal stabilizing dystroglycan complex (DGC) which are normally lost in the absence of dytrophin (see FIGS. 17A-17J). Galectin-1 treatment of mdx mice increased transcript levels of members of the $\alpha7\beta1$ Integrin complex and LGALS1 (see FIGS. 18A-18C). FIGS. 19A-19D are graphs illustrating galectin-1 treatment of mdx mice increasd relative strength, decreases fatigue, and normalizes muscle histological fiber size. Galectin-1 treatment of mdx mice increased muscle strength which prevented kyphosis in 10-week old mice (FIG. 20). Further, Galectin-1 treatment of mdx mice increased bone growth during development (see FIGS. 21A-21F). These studies clearly demonstrate the therapeutic activities of Galectin-1 and in particular, the ability of Galectin-1 to increase muscle strength, bone growth, decrease muscle damage, and decrease muscle fatigue.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of increasing sarcolemmal stabilizing dystroglycan complex for increasing or maintaining muscle strength, muscle density, and/or bone density in a subject suffering from Duchenne muscular dystrophy (DMD), merosin deficient congenital muscular dystrophy Type 1A (MDC1A), limb-girdle muscular dystrophy (LGMD), facioscapulohumeral muscular dystrophy (FHMD), or Beckers muscular dystrophy (BMD), the method comprising systemically administering an effective amount of a Galectin-1 composition comprising a native mammalian Galectin-1 protein or a recombinant Galectin-1 protein having a full-length wild-type amino acid sequence, to the subject with DMD, MDC1A, LGMD, FHMD, or BMD and in need thereof, wherein the effective amount increases sarcolemmal stabilizing dystroglycan complex, thereby increasing or maintaining muscle strength, muscle density, and/or bone density.

2. The method of claim 1, wherein the subject has Duchenne muscular dystrophy.

3. The method of claim 1, wherein the Galectin-1 composition comprises a native mammalian Galectin-1 protein or a recombinant Galectin-1 protein having a full-length wild-type amino acid sequence and a carrier.

4. The method of claim 3, wherein the Galectin-1 composition is administered intramuscularly.

5. The method of claim 3, wherein the Galectin-1 composition is administered intraperitoneally.

6. The method of claim 3, wherein systemic administration is intravenous.

7. The method of claim 1, wherein the effective amount is systemically administered at least once daily.

8. The method of claim 7, wherein at least 1 mg of the Galectin-1 composition is administered systemically at least once daily.

9. A method of increasing sarcolemmal stabilizing dystroglycan complex for preventing, inhibiting and/or reducing muscle loss and/or bone loss in a subject suffering from Duchenne muscular dystrophy (DMD), merosin deficient congenital muscular dystrophy Type 1A (MDC1 A), limb-girdle muscular dystrophy (LGMD), facioscapulohumeral muscular dystrophy (FHMD), or Beckers muscular dystrophy (BMD), the method comprising systemically administering an effective amount of a Galectin-1 composition comprising a native mammalian Galectin-1 protein or a recombinant Galectin-1 protein having a full-length wild-type amino acid sequence, to the subject with DMD, MDC1A, LGMD, FHMD, or BMD and in need thereof, wherein the effective amount increases sarcolemmal stabilizing dystroglycan complex, thereby preventing, inhibiting and/or reducing muscle loss and/or bone loss.

10. The method of claim 9, wherein the subject has Duchenne muscular dystrophy.

11. The method of claim 9, wherein the Galectin-1 composition comprises a native mammalian Galectin-1 protein or a recombinant Galectin-1 protein having a full-length wild-type amino acid sequence and a carrier.

12. The method of claim 11, wherein the Galectin-1 composition is administered by intramuscular or intraperitoneal administration.

13. The method of claim 11, wherein systemic administration is intravenous.

14. The method of claim 9, wherein the effective amount is systemically administered at least once daily.

15. The method of claim 14, wherein at least 1 mg of the Galectin-1 composition is administered systemically at least once daily.

* * * * *

UNITED STATES PATENT AND TRADEMARK OFFICE

CERTIFICATE OF CORRECTION

PATENT NO. : 9,867,866 B2
APPLICATION NO. : 14/419063
DATED : January 16, 2018
INVENTOR(S) : Burkin et al.

It is certified that error appears in the above-identified patent and that said Letters Patent is hereby corrected as shown below:

In Column 1, Line 20, please replace "R21 NS58429" with --R21 NS058429--

Signed and Sealed this
Twenty-sixth Day of June, 2018

Andrei Iancu
*Director of the United States Patent and Trademark Office*